US008962316B2

(12) United States Patent
Harlow et al.

(10) Patent No.: US 8,962,316 B2
(45) Date of Patent: *Feb. 24, 2015

(54) CHOROID PLEXUS DEVICE

(75) Inventors: Ed Harlow, Boston, MA (US);
Roderick A. Hyde, Livermore, CA (US); Edward K. Y. Jung, Bellevue, WA (US); Robert Langer, Newton, MA (US); Eric C. Leuthardt, St. Louis, MO (US); Lowell L. Wood, Jr., Livermore, CA (US)

(73) Assignee: The Invention Science Fund I, LLC, Bellevue, WA (US)

(*) Notice: Subject to any disclaimer, the term of this patent is extended or adjusted under 35 U.S.C. 154(b) by 1253 days.

This patent is subject to a terminal disclaimer.

(21) Appl. No.: 11/451,994

(22) Filed: Jun. 12, 2006

(65) Prior Publication Data

US 2007/0134224 A1 Jun. 14, 2007

Related U.S. Application Data

(63) Continuation of application No. 11/389,268, filed on Mar. 24, 2006, now Pat. No. 8,900,865, which is a continuation-in-part of application No. 11/304,486, filed on Dec. 14, 2005, now Pat. No. 8,198,080, which is a continuation-in-part of application No. 11/304,492, filed on Dec. 14, 2005, now Pat. No. 7,855,062, and a continuation-in-part of application No. 11/304,499, filed on Dec. 14, 2005, now Pat. No. 8,278,094.

(51) Int. Cl.
| | | |
|---|---|---|
| C12N 5/071 | (2010.01) | |
| C12N 5/00 | (2006.01) | |
| C12N 5/02 | (2006.01) | |
| A61K 47/48 | (2006.01) | |
| A61K 9/00 | (2006.01) | |
| A61L 27/36 | (2006.01) | |
| A61L 27/38 | (2006.01) | |
| C12N 5/079 | (2010.01) | |
| C12N 5/077 | (2010.01) | |
| A61K 35/12 | (2006.01) | |

(52) U.S. Cl.
CPC ......... *A61K 47/48776* (2013.01); *A61K 9/0024* (2013.01); *A61L 27/3608* (2013.01); *A61L 27/3612* (2013.01); *A61L 27/3808* (2013.01); *A61L 27/3813* (2013.01); *C12N 5/0618* (2013.01); *C12N 5/0654* (2013.01); *A61K 2035/126* (2013.01); *C12N 2510/00* (2013.01)
USPC .......................................... 435/371; 435/395

(58) Field of Classification Search
None
See application file for complete search history.

(56) References Cited

U.S. PATENT DOCUMENTS

| | | | |
|---|---|---|---|
| 4,627,853 A * | 12/1986 | Campbell et al. ............. | 128/898 |
| 4,833,083 A | 5/1989 | Saxena | |
| 5,256,418 A | 10/1993 | Kemp et al. | |
| 5,324,294 A | 6/1994 | Elia et al. | |
| 5,578,485 A | 11/1996 | Naughton et al. | |
| 5,843,781 A | 12/1998 | Ballermann et al. | |
| 5,916,554 A | 6/1999 | Dionne et al. | |
| 5,916,870 A | 6/1999 | Lee et al. | |
| 5,928,635 A | 7/1999 | Schmidt | |
| 6,017,496 A | 1/2000 | Nova et al. | |
| 6,126,936 A | 10/2000 | Lanza et al. | |
| 6,200,347 B1 | 3/2001 | Anderson et al. | |
| 6,646,867 B1 | 11/2003 | Tuttle et al. | |
| 6,709,269 B1 | 3/2004 | Altshuler | |
| 6,790,455 B2 | 9/2004 | Chu et al. | |
| 2001/0000802 A1 | 5/2001 | Soykan et al. | |
| 2002/0006437 A1 | 1/2002 | Grooms et al. | |
| 2002/0044948 A1 | 4/2002 | Khleif et al. | |
| 2002/0081732 A1 | 6/2002 | Bowlin et al. | |
| 2002/0090725 A1 | 7/2002 | Simpson et al. | |
| 2002/0156033 A1 | 10/2002 | Bratzler et al. | |
| 2003/0059461 A1 | 3/2003 | Backer et al. | |
| 2003/0064074 A1 | 4/2003 | Chang et al. | |
| 2003/0068817 A1 | 4/2003 | Gazit et al. | |
| 2003/0185807 A1 | 10/2003 | Gazit et al. | |
| 2003/0229400 A1 | 12/2003 | Masuda et al. | |
| 2004/0043481 A1 | 3/2004 | Wilson | |
| 2004/0078090 A1 | 4/2004 | Binette et al. | |
| 2004/0175407 A1 | 9/2004 | McDaniel | |
| 2004/0197375 A1 | 10/2004 | Rezania et al. | |
| 2004/0229333 A1 | 11/2004 | Bowlin et al. | |
| 2004/0241849 A1 | 12/2004 | Kapat | |
| 2005/0101005 A1 | 5/2005 | Steidler | |
| 2005/0226856 A1 | 10/2005 | Ahlfors | |
| 2006/0207168 A1 | 9/2006 | Harper | |
| 2007/0134224 A1 | 6/2007 | Harlow et al. | |

(Continued)

FOREIGN PATENT DOCUMENTS

| | | |
|---|---|---|
| WO | WO 95/24929 | 9/1995 |
| WO | WO 96/40947 | 12/1996 |

(Continued)

OTHER PUBLICATIONS

Zheng et al. "Primary Culture of Choroidal Epithelial Cells: Characterization of an In Vitro Model of Blood-CSF Barrier" In Vitro Cell. Dev. Biol.—Animal 34:40-45, Jan. 1998.*

Alverson, Andrew J.; Theriot, Edward C.; "Research Article: Comments on Recent Progress Toward Reconstructing the Diatom Phylogeny"; Journal of Nanoscience and Nanotechnology; bearing a date of 2005; pp. 57-62; vol. 5, No. 1; American Scientific Publishers.

Anderson, M.W.; Holmes, S.M.; Mann, R.; Foran, P.; Cundy, C.S.; "Research Article: Zeolitisation of Diatoms"; Journal of Nanoscience and Nanotechnology; bearing a date of 2005; pp. 92-95; vol. 5, No. 1; American Scientific Publishers.

(Continued)

*Primary Examiner* — Thane Underdahl
(74) *Attorney, Agent, or Firm* — Dorsey & Whitney LLP

(57) ABSTRACT

Bone cages are disclosed including devices for biocompatible implantation. The structures of bone are useful for providing living cells and tissues as well as biologically active molecules to subjects.

25 Claims, 17 Drawing Sheets

(56) References Cited

U.S. PATENT DOCUMENTS

| | | |
|---|---|---|
| 2007/0134225 A1 | 6/2007 | Harlow et al. |
| 2008/0033429 A1 | 2/2008 | Harlow et al. |
| 2008/0044900 A1 | 2/2008 | Mooney et al. |
| 2009/0115603 A1 | 5/2009 | Tabe |
| 2010/0272771 A1 | 10/2010 | Harlow et al. |

FOREIGN PATENT DOCUMENTS

| | | | |
|---|---|---|---|
| WO | WO 99/38453 | | 8/1999 |
| WO | WO 99/47080 | | 9/1999 |
| WO | WO 00/00177 | | 1/2000 |
| WO | WO 00/66188 | * 9/2000 | ............ A61L 27/00 |
| WO | WO 01/24690 A2 | | 4/2001 |
| WO | WO 01/68135 A2 | | 9/2001 |
| WO | WO 02/09597 A2 | | 2/2002 |
| WO | WO 2005/041848 A2 | | 5/2005 |

OTHER PUBLICATIONS

Apt, Kirk E.; Kroth-Pancic, Peter G.; Grossman, Arthur R.; "Original Paper: Stable Nuclear Transformation of the Diatom Phaeodactylum Tricornutum"; Molecular Genetics and Genomics; bearing a date of 1996; pp. 572-579; vol. 252; Springer-Verlag.

Apt, Kirk E.; Zaslavkaia, Lioudmila; Lippmeier, J. Casey; Lang, Markus; Kilian, Oliver; Wetherbee, Rick; Grossman, Arthur R.; Kroth, Peter G.; "Research Article: In Vivo Characterization of Diatom Multipartite Plastid Targeting Signals"; Journal of Cell Science; bearing a date of 2002; pp. 4061-4069; vol. 115, No. 21; The Company of Biologists Ltd.; located at: http://jcs.biologists.org/cgi/content/abstract/115/21/4061.

Bradbury, Jane; "Feature: Nature's Nanotechnologists: Unveiling the Secrets of Diatoms"; Public Library of Science—Biology; bearing a date of Oct. 2004; pp. 1512-1515; vol. 2, No. 10; Jane Bradbury; located at: www.plosbiology.org.

Caspi, Oren; Lesman, Ayelet; Basevitch, Yaara; Gepstein, Amira; Arbel, Gil; Habib, Manhal; Gepstein, Lior; Levenberg, Shulamit; "Tissue Engineering of Vascularized Cardiac Muscle From Human Embryonic Stem Cells"; Circulation Research; bearing a date of Feb. 2, 2007; pp. 1-11; American Heather Association, Inc. located at: http://circres.ahajournals.org/cgi/reprint/01.RES.0000257776. 05673.ffv1.

Colton, C.K.; Avgoustiniatos, E.S.; "Bioengineering in Development of the Hybrid Artificial Pancreas"; Journal of Biomechanical Engineering; bearing a date of May 1991; pp. 152-170; vol. 113.

De Stefano, Mario; De Stefano, Luca; "Nanostructures in Diatom Frustules: Functional Morphology of Valvocopulae in Cocconeidacean Monoraphid Taxa"; Journal of Nanoscience and Nanotechnology; bearing a date of 2005; pp. 15-24; vol. 5, No. 1; American Scientific Publishers.

Dunahay, Terri G.; Jarvis, Eric E.; Roessler, Paul G.; "Genetic Transformation of the Diatoms Cyclotella Cryptica and Navicula Saprophila"; Journal of Phycology; bearing a date of Dec. 1995; pp. 1004-1012; vol. 31, No. 6; Phycological Society of America; located at: http://www.blackwell-synergy.com.

Falciatore, Angela; Casotti, Raffaella; Leblanc, Catherine; Abrescia, Chiara; Bowler, Chris; "Transformation of Nonselectable Reporter Genes in Marine Diatoms"; Marine Biotechnology; bearing a date of May 1999; pp. 239-251; vol. 1, No. 3; Sprinter-Verlag New York, Inc.

Fischer, Harald; Robl, Ingrid; Sumper, Manfred; Kröger, Nils; "Targeting and Covalent Modification of Cell Wall and Membrane Proteins Heterologously Expressed in the Diatom Cylindrotheca Fusiformis (Bacillariophyceae)"; Journal of Phycology; bearing a date of Feb. 1999; pp. 113-120; vol. 35, No. 1; located at http://www.blackwell-synergy.com/links/doi/10.1046/j.1529-8817.1999. 3510113.x.

Frigeri, Luciano G.; Radabaugh, Timothy R.; Haynes, Paul A.; Hildebrand, Mark; "Research: Identification of Proteins from a Cell Wall Fraction of the Diatom Thalassiosira Pseudonana"; Molecular & Cellular Proteomics 5.1; bearing a date of Jan. 2006; pp. 182-193; vol. 5, No. 1; The American Society for Biochemistry and Molecular Biology, Inc.; located at: www.mcponline.org.

Gebeshuber, Ille C.; Stachelberger, Herbert; Drack, Manfred; "Research Article: Diatom Bionanotribology—Biological Surfaces in Relative Motion: Their Design, Friction, Adhesion, Lubrication and Wear"; Journal of Nanoscience and Nanotechnology; bearing a date of 2005; pp. 79-87; vol. 5, No. 1; American Scientific Publishers.

"Genetically Engineered Materials and Micro/Nano Devices"; GEMS; bearing a date of 2006; pp. 1-16; School of Materials Science and Engineering Georgia Institute of Technology; located at: http://www.gems.gatech.edu.

Gordon, Richard; Parkinson, John; "Review: Potential Roles for Diatomists in Nanotechnology"; Journal of Nanoscience and Nanotechnology; bearing a date of 2005; pp. 35-40; vol. 5, No. 1; American Scientific Publishers.

Gordon, Richard; Sterrenburg, Frithjof A.S.; Sandhage, Kenneth H.; "A Special Issue on Diatom Nanotechnology"; Journal of Nanoscience and Nanotechnology; bearing a date of 2005; pp. 1-4; vol. 5, No. 1; American Scientific Publishers.

Hamm, Christian E.; "Research Article: The Evolution of Advanced Mechanical Defenses and Potential Technological Applications of Diatom Shells"; Journal of Nanoscience and Nanotechnology; bearing a date of 2005; pp. 108-119; vol. 5, No. 1; American Scientific Publishers.

Hildebrand, Mark; "Research Article: Prospects of Manipulating Diatom Silica Nanostructure"; Journal of Nanoscience and Nanotechnology; bearing a date of 2005; pp. 146-157; vol. 5, No. 1; American Scientific Publishers.

Kilian, Oliver; Kroth, Peter G.; "Identification and Characterization of a New Conserved Motif Within the Presequence of Proteins Targeted into Complex Diatom Plastids"; The Plant Journal; bearing a date of Jan. 2005; pp. 175-183; vol. 41, No. 2; Blackwell Publishing Ltd; located at: http://www.blackwell-synergy.com/doi/pdf/10.1111/j.1365-313X.2004.02294.x.

Lebeau, Thierry; Robert, Jean-Michel; "Mini-Review: Diatom Cultivation and Biotechnologically Relevant Products. Part I: Cultivation at Various Scales"; Applied Microbiology and Biotechnology; bearing a date of 2003; pp. 612-623; vol. 60, No. 6; Springer-Verlag; located at: www.springerlink.com.

Lebeau, T.; Robert, J.M.; "Mini-Review: Diatom Cultivation and Biotechnologically Relevant Products. Part II: Current and Putative Products"; Applied Microbiology and Biotechnology; bearing a date of Feb. 2003; pp. 624-632; vol. 60, No. 6; Springer-Verlag; located at: www.springerlink.com.

León Y León, Carlos A.; "New Perspectives in Mercury Porosimetry"; Advances in Colloid and Interface Science; bearing a date of 1998; pp. 341-372; vol. 76-77; Elsevier Science B.V.

Linhart, Wolfgang; Peters, Fabian; Lehmann, Wolfgang; Schwarz, Karsten; Schilling, Arndt Friedrich; Amling, Michael; Rueger, Johannes Maria; Epple, Matthias; "Biologically and Chemically Optimized Composites of Carbonated Apatite and Polyglycolide as Bone Substitution Materials"; Journal of Biomedical Materials Research; bearing a date of Feb. 2001; pp. 162-171; vol. 54, No. 2; John Wiley & Sons, Inc.; at: http://www3.interscience.wiley.com/cgi-bin/abstract/75501642/ABSTRACT?CRETRY=1&SRETRY=0.

Lopez, Pascal J.; Descles, Julien; Allen, Andrew E.; Bowler, Chris; "Prospects in Diatom Research"; Current Opinion in Biotechnology; bearing a date of 2005; pp. 180-186; vol. 16; Elsevier Ltd.; located at: www.sciencedirect.com.

Losic, Dusan; Rosengarten, Gary; Mitchell, James G.; Voelcker, Nicolas H.; "Research Article: Pore Architecture of Diatom Frustules: Potential Nanostructured Membranes for Molecular and Particle Separations"; Journal of Nanoscience and Nanotechnology; bearing a date of Apr. 2006; pp. 982-989; vol. 6, No. 4; American Scientific Publishers.

Lutz, Katharina; Gröger, Christian; Sumper, Manfred; Brunner, Eike; "Biomimetic Silica Formation: Analysis of the Phosphate-Induced Self-Assembly of Polyamines"; Physical Chemistry Chemical Physics; bearing a date of Jul. 2005; pp. 2812-2815; vol. 7, No. 14; The Owner Societies 2005; located at www.rsc.org/pccp.

Mironov, Vladimir, MD PhD; Kasyanov, Vladimir A., DSc, PhD; Yost, Michael J., PhD; Visconti, Richard, PhD; Twal, Waleed, PhD;

(56) References Cited

OTHER PUBLICATIONS

Trusk, Thomas, PhD; Wen, Xuejun, MD, PhD; Ozolanta, Iveta, MD, PhD; Kadishs, Arnolds, MD; Prestwich, Glenn D., PhD; Terracio, Louis, PhD; Markwald, Roger R., PhD; "Cardiovascular Tissue Engineering I. Perfusion Bioreactors: A Review"; Journal of Long-Term Effects of Medical Implants; bearing a date of 2006; pp. 111-130; vol. 16, No. 2; Begell House, Inc.; located at: http://begellhouse.com.

Montsant, Anton; Jabbari, Kamel; Maheswari, Uma; Bowler, Chris; "Comparative Genomics of the Pennate Diatom Phaeodactylum Tricornutum"; Plant Physiology; bearing a date of Feb. 2005; pp. 500-513; vol. 137; American Society of Plant Biologists; located at: www.plantphysiol.org.

Montsant, Anton; Maheswari, Uma; Bowler, Chris; Lopez, Pascal J.; "Review: Diatomics: Toward Diatom Functional Genomics"; Journal of Nanoscience and Nanotechnology; bearing a date of 2005; pp. 5-14; vol. 5, No. 1; American Scientific Publishers.

O'Shea, Geraldine M.; Goosen, Mattheus F.A.; Sun, Anthony M.; "BBA Report: Prolonged Survival of Transplanted Islets of Langerhans Encapsulated in a Biocompatible Membrane"; Biochimica et Biophysica Acta; bearing a date of 1984; pp. 133-136; vol. 804; Elsevier Science Publishers B.V.

Pappas, Janice L.; "Research Article: Geometry and Topology of Diatom Shape and Surface Morphogenesis for Use in Applications of Nanotechnology"; Journal of Nanoscience and Nanotechnology; bearing 2005; pp. 120-130; vol. 5, No. 1; American Scientific Publishers.

Pondaven, Philippe; Gallinari, Morgane; Chollet, Sophie; Bucciarelli, Eva; Sarthou, Geraldine; Schultes, Sabine; Jean, Frederic; "Original Paper: Grazing-Induced Changes in Cell Wall Silicification in a Marine Diatom"; Protist; bearing dates of Nov. 7, 2006 and 2007; pp. 21-28; vol. 158, No. 1; Elsevier GmbH; located at: www.sciencedirect.com.

Poulsen, Nicole; Chesley, Patrick M.; Kroger, Nils; "Molecular Genetic Manipulation of the Diatom Thalassiosira Pseudonana (Bacillariophyceae)"; Journal of Phycology; bearing a date of Oct. 2006; pp. 1059-1065; vol. 42, No. 5; Phycological Society of America; located at www.ingentaconnect.com.

Poulsen, Nicole; Kroger, Nils; "A New Molecular Tool for Transgenic Diatoms Control of mRNA and Protein Biosynthesis by an Inducible Promoter-Terminator Cassette"; FEBS Journal (Federation of European Biochemical Societies); bearing a date of Jul. 2005; pp. 3413-3423; vol. 272, No. 13; FEBS; located at: http://www.blackwell-synergy.com/doi/abs/10.1111/j.1742-4658.2005.04760.x.

Rorrer, Gregory L.; Chang, Chih-Hung; Liu, Shu-Hong; Jeffryes, Clayton; Jiao, Jun; Hedberg, James A.; "Biosynthesis of Silicon-Germanium Oxide Nanocomposites by the Marine Diatom Nitzschia Frustulum"; Journal of Nanoscience and Nanotechnology; bearing a date of 2005; pp. 41-49; vol. 5, No. 1; American Scientific Publishers.

Scala, Simona; Carels, Nicolas; Falciatore, Angela; Chiusano, Maria Luisa; Bowler, Chris; "Genome Analysis: Genome Properties of the Diatom Phaeodactylum Tricornutum"; Plant Physiology; bearing a date of Jul. 2002; pp. 993-1002; vol. 129; American Society of Plant Biologists; located at: www.plantphysiol.org.

Sterrenburg, F.A.S.; Tiffany, Mary Ann; Del Castillo, Maria Esther Meave; "Research Article: Valve Morphogenesis in the Diatom Genus Pleurosigma W. Smith (Bacillariophyceae): Nature's Alternative Sandwich"; Journal of Nanoscience and Nanotechnology; bearing a date of 2005; pp. 140-145; vol. 5, No. 1; American Scientific Publishers.

Sumper, Manfred; Brunner, Eike; Lehmann, Gerhard; "Biomineralization in Diatoms: Characterization of Novel Polyamines Associated with Silica"; FEBS Letters (Federation of European Biochemical Societies); bearing a date of Jul. 4, 2005; pp. 3765-3769; vol. 579, No. 17; Federation of European Biochemical Societies; Elsevier B.V.; located at www.sciencedirect.com.

Sumper, Manfred; Lehmann, Gerhard; "Silica Pattern Formation in Diatoms: Species-Specific Polyamine Biosynthesis"; Chembiochem: A European Journal of Chemical Biology; bearing a date of Sep. 2006; pp. 1419-1427; vol. 7, No. 9; Wiley-VCH Verlag GmbH & Co. KGaA, Weinheim; located at: http://www3.interscience.wiley.com/cgi-bin/abstract/112747021/ABSTRACT?CRETRY=1&SRETRY=0.

Thamatrakoln, Kimberlee; Hildebrand, Mark; "Research Article: Approaches for Functional Characterization of Diatom Silicic Acid Transporters"; Journal of Nanoscience and Nanotechnology; bearing a date of 2005; pp. 158-166; vol. 5, No. 1; American Scientific Publishers.

Tiffany, Mary Ann; "Research Article: Diatom Auxospore Scales and Early Stages in Diatom Frustule Morphogenesis: Their Potential for Use in Nanotechnology"; Journal of Nanoscience and Nanotechnology; bearing a date of 2005; pp. 131-139; vol. 5, No. 1; American Scientific Publishers.

Vrieling, Engel G.; Sun, Qianyao; Beelen, Theo P.M.; Hazelaar, Sandra; Gieskes, Winfried W.C.; Van Santen, Rutger A.; Sommerdijk, Nico A.J.M.; "Controlled Silica Synthesis Inspired by Diatom Silicon Biomineralization"; Journal of Nanoscience and Nanotechnology; bearing a date of 2005; pp. 68-78; vol. 5, No. 1; American Scientific Publishers.

Wee, Kit Mun; Rogers, Tony N.; Altan, Burhanettin S.; Hackney, Stephen A.; Hamm, Christian; "Research Article: Engineering and Medical Applications of Diatoms"; Journal of Nanoscience and Nanotechnology; bearing a date of 2005; pp. 88-91; vol. 5, No. 1; American Scientific Publishers.

Zaslavskaia, L.A.; Lippmeier, J.C.; Shih, C.; Ehrhardt, D.; Grossman, A.R.; Apt, K.E.; "Reports: Trophic Conversion of an Obligate Photoautotrophic Organism Through Metabolic Engineering"; Science; bearing a date of Jun. 15, 2001; pp. 2073-2075; vol. 292, No. 5524; located at: www.sciencemag.org.

Beno, Thoma; Yoon, Young-June; Cowin, Stephen C.; Fritton, Susannah P.; "Estimation of Bone Permeability Using Accurate Microstructural Measurements"; Journal of Biomechanics; bearing a date of 2006; pp. 2378-2387; vol. 39, Elsevier Ltd.; www.elsevier.com/locate/jbiomech and www.JBiomech.com.

Cornford, Eain M.; Hyman, Shigeyo; "Localization of Brain Endothelial Luminal and Abluminal Transporters with Immunogold Electron Microsopy"; NeuroRx: The Journal of the American Society for Experimental NeuroTherapeutics; bearing a date of Jan. 2005; pp. 27-43; vol. 2; The American Society for Experimental NeuroTherapeutics, Inc.

Ghitescu, Lucian; Robert, Manon; "Diversity in Unity: The Biochemical Composition of the Endothelial Cell Surface Varies Between the Vascular Beds"; Microscopy Research and Technique; bearing a date of 2002; pp. 381-389; vol. 57; Wiley-Liss, Inc.; located at www.interscience.wiley.com.

Dalton, Mark; "Phospholipid/Cell Membrane"; bearing a date of 2003; pp. 1-5; located at http:202.114.65.5 1/fzjx/wsw/newindex/website/cellb/chapter2/membrane.html.

Hallgren, Carin et al.; "An in vivo study of bone response to implants topographically modified by laser micromachining"; Biomaterials; bearing a date of 2003; pp. 701-710; Biomaterials 24; Elsevier Science Ltd.

McElhaney, Ronald N.; "Membrane Lipid, Not Polarized Water, is Responsible for the Semipermeable Properties of Living Cells"; Biophysical Journal; bearing a date of 1975; pp. 777-784; vol. 15.

Misch, Carl E., DDS, MDS et al.; "Mechanical Properties of Trabecular Bone in the Human Mandible: Implications for Detal Implant Treatment Planning and Surgical Placement"; J Oral Maxillofac Surg; bearing a date of 1999; pp. 700-708; vol. 57.

PCT International Search Report; International App. No. PCT/US 08/01436; pp. 1-2; Apr. 22, 2009.

Zeigler, Z. et al.; "Microscopic platelet size and morphology in various hematologic disorders"; Blood Journal; bearing a date of Mar. 1978; pp. 479-486; vol. 51, No. 3; American Society of Hematology; Washington DC.

"Bone (anatomy)"; Microsoft Encarta Online Encyclopedia 2003; 1997-2003; p. 1; http://encarta.msn.com.

De Boer, Herman, MD; "The History of Bone Grafts"; Clinical Orthopedics and Related Research; Jan. 1988; pp. 292-298; No. 226; University Hospital Leiden; The Netherlands.

Grant, Gerald A. et al.; "Understanding the Physiology of the Blood-Brain Barrier: In Vitro Models"; News Physiol. Sci.; bearing a date of

(56) References Cited

OTHER PUBLICATIONS

Dec. 1998; pp. 287-293; vol. 13; © 1998 Int. Union Physiol. Sci./Am. Physiol. Soc.; located at http://physiologyonline.physiology.org/cgi/content/full/13/6/287.

U.S. Appl. No. 11/452,019, Harlow et al.

U.S. Appl. No. 11/451,986, Harlow et al.

"Exhibit"; Definition from Merriam-Webster Online Dictionary; bearing a date of 2010; printed on May 19, 2010; 3 pp.; located at http://www.merriam-webster.com/dictionary/exhibit.

Round, F.E.; "Diatoms"; bearing a date of 1990; publication information and p. 31 (total of 2 pages); Cambridge University Press, UK.

Fulton, George P.; "Diatomaceous earth filtration for safe drinking water"; ASCE Publications; bearing a date of 2000; pp. 1-3 (as provided by examiner; no better copy available).

"Cell membrane"; definition from Answers.com; printed on Jun. 18, 2010; 18 pages; located at http://www.answers.com/topic/cell-membrane.

Balda et al; "Tight junctions"; Journal of Cell Science; bearing a date of 1998; pp. 541-547; vol. 111; The Company of Biologists Limited; Great Britain.

Buchert et al.; "Method to Examine Tight Junction Physiology in Cancer Stem Cells: TEER, Paracellular Permeability, and Dilution Potential Measurements"; Stem Cell Rev and Rep; bearing a date of Dec. 3, 2011; pp. 1030-1034; vol. 8; Springer Science+Business Media, LLC.

Pinto De Silva et al.; "On Tight-Junction Structure"; Cell; bearing a date of Mar. 1982; pp. 441-450; vol. 28; MIT.

Tsukita et al.; "Multifunctional Strands in Tight Junctions"; Nature Reviews | Molecular Cell Biology; bearing a date of Apr. 2001; pp. 285-293; vol. 2; Macmillan Magazines Ltd.

Narváez-Vásquez et al.; "Systemins and AtPeps: Defense-Related Peptide signals"; Induced Plant Resistance to Herbivory: Chapter 15; bearing a date of 2008; pp. 313-328; Springer Science+Business Media B. V.

Nichol et al.; "Effectiveness of Live, Attenuated Intranasal Influenza Virus Vaccine in Healthy, Working Adults"; JAMA; Jul. 14, 1999; pp. 137-144; vol. 281, No. 2; American Medical Association.

Qiu et al.; "Environment-sensitive hydrogels for drug delivery"; Advanced Drug Delivery Reviews; bearing a date of Aug. 14, 2001; pp. 321-339; vol. 53; Elsevier Science B. V.

Syto et al.; "Structural and Biological Stability of the Human Interleukin 10 Homodimer"; Biochemistry; bearing dates of Jun. 30, 1998 and Sep. 23, 1998; pp. 16943-16951; vol. 37; American Chemical Society.

The American Heritage® Dictionary of the English Language; "auxotrophic"; located at: http://www.credoreference.com/entry/hmdictenglang/auxotrophic ; Sep. 2, 2012 (date provided by examiner); bearing a date of 2007; © 2007, 2000 Houghton Mifflin Company.

The Columbia Encyclopedia; "Virus"; located at: http://www.credoreference.com/entry/columency/virus ; Sep. 2, 2012 (date provided by examiner); bearing a date of 2008; 1 page.

Komlev et al.; "Porous hydroxyapatite ceramics of bi-modal pore size distribution"; Journal of Materials Science: Materials in Medicine; 2002; pp. 295-299; vol. 13; Kluwer Academic Publishers.

Lu et al.; "Controllable porosity hydroxyapatite ceramics as spine cage: fabrication and properties evaluation"; Journal of Materials Science: Materials in Medicine; 2003; pp. 1039-1046; vol. 14; Kluwer Academic Publishers.

Millipore.com; "Pore Density"; 1 page; screen shot taken on Sep. 7, 2011 from http://www.millipore.com/membrane/fix4/filter_characterization_hm&tab1=1&tab2=2#tab2=2;tab1=1 (Best copy available;as provided by examiner).

Haidinger et al.; "*Escherichia coli* Ghost Production by Expression of Lysis Gene *E* and Staphylococcal Nuclease"; Applied and Environmental Microbiology; bearing a date of Oct. 2003, accepted Jul. 21, 2003; pp. 6106-6113; vol. 69, No. 10; American Society of Microbiology.

Anderson et al.; "Kieselguhrs Suitability as Carriers in Catalysts"; Industrial and Engineering Chemistry; bearing a date of Dec. 1947; pp. 1618-1628; vol. 39, No. 12; U.S. Bureau of Mines.

Shin, Jennifer; "Intro to Diatoms: General Information"; Monterey Bay Aquarium Research Institute; bearing a date of 1999; pp. 1-2; MBARI; located at: www.mbari.org/staff/conn/botany/diatoms/jennifer/introa.htm.

Reinholt, Finn P. et al.; "Osteopontin—a possible anchor of osteoclasts to bone"; Proc. Natl. Acad. Sci. USA; bearing a date of Jun. 1990; pp. 4473-4475; vol. 87.

Definition from Biology Online; "Cell Membrane"; Biology Online Dictionary; cited and printed by examiner on Feb. 24, 2011; total of 1 page (as provided by examiner); located at: www.biology-online.org/dictionary/Cell_membrane.

Excerpt from Encyclopedia Britannica; "Compact Bone"; Encyclopedia Britannica Online; printed on Feb. 10, 2011; total of 1 page (as provided by examiner); located at: http://www.britannica.com/EBchecked/topic/129490/compact-bone.

Ogden, John A.; "Skeletal Injury in the Child"; bearing a date of 2000; total of 2 pages (as provided by examiner); $3^{rd}$ Edition; Springer-Verlag New York, Inc.

Toto et al.; "Fate of Subcutaneous Anorganic Bone Implants"; Journal of Dental Research; bearing a date of Nov.-Dec. 1961; pp. 1127-1135; vol. 40, No. 6; Sage Publications.

"Diatom"; The Columbia Encyclopedia; bearing a date of 2008; 2 pages; located at http://www.credoreference.com/topic/diatom.

"Eukaryotes"; Illustrated Dictionary of Science; bearing a date of 1988; 2 pages; located at: http://www.credoreference.com/topic/eukaryotic_cells.

"Prokaryotes"; Illustrated Dictionary of Science; bearing a date of 1988; 2 pages; located at: http://www.credoreference.com/topic/prokaryotes.

Cecchelli et al.; "In vitro model for evaluating drug transport across the blood-brain barrier"; Advanced Drug Delivery Reviews; bearing a date of 1999; pp. 165-178; vol. 36; Elsevier Science B.V.

Meyer et al.; "Biological and biophysical principles in extracorporal bone tissue engineering Part III"; International Journal of Oral & Maxillofacial Surgery; bearing a date of 2004; pp. 635-641; vol. 33; Elsevier Ltd.

"Portion"; Definition from Merriam-Webster Online Dictionary; bearing a date of 2009; located at http://www.merriam-webster.com/dictionary/portion, 3 pgs.

Agarraberes, Fernando A.; Dice, J. Fred; "Review—Protein translocation across membranes"; Biochimica et Biophysica Acta; bearing a date of 2001; pp. 1-24; vol. 1513; Elsevier Science B.V.; located at: www.bba-direct.com.

Aggarwal, Sudeepta; Pittenger, Mark F.; "Human mesenchymal stem cells modulate allogeneic immune cell responses"; Blood; bearing a date of Feb. 15, 2005, pp. 1815-1822; vol. 105, No. 4; The American Society of Hematology.

Alvarez, F.J.; Herraez, A.; Tejedor, M.C.; "Fluorescence Analysis of Carrier Rat and Human Erythrocytes Loaded With FITC-Dextran"; Cytometry; bearing a date of 1996; pp. 181-189; vol. 24; Wiley-Liss, Inc.

Angele, P., MD; Kujat, R., PhD.; Nerlich, M., MD; Yoo, J., Md; Goldberg, V., MD; Johnstone, B., PhD.; "Engineering of Osteochondral Tissue With Bone Marrow Mesenchymal Progenitor Cells in a Derivatized Hyaluronan-Gelatin Composite Sponge"; Tissue Engineering; Bearing a date of 1999; vol. 5, No. 6; Mary Ann Liebert, Inc, pp. 545-553.

Angelow, Susanne; Zeni, Patrick; Galla, Hans-Joachim; "Usefulness and limitation of primary cultured porcine choroid plexus epithelial cells as an in vitro model to study drug transport at the blood-CSF barrier"; Advanced Drug Delivery Reviews; bearing a date of 2004; pp. 1859-1873; vol. 56; Elsevier B.V.

Beers, Mark H., M.D.; Berkow, Robert, M.D.; "Immunobiology of Rejection"; The Merck Manual of Diagnosis and Therapy: Section 12. Immunology; Allergic Disorders—Chapter 149. Transplantation; bearing a date of 1995-1996; pp. 1-5; Merck & Co., Inc.; located at: http://www.merck.com/mrkshared/mmanual/section12/chapter149/149b.jsp.

Beers, Mark H., M.D.; Berkow, Robert, M.D.; "Transplantation of Other Organs and Tissues"; The Merck Manual of Diagnosis and

(56) References Cited

OTHER PUBLICATIONS

Therapy: Section 12. Immunology; Allergic Disorders—Chapter 149. Transplantation; bearing date of 1999-2005; pp. 1-2; Merck & Co., Inc.; located at: http://www.merck.com/mrkshared/mmanual/section12/chapter149/149i.jsp.
Betz, A. Lorrjs; Firth, J. Anthony; Goldstein, Gary W.; "Polarity of the Blood-Brain Barrier: Distribution of Enzymes Between the Luminal and Antiluniinal Membranes of Brain Capillary Endothelial Cells"; Brain Research; bearing a date of 1980; pp. 17-28; vol. 192; Elsevier/North-Holland Biomedical Press.
Beyth, Shaul; Borovsky, Zipora; Mevorach, Dror; Liebergall, Meir; Gazit, Zulma; Aslan, Hadi; Galun, Eithan; Rachmilewitz, Jacob; "Human mesenchymal stem cells alter antigen-presenting cell maturation and induce T-cell unresponsiveness"; Blood; bearing a date of Mar. 1, 2005; pp. 2214-2219; vol. 105, No. 5; The American Society of Hematology.
Biggerstaff, J.P.; Seth, N.; Amirkhosravi, A.; Amaya, M.; Fogarty, S.; Meyer, T.V.; Siddiqui, F. and Francis, J.L.; "Soluble fibrin augments platelet/tumor cell adherence in vitro and in vivo, and enhances experimental metastasis"; Clinical & Experimental Metastasis; bearing a date of 1999; pp. 723-730; vol. 17; Kluwer Academic Publishers.
"Bone Anabolic Hormones, Their Receptors and Signal Transduction Pathways"; Office of Extramural Research; bearing a date of Oct. 10, 2002; pp. 1-10; National Institutes of Health; located at: located at: http://grants.nih.gov/grants/guide/search_results.htm?text_curr=PA-03-008&Search.x=24&Search.y=4&scope=all&year=all&sort=rel under Announcement Number/ PA-03-008.
Brannon-Peppas, Lisa; "Biomaterials: Polymers in Controlled Drug Delivery"; Medical Plastics and Biomaterials Magazine; bearing a date of Nov. 1997; pp. 1-10; Medical Plastics and Biomaterials; located at: http://www.devicelink.com/grabber.php3?URL=http://www.devicelink.com/mpb/archive/97/11/003.html.
Brown, P.D.; Davies, S.L.; Speake, T.; Millar, I.D.; "Molecular Mechanisms of Cerebrospinal Fluid Production"; Neuroscience; bearing a date of 2004; pp. 957-970; vol. 129; Elsevier Ltd.
Brownlees, J.; Williams, C. H.; "Short Review: Peptidases, Peptides, and the Mammalian Blood-Brain Barrier"; Journal of Neurochemistry; Bearing a date of 1993; pp. 793-803; vol. 60, No. 3; International Society for Neurochemistry.
Brownson, E. A.; Abbruscato, T. J.; Gillespie, T. J.; Hruby, V. J.; Davis, T. P.; "Effect of Peptidases at the Blood Brain Barrier on the Permeability of Enkephalin"; The Journal of Pharmacology and Experimental Therapeutics; Bearing dates of 1994 and Apr. 18, 1994; pp. 675-680; vol. 270, No. 2; The American Society for Pharmacology and Experimental Therapeutics.
Butt, Arthur M.; Jones, Hazel C.; Abbott, N. Joan; "Electrical Resistance Across the Blood-Brain Barrier in Anaesthetized Rats: A Developmental Study"; Journal of Physiology; Bearing a date of Oct. 1990; pp. 47-62; vol. 429; Printed in Great Britain.
Carinci, Francesco; Plattelli, Adriano; Degidi, Marco; Palmieri, Annalisa; Perrotti, Vittoria; Scapoli, Luca; Martinelli, Marcella; Laino, Gregorio; Pezzetti, Furio; "Genetic effects of anorganic bovine bone (Bio-Oss®) on osteoblast-like MG63 cells"; Archives of Oral Biology; bearing a date of 2006; pp. 154-163; vol. 51; located at: www.intl.elsevierhealth.com/journals/arob and at: www.sciencedirect.com.
Charalambides, Charalambos; Beer, Marilyn; Cobb, Andrew G.; "Poor results after augmenting autograft with xenograft (Surgibone) in hip revision surgery"; Acta Orthopaedica; bearing a date of 2005; pp. 544-549; vol. 76, No. 4; Taylor & Francis.
Cohen, Robert E.; Mullarky, Richard H.; Noble, Bernice; Comeau, Robin L.; Neiders, Mirdza E.; "Phenotypic Characterization of Mononuclear Cells Following Anorganic Bovine Bone Implantation in Rats"; J Periodontol; bearing a date of Nov. 1994; pp. 1008-1015; vol. 65, No. 11.
Colleoni, S.; Donofrio, G.; Lagutina, I.; Duchi, R.; Galli, C.; Lazzari, G.; "Establishment, Differentiation, Electroporation, Viral Transduction, and Nuclear Transfer of Bovine and Porcine Mesenchymal Stem Cells"; Cloning and Stem Cells; bearing a date of Nov. 3, 2005; pp. 154-166; vol. 7, No. 3; Mary Ann Liebert, Inc.
Coomber, B. L.; Stewart, P. A.; "Morphometric Analysis of CNS Microvascular Endothelium"; Microvascular Research; Bearing a date of 1985; pp. 99-115; vol. 30; Academic Press.
Cozzi, Emanuele; Ancona, Ermanno; "Review: Xenotransplantation, where do we stand?"; Journal of Nephrology; bearing a date of 2003; pp. S16-S21; vol. 16, Suppl. No. 7; located at: http://www.sin-italy.org/jnonline/vol16%20suppl%207n/s16.html; printed on Feb. 22, 2006; pp. 1-9.
Crone, Christian; Christensen, Ove; "Electrical Resistance of a Capillary Endothelium"; The Journal of General Physiology; bearing a date of Apr. 1981; pp. 349-371; vol. 77, No. 4; The Rockefeller University Press.
Deans, Robert J.; Moseley, Annemarie B.; "Mesenchymal stem cells: Biology and potential clinical uses"; International Society for Experimental Hematology; bearing a date of 2000; pp. 875-884; vol. 28; Elsevier Science Inc.
De Boer, A.G.; Van Der Sandt, I.C.J.; Gaillard, P.J.; "The Role of Drug Transporters at the Blood-Brain Barrier"; Annual Review of Pharmacology and Toxicology; bearing a date of 2003; pp. 629-656; vol. 43; Annual Reviews.
Deeba, F.; Tahseen, Nasti; Sharad, K. Sharma; Ahmad, N.; Akhtar, S.; Saleemuddin, M.; Mohammad, O.; "Phospholipid diversity: Correlation with membrane-membrane fusion events"; Biochimica et Biophysica Acta 1669; bearing a date of 2005; pp. 170-181; Elsevier B.V.; located at: http://www.elsevier.com/locate/bba and at: www.sciencedirect.com.
Deli, Mária A.; Ábrahám, Csongor S.; Kataoka, Yasufumi; Niwa, Masami; "Permeability Studies on In Vitro Blood-Brain Barrier Models: Physiology, Pathology, and Pharmacology"; Cellular and Molecular Neurobiology; bearing a date of Feb. 2005; pp. 59-127; vol. 25, No. 1; Springer Science + Business Media, Inc.
Duport, S.; Robert, F.; Muller, D.; Grau, G.; Parisi, L.; Stoppini, L.; "An in vitro blood-brain barrier model: Cocultures between endothelial cells and organotypic brain slice cultures"; Proc. Natl. Acad. Sci. USA; bearing a date of Feb. 1998; pp. 1840-1845; vol. 95; The National Academy of Sciences.
D'Urso, P.S.; Earwaker, W.J.; Barker, T.M.; Redmond, M.J.; Thompson, R.G.; Effeney, D.J.; Tomlinson, F.H.; "Custom cranioplasty using stereolithography and acrylic"; British Journal of Plastic Surgery; bearing a date of 2000; pp. 200-204; vol. 53; The British Association of Plastic Surgeons.
Emerich, Dwaine F.; Salzberg, Heather C.; "Review: Update on Immunoisolation Cell Therapy for CNS Diseases"; Cell Transplantation; bearing a date of 2001; pp. 3-24; vol. 10; Cognizant Comm. Corp.
Ewers, Rolf; Goriwoda, Walter; Schopper, Christian; Moser, Doris; Spassova, Else; "Histologic findings at augmented bone areas supplied with two different bone substitute materials combined with sinus floor lifting"; Clin. Oral Impl. Res.; bearing a date of 2004; pp. 96-100; vol. 15; Blackwell Munksgaard.
Farrell, Catherine L.; Pardridge, William M.; "Neurobiology: Blood-brain Barrier Glucose Transporter is Asymmetrically Distributed on Brain Capillary Endothelial Lumenal and Ablumenal Membranes: An Electron Microscopic Immunogold Study"; Proc. Natl. Acad. Sci. USA; bearing a date of Jul. 1991; pp. 5779-5783; vol. 88, No. 13.
Folwarczna, Joanna; Sliwinski, Leszek; Janiec, Waldemar; Pikul, Malgorzata; "Effects of standard heparin and low-molecular-weight heparins on the formation of murine osteoclasts in vitro"; Pharmacological Reports; bearing a date of 2005; pp. 635-645; vol. 57; Institute of Pharmacology Polish Academy of Sciences.
Furuse, Mikio; Sasaki, Hiroyuki; Tsukita, Shoichiro; "Manner of Interaction of Heterogeneous Claudin Species Within and Between Tight Junction Strands"; The Journal of Cell Biology; bearing a date of Nov. 15, 1999; pp. 891-903; vol. 147, No. 4; The Rockefeller University Press.
Gamradt, Seth C.; Lieberman, Jay R.; "Genetic Modification of Stem Cells to Enhance Bone Repair"; Annals of Biomedical Engineering; bearing a date of Jan. 2004; pp. 136-147; vol. 32, No. 1; Biomedical Engineering Society.

(56) References Cited

OTHER PUBLICATIONS

Gao, Bo; Meier, Peter J.; "Organic Anion Transport Across the Choroid Plexus"; Microscopy Research and Technique; bearing a date of 2001; pp. 60-64; vol. 52; Wiley-Liss, Inc.

Glowacki, Julie; "Review: A review of osteoinductive testing methods and sterilization processes for demineralized bone"; Cell and Tissue Banking; bearing a date of 2005; pp. 3-12; vol. 6; Springer.

Graham, Sarah; "High-Res Images Expose Bone's 'Glue'"; Science News; bearing a date of Jul. 20, 2005, pp. 1-2.

Griffith, Linda G.; "Emerging Design Principles in Biomaterials and Scaffolds for Tissue Engineering"; Annals New York Academy of Sciences; bearing a date of 2002; pp. 83-95; vol. 961; New York Academy of Sciences.

Hanks, Tracey; Atkinson, Brent Lee; "Comparison of cell viability on anorganic bone matrix with or without P-15 cell binding peptide"; Biomaterials; bearing a date of 2004; pp. 4831-4836; vol. 25; Elsevier Ltd.; located at: www.elsevier.com/locate/biomaterials and www.sciencedirect.com.

Haskins, Julie; Gu, Lijie; Wittchen, Erika S.; Hibbard, Jennifer; Stevenson, Bruce R.; "ZO-3, a Novel Member of the MAGUK Protein Family Found at the Tight Junction, Interacts with ZO-1 and Occludin"; The Journal of Cell Biology; bearing a date of Apr. 6, 1998; pp. 199-208; vol. 141, No. 1; The Rockefeller University Press.

Haynesworth, S.E.; Goshima, J.; Goldberg, V.M.; Caplan, A.I.; "Characterization of Cells with Osteogenic Potential from Human Marrow"; Bone; bearing a date of 1992; pp. 81-88; vol. 13; Pergamon Press plc.

Hernandez, L.D.; Hoffman, L.R.; Wolfsberg, T.G.; White, J.M.; "Virus-Cell and Cell-Cell Fusion"; Annu. Rev. Cell Dev. Biol.; bearing a date of 1996; pp. 627-661; vol. 12.

Hole, Bhushan B.; Schwarz, James A.; Gilbert, Jeremy L.; Atkinson, Brent L.; "A study of biologically active peptide sequences (P-15) on the surface of an ABM scaffold (PepGen P-15™) using AFM and FTIR"; J Biomed Mater Res; bearing a date of Jul. 14, 2005; pp. 712-721; vol. 74A; Wiley Periodicals, Inc.; located at www.interscience.wiley.com.

Holy, Chantal E.; Shoichet, Molly S.; Davies, John E.; "Engineering three-dimensional bone tissue in vitro using biodegradable scaffolds: Investigating initial cell-seeding density and culture period"; J. Biomed Mater Res; bearing a date of 2000; pp. 376-382; vol. 51; John Wiley & Sons, Inc.

Horwitz, Edwin M.; Gordon, Patricia L.; Koo, Winston K.K.; Marx, Jeffrey C.; Neel, Michael D.; McNall, Rene Y.; Muul, Linda; Hofmann, Ted; "Isolated allogeneic bone marrow-derived mesenchymal cells engraft and stimulate growth in children with osteogenesis imperfecta: Implications for cell therapy of bone"; PNAS; bearing a date of Jun. 25, 2002; pp. 8932-8937; vol. 99, No. 13; located at: www.pnas.org/cgi/doi/10.1073/pnas.132252399.

Hosoya, Ken-Ichi; Hori, Satoko; Ohtsuki, Sumio; Terasaki, Tetsuya; "A new in vitro model for blood-cerebrospinal fluid barrier transport studies: an immortalized choroid plexus epithelial cell line derived from the tsA58 SV40 large T-antigen gene transgenic rat"; Advanced Drug Delivery Reviews; bearing a date of 2004; pp. 1875-1885; vol. 56; Elsevier B.V.

Hutmacher, Dietmar W.; Garcia, Andres J.; "Scaffold-based bone engineering by using genetically modified cells"; Gene: Section Functional Genomics; bearing a date of 2005; pp. 1-10; vol. 347; Elsevier B.V.; located at: www.elsevier.com/locate/gene and www.sciencedirect.com.

Ishaug-Riley, Susan L.; Crane-Kruger, Genevieve M.; Yaszemski, Michael J.; Mikos, Antonios G.; "Three-dimensional culture of rat calvarial osteoblasts in porous biodegradable polymers"; Biomaterials; bearing a date of 1998; pp. 1405-1412; vol. 19; Elsevier Science Ltd.

Iwata, Hiroo; Takagi, Tatsuya; Amemiya, Hiroshi; Shimizu, Hiroshi; Yamashita, Kazuya; Kobayashi, Kazuo; Akutsu, Tetsuzo; "Agarose for a bioartificial pancreas"; Journal of Biomedical Materials Research; bearing a date of 1992; pp. 967-977; vol. 26; John Wiley & Sons, Inc.

Iwata, Hiroo; Murakami, Yoshinobu; Ikada, Yoshito; "Control of Complement Activities for Immunoisolation"; Annals New York Academy of Sciences; bearing a date of 1999; pp. 7-23.

Janáček, K.; Sigler, K.; "Minireview- Osmosis: Membranes Impermeable and Permeable for Solutes, Mechanism of Osmosis across Porous Membranes"; Physiological Research; bearing a date of 2000; pp. 191-195; vol. 49; Institute of Physiology, Academy of Sciences of the Czech Republic, Prague, Czech Republic.

Janigro, D.; Strelow, L.; Grant, G.; Nelson, J.A.; "In vitro blood-brain barrier model for HIV-induced CNS disease"; NeuroAIDS; bearing a date of Aug. 1998; pp. 1-6; vol. 1, No. 4; The American Association for the Advancement of Science; located at: http://www.aidscience.org/neuroaids/Articles/Neuro1(4).htm.

Johanson, Conrad E.; Duncan, John A.; Stopa, Edward G.; Baird, Andrew; "Enhanced Prospects for Drug Delivery and Brain Targeting by the Choroid Plexus-CSF Route"; Pharmaceutical Research; bearing a date of Jul. 2005; pp. 1011-1037; vol. 22, No. 7; Springer Science + Business Media, Inc.

Josserand, Véronique; Pélerin, Héléne; De Bruin, Béatrice; Jego, Benôit; Kuhnast, Bertrand; Hinnen, Francoise; Ducongé, Frédéric; Boisgard, Raphael; Beuvon, Frédéric; Chassoux, Francine; Daumas-Duport, Catherine; Ezan, Eric; Dollé, Frédéric; Mabondzo, Aloïse; Tavitian, Bertrand; "Evaluation of Drug Penetration into the Brain: A Double Study by in Vivo Imaging with Positron Emission Tomography and Using an in Vitro Model of the Human Blood-Brain Barrier"; The Journal of Pharmacology and Experimental Therapeutics; bearing a date of 2006; pp. 79-86; vol. 316, No. 1; The American Society for Pharmacology and Experimental Therapeutics.

Kamohara, Yukio; Rozga, Jacek; Demetriou, Achilles A.; "Review Article—Artificial liver: Review and Cedars-Sinai experience"; Journal of Hepatobiliary Pancreat Surg; bearing a date of 1998; pp. 273-285; vol. 5; Springer-Verlag.

Karageorgiou, Vassilis; Kaplan, David; "Porosity of 3D biomaterial scaffolds and osteogenesis"; Biomaterials; bearing a date of 2005; pp. 5474-5491; vol. 26; Elsevier Ltd; located at: www.elseiver.com/locate/biomaterials and at: www.sciencedirect.com.

Kassem, Moustapha; Kristiansen, Malthe; Abdallah, Basem M.; "MiniReview—Mesenchymal Stem Cells: Cell Biology and Potential Use in Therapy"; Pharmacology & Toxicology; bearing a date of 2004; pp. 209-214; vol. 95; Basic & Clinical Pharmacology & Toxicology.

Kawamoto, Tadafumi; Shimizu, Masaharu; "A method for preparing 2- to 50-pm-thick fresh-frozen sections of large samples and undecalcified hard tissues"; Histochem Cell Biol; bearing a date of 2000; pp. 331-339; vol. 113; Springer-Verlag.

Kemp, Kevin C.; Hows, Jill; Donaldson, Craig; "Bone marrow-derived mesenchymal stem cells"; Leukemia & Lymphoma; bearing a date of 2005; pp. 1531-1544; vol. 46, No. 11; Taylor & Francis.

Khakbaznejad, A.; Chehroudi, B.; Brunette, D.M.; "Effects of titanium-coated micromachined grooved substrata on orienting layers of osteoblasts-like cells and collagen fibers in culture"; J Biomed Mater Res; bearing a date of 2004; pp. 206-218; vol. 70A; Wiley Periodicals, Inc.; located at: www.interscience.wiley.com.

Koç, On; Day J.; Nieder, M.; Gerson, S.L.; Lazarus, H.M.; Krivit, W.; "Mesenchymal stem cells: Allogeneic mesenchymal stem cell infusion for treatment of metachromatic leukodystrophy (MLD) and Hurler syndrome (MPS-IH)"; Bone Marrow Transplantation; bearing a date of 2002; pp. 215-222; vol. 30; Nature Publishing Group.

Kumar, Sanjay; Mahendra, Gandham; Ponnazhagan, Selvarangan; "Determination of osteoprogenitor-specific promoter activity in mouse mesenchymal stem cells by recombinant adeno-associated virus transduction"; Biochimica et Biophysica Acta; bearing a date of 2005; pp. 95-103; vol. 1731; Elsevier B.V.; located at: http://www.elsevier.com/locate/bba and at: www.sciencedirect.com.

Lacy, Paul E.; Hegre, Orion D.; Gerasimidi-Vazeou, Andrjani; Gentile, Frank T.; Dionne, Keith E.; "Maintenance of Normoglycemia in Diabetic Mice by Subcutaneous Xenografts of Encapsulated Islets"; Science; bearing a date of Dec. 20, 1991; pp. 1782-1784; vol. 254.

Lai, Char-Huei; Kuo, Kuo-Hsing; "The critical component to establish in vitro BBB model: Pericyte"; Brain Research Reviews; bearing a date of 2005; pp. 258-265; vol. 50; Elsevier B.V.

Landers, Rüdiger; Hübner, Ute; Schmelzeisen, Rainer; Mülhaupt, Rolf; "Rapid prototyping of scaffolds derived from thermoreversible

(56) References Cited

OTHER PUBLICATIONS hydrogels and tailored for applications in tissue engineering"; Biomaterials; bearing a date of 2002; pp. 4437-4447; vol. 23; Elsevier Science Ltd.; located at: www.elsevier.com/locate/biomaterials.

Larson, Gretchen; Pieterse, Anton; Quick, Gwynnèth; Van Der Bijl, Pieter; Van Zyl, Johann; Hawtrey, Arthur; "Development of a Reproducible Procedure for Plasmid DNA Encapsulation by Red Blood Cell Ghosts"; Biodrugs; bearing a date of 2004; pp. 189-198; vol. 18, No. 3; Adis Data Information.

Lau, Wai Leung; Ege, David S.; Lear, James D.; Hammer, Daniel A.; Degrado, William F.; "Oligomerization of Fusogenic Peptides Promotes Membrane Fusion by Enhancing Membrane Destabilization"; Biophysical Journal; bearing a dates of Jan. 2004; pp. 272-284; vol. 86, No. 1; Biophysical Society.

Laurencin, Cato T. MD, PhD.; Khan, Yusuf, BA, MS; "Bone Graft Substitute Materials"; eMedicine; bearing a date of Feb. 1, 2006; pp. 1-8; Sections 1-11; eMedicine.com, Inc.

Leary Swan, Erin E.; Popat, Ketul C.; Grimes, Craig A.; Desai, Tejal A.; "Fabrication and evaluation of nanoporous alumina membranes for osteoblast culture"; J. Biomed Mater Res; bearing a date of 2005; pp. 288-295; vol. 72A; Wiley Periodicals, Inc.

Le Blanc, Katarina; Tammik, Charlotte; Rosendahl, Kerstin; Zetterberg, Eva; Ringdén, Olle; "HLA expression and immunologic properties of differentiated and undifferentiated mesenchymal stem cells"; Experimental Hematology; bearing a date of 2003; pp. 890-896; vol. 31; Elsevier, Inc.

Le Blanc, Katarina; Rasmusson, Ida; Sundberg, Berit; Götherström, Cecilia; Hassan, Moustapha; Uzunel, Mehmet; Ringdén, Olle; "Research letters: Treatment of severe acute graft-versus-host disease with third party haploidentical mesenchymal stem cells"; The Lancet; bearing a date of May 1, 2004; pp. 1439-1441; vol. 363.

Lin, Chia-Ying, Ph.D.; Schek, Rachel M., Ph.D.; Mistry, Amit S., B.S.; Shi, Xinfeng, M.S.; Mikos, Antonios, G., Ph.D.; Krebsbach, Paul H., D.D.S., Ph.D.; Hollister, Scott, J., Ph.D.; "Functional Bone Engineering Using ex Vivo Gene Therapy and Topology-Optimized, Biodegradable Polymer Composite Scaffolds"; Tissue Engineering; bearing a date of 2005; pp. 1589-1598; vol. 11, No. 9/10; Mary Ann Liebert, Inc.

Maki, Takashi; Otsu, Ichiro; O'Neil, John J.; Dunleavy, Karen; Mullon, Claudy, J.P.; Solomon, Barry A.; Monaco, Anthony P.; "Treatment of Diabetes by Xenogeneic Islets Without Immunosuppression: Use of a Vascularized Bioartificial Pancreas"; Diabetes; bearing a date of Mar. 1996; pp. 342-347; vol. 45.

Marx, Jean; "Piecing Together Human Aging: Coming to Grips With Bone Loss"; Science; bearing a date of Sep. 3, 2004; pp. 1420-1422; vol. 305; AAAS; located at: www.sciencemag.org.

Matter, Karl; Balda, Maria S.; "Functional analysis of tight junctions"; Methods; bearing a date of 2003; pp. 228-234; vol. 30; Elsevier Science; located at: www.elsevier.com/locate/ymeth and at: www.sciencedirect.com.

Meyer, U.; Joos, U.; Wiesmann, H.P.; "Biological and biophysical principles in extracorporal bone tissue engineering—Part 1"; International Journal of Oral & Maxillofacial Surgery; bearing a date of 2004; pp. 325-332; vol. 33; Elsevier Ltd.

Michejda, Maria; "Which Stem Cells Should be Used for Transplantation?"; Fetal Diagnosis and Therapy; bearing a date of 2004; pp. 2-8; vol. 19; S. Karger Medical and Scientific; located at: www.karger.com/fdt.

Minn, Alain; Ghersi-Egea, Jean-Francois; Perrin, Rachel; Leininger, Brigitte; Siest, Gérard; "Drug Metabolizing Enzymes in the Brain and Cerebral Microvessels"; Brain Research Reviews; Bearing a date of 1991; pp. 65-82; vol. 16; Elsevier Science Publishers B. V.

Mishra, P.R.; Jain, N.K.; "Folate Conjugated Doxorubicin-Loaded Membrane Vesicles for Improved Cancer Therapy"; Drug Delivery; bearing a date of 2003; pp. 277-282; vol. 10; Taylor & Francis Inc.

Mohan, Subburaman, Ph.D.; Baylink, David J., M.D.; "Bone Growth Factors"; Clinical Orthopaedics and Related Research; bearing a date of Feb. 1991; pp. 30-48; vol. 263.

Moon, Seong-Hwan, MD; Park, Seung-Rim, MD; Kim, Hyang, MSc; Kwon, Un-Hye, BSc; Kim, Keong-Hee, BSc; Kim, Hak-Sun, MD; Lee, Hwan-Mo, MD; "Biologic Modification of Ligamentum Flavum Cells by Marker Gene Transfer and Recombinant Human Bone Morphogenetic Protein-2"; Spine; bearing a date of 2004; pp. 960-965; vol. 29, No. 9; Lippincott Williams & Wilkins, Inc.

Müller, Rainer, H.; Mäder, Karsten; Gohla, Sven; "Review article-Solid lipid nanoparticles (SLN) for controlled drug delivery—a review of the state of the art"; European Journal of Pharmaceutics and Biopharmaceutics; bearing a date of 2000; pp. 161-177; vol. 50; Elsevier Science B.V.

Mundy, Gregory R.; "Cytokines and Growth Factors in the Regulation of Bone Remodeling"; Journal of Bone and Mineral Research; bearing a date of 1993; pp. S505-S510; vol. 8, Supplement 2; Mary Ann Liebert, Inc.

Muraglia, Anita; Cancedda, Ranieri; Quarto, Rodolfo; "Clonal mesenchymal progenitors from human bone marrow differentiate in vitro according to a hierarchical model"; Journal of Cell Science; bearing a date of 2000; pp. 1161-1166; vol. 113; The Company of Biologists Limited.

Nagy, Zoltán; Vastag, Mónika; Kolev, Krasimir; Bori, Zoltán; Karádi, István; Skopál, Judit; "Human Cerebral Microvessel Endothelial Cell Culture as a Model System to Study the Blood-Brain Interface in Ischemic/Hypoxic Conditions"; Cellular and Molecular Neurobiology; bearing a date of Feb. 2005; pp. 201-210; vol. 25, No. 1; Springer Science + Business Media, Inc.

Nierodzik, M.L.; Plotkin, A.; Kajumo, F.; Karpatkin, S.; "Thrombin Stimulates Tumor-Platelet Adhesion In Vitro and Metastasis In Vivo"; J. Clin. Invest.; bearing a date of Jan. 1991; pp. 229-236; vol. 87; The American Society for Clinical Investigation, Inc.

Nusrat, A.; Parkos, C.A.; Verkade, P.; Foley, C.S.; Liang, T.W.; Innis-Whitehouse, W.; Eastburn, K.K.; Madara, J.L.; "Tight Junctions are Membrane Microdomains"; Journal of Cell Science; bearing a date of 2000; pp. 1771-1781; vol. 113; The Company of Biologists Limited.

O'Donoghue, Keelin, MB, Mrcog; Fisk, Nicholas M., PhD, FRCOG; "Fetal stem cells"; Best Practice & Research Clinical Obstetrics and Gynaecology; bearing a date of 2004; pp. 853-875; vol. 18, No. 6; Elsevier Ltd; located at: http://www.sciencedirect.com.

Ohgawara, Hisako; "Strategies for immunoisolation in islet transplantation: challenges for the twenty-first century"; J Hepatobiliary Pancreat Surg; bearing a date of 2000; pp. 374-379; vol. 7; Springer-Verlag.

Oldendorf, William H.; Brown, W. Jann; "Greater Number of Capillary Endothelial Cell Mitochondria in Brain Than in Muscle (38889)"; Proceedings of the Society for Experimental Biology and Medicine; Bearing a date of 1975; pp. 736-738; vol. 149; Society for Experimental Biology and Medicine.

Oldendorf, William H., M.D.; Cornford, Marcia E., Ph.D.; Brown, W. Jann, M.D.; "The Large Apparent Work Capability of the Blood-Brain Barrier: A Study of the Mitochondrial Content of Capillary Endothelial Cells in Brain and Other Tissues of the Rat"; Annals of Neurology; bearing a date of May 1977; pp. 409-417; vol. 1, No. 5.

Perizzolo, D.; Lacefield, W.R.; Brunette, D.M.; "Interaction between topography and coating in the formation of bone nodules in culture for hydroxyapatite-and titanium-coated micromachined surfaces"; J Biomed Mater Res; bearing a date of 2001; pp. 494-503; vol. 56; John Wiley & Sons, Inc.

Pittenger, Mark F.; Mackay, Alastair M.; Beck, Stephen C.; Jaiswal, Rama K.; Douglas, Robin; Mosca, Joseph D.; Moorman, Mark A.; Simonetti, Donald W.; Craig, Stewart; Marshak, Daniel, R.; "Reports: Multilineage Potential of Adult Human Mesenchymal Stem Cells"; Science; bearing a date of Apr. 2, 1999; pp. 143-147; vol. 284; located at: www.sciencemag.org.

Prieto, Pilar; Blaauboer, Bas J.; De Boer, Albertus Gerrit; Boveri, Monica; Cecchelli, Romeo; Clemedson, Cecilia; Coecke, Sandra; Forsby, Anna; Galla, Hans-Joachim; Garberg, Per; Greenwood, John; Price, Anna; Tähti, Hanna; "The Report and Recommendations of ECVAM Workshop 49: Blood-Brain Barrier In Vitro Models and Their Application in Toxicology"; Alternatives to Laboratory Animals; bearing a date of 2004; pp. 37-50; vol. 32, No. 1; ECVAM, Institute for Health & Consumer Protection, European Commission Joint Research Centre.

(56) References Cited

OTHER PUBLICATIONS

Pulanić, Drž; Rudan, Igor; "The Past Decade: Fibrinogen"; Coll. Antropol.; bearing a date of 2005; pp. 341-349; vol. 29, No. 1.

Rao, Vallabhaneni V.; Dahlheimer, Julie L.; Bardgett, Mark E.; Snyder, Abraham Z.; Finch, Rick A.; Sartorelli, Alan C.; Piwnica-Worms, David; "Medical Sciences: Choroid plexus epithelial expression of MDR1 P glycoprotein and blood-cerebrospinal-fluid drug-permeability barrier"; Proc. Natl. Acad. Sci. USA; bearing a date of Mar. 1999; pp. 3900-3905; vol. 96.

Rensberger, John, M.; Watabe, Mahito; "letters to nature: Fine structure of bone in dinosaurs, birds and mammals"; Nature; bearing a date of Aug. 10, 2000; pp. 619-622; vol. 406; Macmillan Magazines Ltd.; located at: www.nature.com.

Reszka, Alfred A., PhD; Rodan, Gideon A., MD, PhD; "Mechanism of Action of Bisphosphonates"; Current Osteoporosis Reports; bearing a date of 2003; pp. 45-52; vol. 1; Current Science Inc.

Roodman, G. David; "Role of Cytokines in the Regulation of Bone Resorption"; Calcified Tissue International; bearing a date of 1993; pp. S94-S98; vol. 53 (Suppl. 1); Springer-Verlag New York Inc.

Rossi, Luigia; Serafini, Sonja; Pierigé, Francesca; Antonelli, Antonella; Cerasi, Aurora; Fraternale, Alessandra; Chiarantini, Laura; Magnani, Mauro; "Review: Erythrocyte-based drug delivery"; Expert Opinion on Drug Delivery; bearing a date of 2005; pp. 311-322; vol. 2, No. 2; Ashley Publications; located at: www.ashelypub.com.

Runte, Christoph; Dirksen, Dieter; Deleré, Holger; Thomas, Carsten; Runte, Bettina; Meyer, Ulrich; Von Bally, Gert; Bollmann, Friedhelm; "Optical Data Acquisition for Computer-Assisted Design of Facial Prostheses"; The International Journal of Prosthodontics; bearing a date of Mar./Apr. 2002; pp. 129-132; vol. 15, No. 2.

Scaglione, S.; Braccini, A.; Wendt, D.; Jaquiery, C.; Beltrame, F.; Quarto, R.; Martin, Ivan; "Engineering of Osteoinductive Grafts by Isolation and Expansion of Ovine Bone Marrow Stromal Cells Directly on 3D Cermaic Scaffolds"; Biotechnology and Bioengineering; bearing a date of Jan. 5, 2005; pp. 181-187; vol. 93, No. 1; Wiley Periodicals, Inc.

Schantz, Jan-Thorsten; Brandwood, Arthur; Werner Hutmacher, Dietmar; Khor, Hwei Ling; Bittner, Katharina; "Osteogenic differentiation of mesenchymal progenitor cells in computer designed fibrin-polymer-ceramic scaffolds manufactured by fused deposition modeling"; Journal of Materials Science: Materials in Medicine; bearing a date of 2005; pp. 807-819; vol. 16; Springer Science + Business Media, Inc.

Schett, Georg; Haver, Silvia; Zwerina, Jochen; Redlich, Kurt; Smolen, Josef S; "Review: Mechanisms of Disease: the link between RANKL and arthritic bone disease"; Nature Clinical Practice: Rheumatology; bearing dates of Nov. 2005; pp. 47-54; vol. 1, No. 1; Nature Publishing Group; located at: www.nature.com/clinicalpractice/rheum.

Schneeberger, Eveline E., M.D.; Karnovsky, Morris J., M.B., B.Ch.; "Substructure of Intercellular Junctions in Freeze-Fractured Alveolar-Capillary Membranes of Mouse Lung" Circulation Research; bearing a date of May 1976; pp. 404-411; vol. 38, No. 5; American Heart Association; located at: http//circres.ahajournals.org.

Schweitzer, Mary H.; Wittmeyer, Jennifer L.; Horner, John R.; Gender-Specific Reproductive Tissue in Ratites and *Tyrannosaurus rex*; Science; bearing a date of Jun. 3, 2005; pp. 1456-1460; vol. 308; located at: www.sciencemag.org.

Schweitzer, Mary H.; Wittmeyer, Jennifer L.; Horner, John R.; Toporski, Jan K.; "Soft-Tissue Vessels and Cellular Preservation in *Tyrannosaurus rex*"; Science; bearing a date of Mar. 25, 2005; pp. 1952-1955; vol. 307; located at: www.sciencemag.org.

Smith, Quentin R.; Rapoport, Stanley I.; "Cerebrovascular Permeability Coefficients to Sodium, Potassium, and Chloride"; Journal of Neurochemistry; Bearing a date of 1986; pp. 1732-1742; International Society for Neurochemistry.

Spector, Myron, PhD; "Bone Repair and Regeneration: Anorganic Bovine Bone and Ceramic Analogs of Bone Mineral as Implants to Facilitate Bone Regeneration"; Clinics in Plastic Surgery—An International Quarterly; bearing a date of Jul. 1944; pp. 437-444; vol. 21, No. 3; W.B. Saunders Company.

Stevens, Molly, M.; George, Julian H.; "Materials and Biology—Review: Exploring and Engineering the Cell Surface Interface"; Science; bearing at date of Nov. 18, 2005; pp. 1135-1138; vol. 310; located at www.sciencemag.org.

Sun, Yilu; Ma, Xiaojun; Zhou, Daobiao; Vacek, Ivan; Sun, Anthony M.; "Bioartificial Pancreas: Normalization of Diabetes in Spontaneously Diabetic Cynomologus Monkeys by Xenografts of Microencapsulated Porcine Islets without Immunosuppression"; J. Clin. Invest.; bearing a date of Sep. 1996; pp. 1417-1422; vol. 98, No. 6; The American Society for Clinical Investigation, Inc.

Terasaki, Tetsuya; Hosoya, Ken-Ichi; "Conditionally Immortalized Cell Lines as a New In Vitro Model for the Study of Barrier Functions"; Biological & Pharmaceutical Bulletin; bearing a date of 2001; pp. 111-118; vol. 24, No. 2; Pharmaceutical Society of Japan.

Thorwarth, Michael; Schultze-Mosgau, Stefan; Wehrhan, Falk; Kessler, Peter; Srour, Safwan; Wiltfang, Jörg; Schlegel, Karl Andreas; "Bioactivation of an anorganic bone matrix by P-15 peptide for the promotion of early bone formation"; Biomaterials; bearing a date of 2005; pp. 5648-5657; vol. 26; Elsevier Ltd.; located at: www.sciencedirect.com and at: www.elsevier.com/locate/biomaterials.

Tse, William T.; Pendleton, John D; Beyer, Wendy M.; Egalka, Matthew C.; Guinan, Eva C.; "Suppression of Allogeneic T-Cell Proliferation by Human Marrow Stromal Cells: Implications in Transplantation"; Transplantation; bearing a date of Feb. 15, 2003; pp. 389-397; vol. 75, No. 3; Lippincott Williams & Wilkins, Inc.

Tsukita, Shoichiro; Furuse, Mikio; "Occludin and Claudins in Tight-Junction Strands: Leading or Supporting Players?"; Trends in Cell Biology; bearing a date of 1999; pp. 268-273; vol. 9, No. 7; Elsevier Science.

Turner, C.H.; "Review Article: Biomechanics of Bone: Determinants of Skeletal Fragility and Bone Quality"; Osteoporos International; bearing a date of 2002; pp. 97-104; vol. 13; International Osteoporosis Foundation and National Osteoporosis Foundation.

Vacanti, C.A., M.D.; Kim, W., M.D.; Upton, J., M.D.; Mooney, D., Ph.D.; Vacanti, J.P., M.D.; "The Efficacy of Periosteal Cells Compared to Chondrocytes in the Tissue Engineered Repair of Bone Defects"; Tissue Engineering; bearing a date of 1995; pp. 301-308; vol. 1, No. 3; Mary Ann Liebert, Inc.

Valentini, Pascal, DDS; Abensur, David J., DDS; Maxillary Sinus Grafting with Anorganic Bovine Bone: A Clinical Report of Long-term Results; The International Journal of Oral & Maxillofacial Implants; bearing a date of 2003; pp. 556-560; vol. 18, No. 4; Quintessence Publishing Co., Inc.

Warren, Stephen M., MD; Nacamuli, Randall, P., MD; Song, Hanjoon M., MD; Longaker, Michael T., MD, FACS; "Discussion: Tissue-Engineered Bone Using Mesenchymal Stem Cells and a Biodegradable Scaffold"; The Journal of Craniofacial Surgery; bearing a date of Mar. 2002; pp. 240-243; vol. 13, No. 2; Mutaz Habal, MD.

Widmer, Markus S.; Mikos, Antonios G.; "Chapter 11.5 Fundamentals and Methods of Tissue Engineering: Fabrication of Biodegradable Polymer Scaffolds for Tissue Engineering"; Frontiers in Tissue Engineering; bearing a date of 1998; pp. 107-120; Elsevier Science Ltd.

Wiedmann-Al-Ahmad, M.; Gutwald, R.; Gellrich, N.-C.; Hübner, U.; Schmelzeisen, R.; "Search for ideal biomaterials to cultivate human osteoblast-like cells for reconstructive surgery"; Journal of Materials Science: Materials in Medicine; bearing a date of 2005; pp. 57-66; vol. 16; Springer Science + Business Media, Inc.

Wiesmann, H.P.; Joos, U.; Meyer, U.; "Biological and biophysical principles in extracorporal bone tissue engineering—Part II"; International Journal of Oral & Maxillofacial Surgery; bearing a date of 2004; pp. 523-530; vol. 33; Elsevier Ltd.; located at: http://www.sciencedirect.com.

Xin, Zhao-Liang; Ge, Song-Lin; Wu, Xiao-Kang; Jia, Yan-Jie; Hu, Han-Tao; "Intracerebral xenotransplantation of semipermeable membrane-encapsuled pancreatic islets"; World Journal of Gastroenterology; bearing a date of 2005; pp. 5714-5717; vol. 11, No. 36; The WJG Press and Elsevier Inc.

Xu, Hockin H.K.; Takagi, Shozo; Quinn, Janet B.; Chow, Laurence C.; "Fast-setting calcium phosphate scaffolds with tailored

(56) References Cited

OTHER PUBLICATIONS macropore formation rates for bone regeneration"; J Biomed Mater Res; bearing a date of 2004; pp. 725-734; vol. 68A; Wiley Periodicals, Inc.

Yoshikawa, Hideki, MD, PhD; Myoui, Akira, MD, PhD; "Review: Bone Tissue engineering with porous hydroxyapatite ceramics"; J Artif Organs; bearing a date of 2005; pp. 131-136; vol. 8; The Japanese Society for Artificial Organs.

Zavazava, Nicholas; "Review: Cell- & Tissue-based Therapy: Embryonic stem cells and potency to induce transplantation tolerance"; Expert Opin. Biol. Ther.; bearing a date of 2003; pp. 5-13; vol. 3, No. 1; Ashley Publications; located at: www.ashley-pub.com.

* cited by examiner

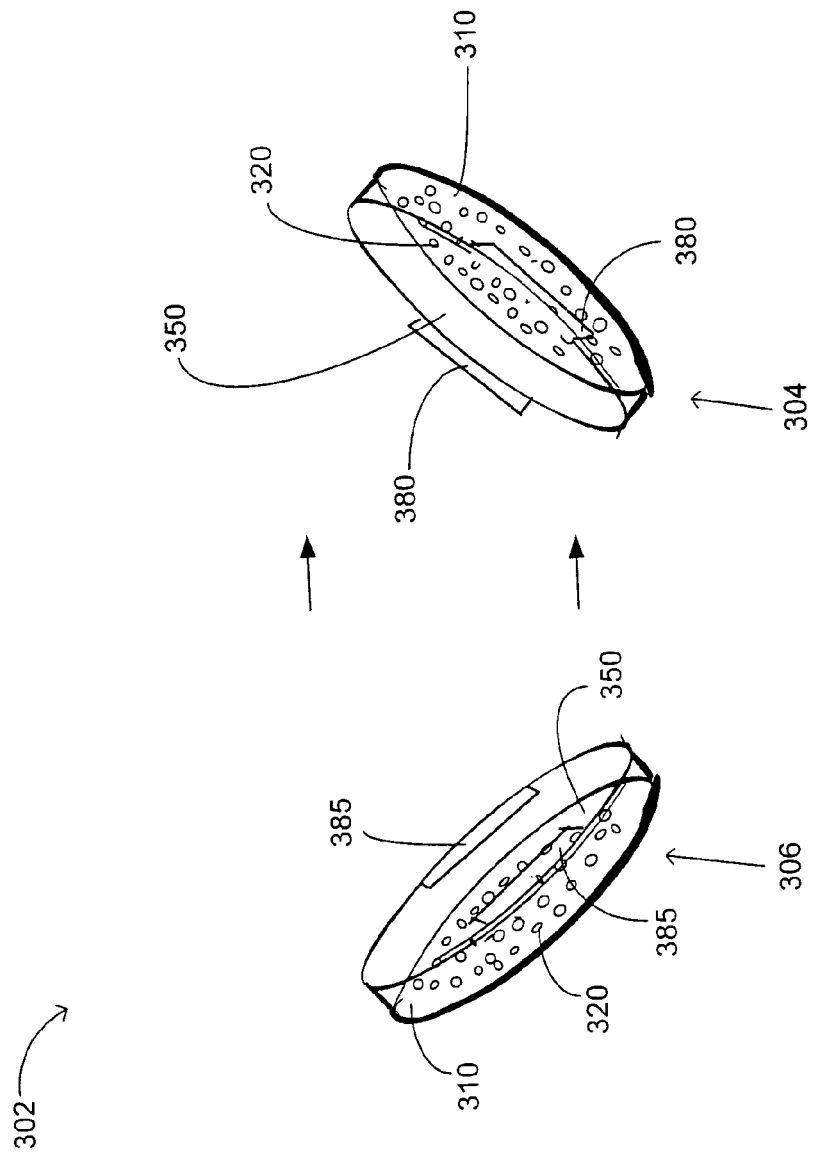

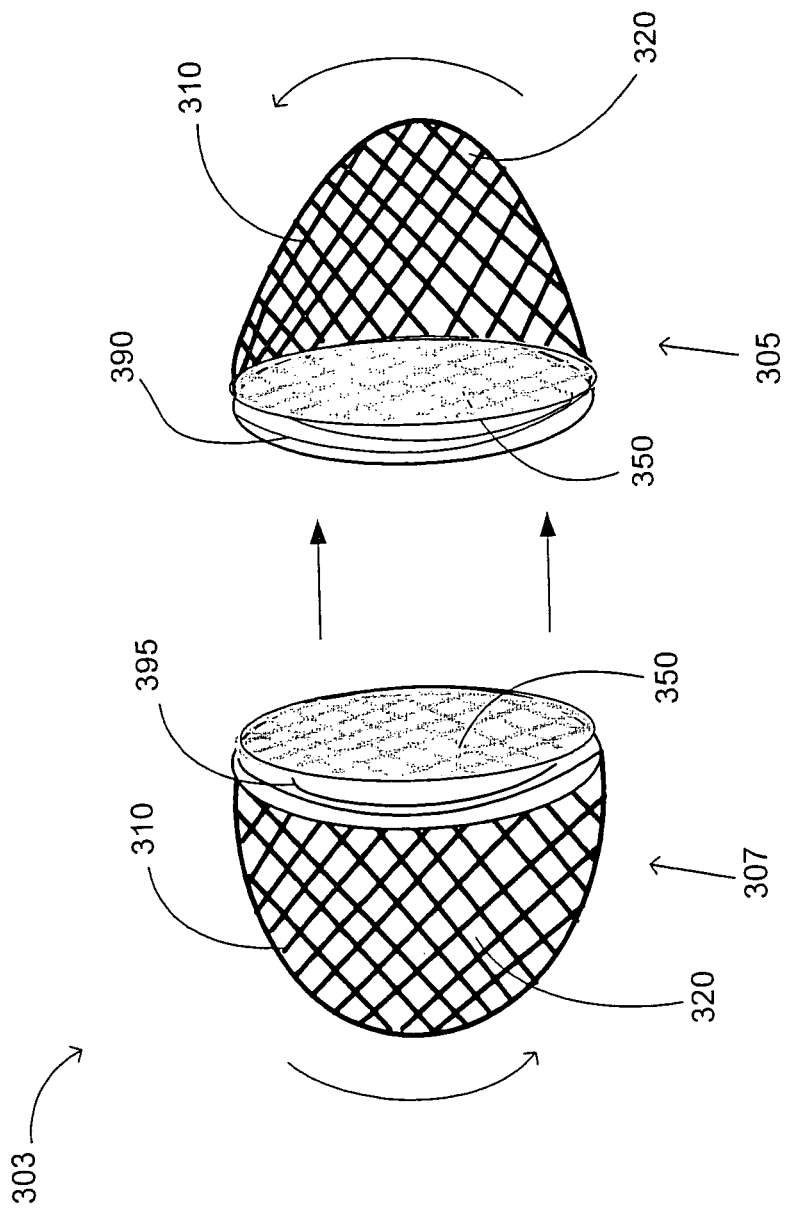

FIG. 4A

DISORDERS OF AMINO ACID METABOLISM

401

| Disease | Defective Enzyme or System | Symptoms | Treatment |
|---|---|---|---|
| Phenylketonuria (PKU) | phenylalanine hydroxylase | severe mental retardation | screening; dietary modification |
| Malignant PKU | biopterin cofactor | neurological disorder | |
| Type 1 tyrosinemia | fumarylacetoacetate hydrolase | nerve damage, pain, liver failure | liver transplantation; preceding enzyme inhibitor plus dietary modification |
| Type 2 tyrosinemia | tyrosine aminotransferase | irritation to the corneas of the eyes | diet with reduced phenylalanine and tyrosine content |
| Alkaptonuria | disorder of tyrosine breakdown | progressive arthritis and bone disease; dark urine | |
| Homocystinuria and Hyperhomocysteinemia | cystathionine-β- synthase or methylenetetrahydrofolate reductase or various deficiencies in formation of the methylocobalamin form of vitamin B12 | hypercoagulability of the blood; vascular eposides; dislocation of the lens of the eye, elongation and thinning of the bones, and often mental retardation or psychiatric abnormalities | Vitamin B12, folic acid, betaine, a diet limited in cysteine and methionine |
| Maple Syrup Urine disease | branched-chain ketoacid dehydrogenase complex | elevations of branched-chain amino acids, characteristic odor of the urine, episodes of ketoacidosis, death | thiamine; careful regulation of dietary intake of the essential branched-chain amino acids |

DISORDERS OF ORGANIC ACID METABOLISM

| Disease | Defective Enzyme or System | Symptoms | Treatment |
|---|---|---|---|
| Propionic Acidemia | propionyl – CoA carboxylase | generalized metabolic dysfunction; ketoacidosis; death | diet with limited amounts of the amino acids which are precursors to propionyl - CoA |
| Multiple Carboxylase deficiency | pyruvate carboxylase and 3-methylcrotonyl-CoA carboxylase | | biotin |
| Methylmalonic Acidemia | methylmalonyl-CoA mutase; defects in the enzyme systems involved in vitamin B12 metabolism | | supplementation with large doses of vitamin B12; diet |

FIG. 4C

DISORDERS OF FATTY ACID METABOLISM

| Disease | Defective Enzyme or System | Symptoms | Treatment |
|---|---|---|---|
| Hyperlipidemia and hypercholesterolemia | regulation or utilization of lipoproteins | cardiovascular disease | dietary modifications and use of drugs that inhibit fatty acid synthesis |
| Fatty Acid Oxidation disorders | very long chain acyl-CoA dehydrogenase; long chain hydroxyacyl-CoA dehydrogenase; dehydrogenase; medium chain acyl-CoA dehydrogenase; short chain acyl CoA dehydrogenase; short chain hydroxyacyl-CoA dehydrogenase | low blood sugar (hypoglycemia); muscle weakness; cardiomyopathy | avoidance of fasting, intravenous glucose solutions; carnitine; medium chain triglycerides |
| Glycogen Storage diseases | defects in glycogenolysis | liver enlargement or damage; muscle weakening or breakdown; disturbed renal tubular function; risk of brain damage | |
| Galactosemia | galactose-1-phosphate uridyl transferase | liver failure in infancy | newborn screening; milk avoidance |
| Congenital Disorders of Glycosylation | defects in the enzymes that build the carbohydrate side-chains on proteins | quite variable; multisystem | |

FIG. 4D

DISORDERS OF PURINE AND PYRIMIDINE METABOLISM

404

| Disease | Defective Enzyme or System | Symptoms | Treatment |
|---|---|---|---|
| Purine Overproduction | imbalance between purine synthesis and disposal | gout | |
| Lesch-Nyhan syndrome | hypoxanthine phosphoribosyl-transferase | defective salvage of purines; increase in the excretion of uricacid; brain neurotransmitter dysfunction; severe spastic movement disorder; self-injurious behavior | allopurinol (does not treat neurological symptoms) |

LYSOSOMAL STORAGE DISORDERS

405

| Disease | Defective Enzyme or System | Symptoms | Treatment |
|---|---|---|---|
| Gaucher disease Types I and II | cerebrosidase | enlargement of the spleen and liver; painful and crippling effects on the bones; severe brain disease and death (Type II) | enzyme replacement (Type I) |
| Tay-Sachs disease | beta-hexosaminidase A | neurological disorders; enlarged head; death in early childhood | |
| Fabry disease | a-galactosidase | severe pain; renal failure; heart failure | enzyme replacement |
| Hurler syndrome, Hunter syndrome | α-iduronidase (Hurler syndrome); iduronate sulfatase (Hunter syndrome) | enlargement of the liver and spleen; skeletal deformities; coarse facial features; stiff joints; mental retardation; death within 5-15 years | enzyme replacement |
| Sanfilippo syndrome | enzymes for heparan sulfate degradation | enlargement of the liver and spleen | enzyme replacement |
| Maroteaux-Lamy syndrome | arylsulfatase B | progressive, crippling and life-threatening physical changes similar to Hurler syndrome, but generally with normal intellect | |
| Morquio syndrome | galactose 6-sulfatase; β-galactosidase | truncal dwarfism; severe skeletal deformities; potentially life-threatening susceptibility to cervical spine dislocation; valvular heart disease | |

DISORDERS OF UREA FORMATION

| Disease | Defective Enzyme or System | Symptoms | Treatment |
|---|---|---|---|
| | carbamyl phosphate synthetase deficiency; ornithine transcarbamylase deficiency; citrullinemia, argininosuccinic aciduria | hyperammonemia; mental retardation; seizures; coma; death | limitation of dietary protein; phenylacetate; liver transplantation |

FIG. 4G

DISORDERS OF PEROXISOMAL METABOLISM

| Disease | Defective Enzyme or System | Symptoms | Treatment |
|---|---|---|---|
| Refsum disease | Branched-chain fatty acid buildup | neurologic symptoms | |
| Alanine-glyoxylate transaminase defect | alanine-glyoxylate transaminase | oxalic acid increase; organ dysfunction; renal failure | liver transplantation |

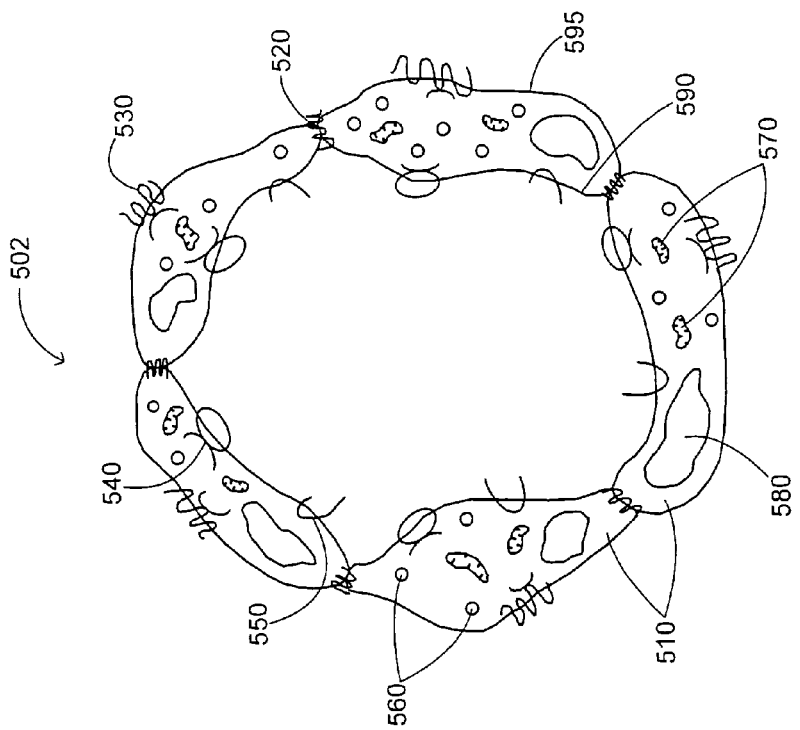
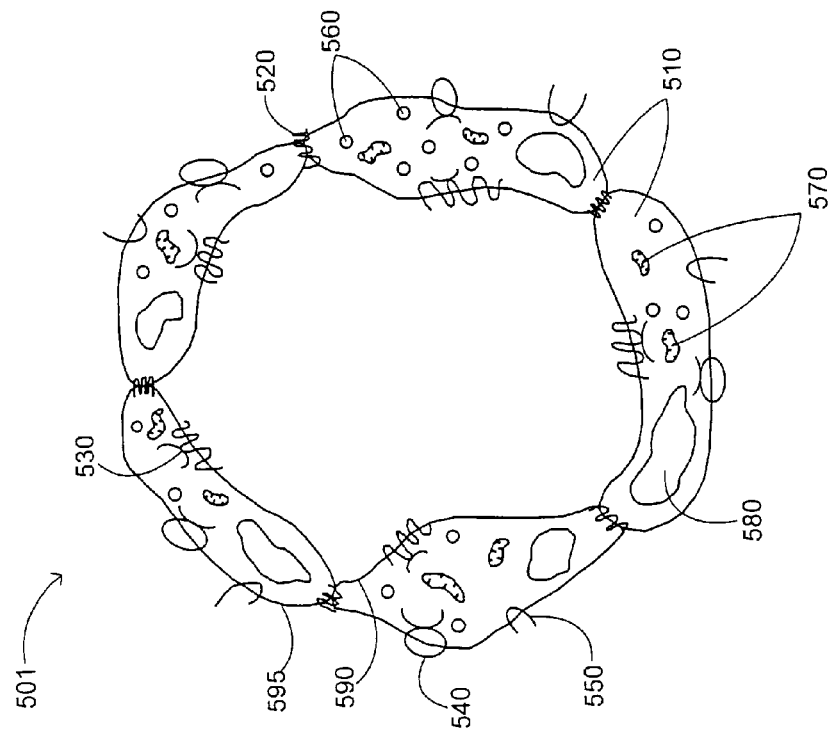

CHOROID PLEXUS DEVICE

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation of U.S. patent application Ser. No. 11/389,268, entitled BLOOD BRAIN BARRIER DEVICE, naming Ed Harlow; Roderick A. Hyde; Edward K. Y. Jung; Robert Langer; Eric C. Leuthardt and Lowell L. Wood, Jr. as inventors, filed Mar. 24, 2006, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/304,486, entitled BONE DELIVERY DEVICE, naming Ed Harlow; Roderick A. Hyde; Edward K. Y. Jung; Robert Langer; Eric C. Leuthardt and Lowell L. Wood, Jr. as inventors, filed 14 Dec. 2005, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/304,492, entitled BONE CELL DELIVER DEVICE, naming Ed Harlow; Roderick A. Hyde; Edward K. Y. Jung; Robert Langer; Eric C. Leuthardt and Lowell L. Wood, Jr. as inventors, filed 14 Dec. 2005, which is currently co-pending, or is an application of which a currently co-pending application is entitled to the benefit of the filing date. For purposes of the USPTO extra-statutory requirements, the present application constitutes a continuation-in-part of U.S. patent application Ser. No. 11/304,499, entitled BONE SEMI-PERMEABLE DEVICE, naming Ed Harlow; Roderick A. Hyde; Edward K. Y. Jung; Robert Langer; Eric C. Leuthardt and Lowell L. Wood, Jr. as inventors, filed 14 Dec. 2005, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present applicant entity has provided above a specific reference to the application(s) from which priority is being claimed as recited by statute. Applicant entity understands that the statute is unambiguous in its specific reference language and does not require either a serial number or any characterization, such as "continuation" or "continuation-in-part," for claiming priority to U.S. patent applications. Notwithstanding the foregoing, applicant entity understands that the USPTO's computer programs have certain data entry requirements, and hence applicant entity is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BRIEF DESCRIPTION OF THE FIGURES

FIG. 1A shows an exterior view, including an optional semi-permeable membrane on one part. FIG. 1B shows a cross-sectional view.

In FIG. 2A, the bone cage is shown with a buckeyball shape. In FIG. 2B, the bone cage is shown with a barrel-like lattice work configuration. In FIG. 2C, the bone cage is shown with large cut-outs in the walls.

FIGS. 3A, 3B, and 3C show bone cages with closable openings. In FIG. 3A, the opening is closed with a bone plug. In FIG. 3B, the opening is shown closed using an overlapping petri dish type of closure. In FIG. 3C, the opening is shown closed by attaching two egg shell-like halves.

FIGS. 4A, 4B, 4C, 4D, 4E, 4F, and 4G are tables describing diseases and disorders that may be prevented, treated and/or ameliorated using one or more bone cages. FIG. 4A is a table describing disorders of amino acid metabolism. FIG. 4B is a table describing disorders of organic acid metabolism. FIG. 4C is a table describing disorders of fatty acid metabolism. FIG. 4D is a table describing disorders of purine and pyrimidine metabolism. FIG. 4E is a table describing lysosomal storage disorders. FIG. 4F is a table describing disorders of urea formation. FIG. 4G is a table describing disorders of peroxisomal metabolism.

FIGS. 5A and 5B are schematic representations of an illustrative blood brain barrier device. FIG. 5A shows a cross-sectional view with the endothelial cell ablumenal surface oriented toward the exterior of the device. FIG. 5B shows a cross-sectional view with the endothelial cell ablumenal surface oriented toward the internal cavity.

FIG. 6A shows a cross-sectional view with the epithelial cell apical surface oriented toward the exterior of the device. FIG. 6B shows a cross-sectional view with the epithelial cell apical surface oriented toward the internal cavity.

DETAILED DESCRIPTION

Figure 1A:
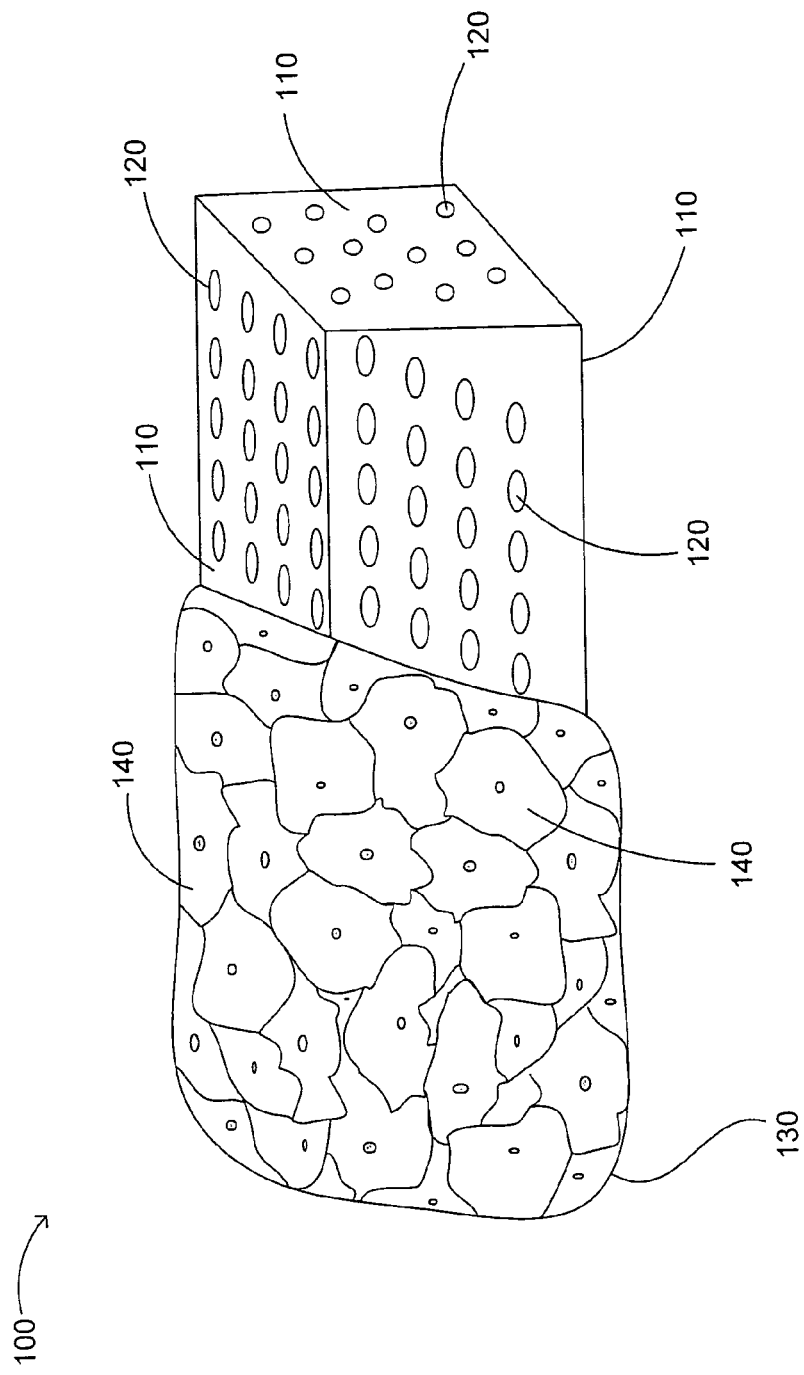
FIGS. 1A and 1B are schematic representations of an illustrative bone cage.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

This disclosure is drawn, inter alia, to devices and methods for delivering one or more biologically active molecules and/or one or more living cells or tissues to a subject.

In one aspect, the disclosure is drawn to a device comprising a bone cage designed to, configured to, and/or structured to at least partially or completely surround one or more biologically active molecules and/or one or more living cells or tissues. In some embodiments, the device is a structure comprised of bone. In some embodiments, the device is implantable and/or biocompatible.

As used herein, the term "implantable" means able to be placed within a subject. The bone cage may be implanted by any method known in the art including, but not limited to, surgery, injection, suppository, and inhalation. The bone cage may be placed, for example, subcutaneously, intra-muscularly, intra-peritoneally, intra-venously, intra-arteriolar, in capillary beds, subdermally, intradermally, orally, rectally, or nasally. The bone cage may be implanted during a surgical procedure, or may be injected using, for example, a hollow bore needle, such as those used for biopsies. Alternatively, injection may be by a gun, such as those used for anesthetic darts. The bone cage can be implanted in any location in a subject appropriate for the desired treatment, such locations are well-known to health care workers including, but not limited to, physicians and nurses, as well as veterinary, animal husbandry, fish, game, zoo, bird, reptile, and exotic animal officials.

In some embodiments, the bone cage is implanted in well-vascularized soft tissue, including, but not limited to, liver, kidney, muscle, lung, cadiac and/or brain tissue. In other embodiments, the bone cage is implanted in less well-vascularized tissue including, but not limited to, joints, cartilage, and fat. In some embodiments, the bone cage is implanted in bone or behind the blood brain barrier. In yet other embodiments, the bone cage is implanted in the bladder, uterus, or vagina.

As used herein, the term "biocompatible" means a material the body generally accepts without a significant immune response/rejection or excessive fibrosis. In some embodiments, some immune response and/or fibrosis is desired. In other embodiments, vascularization is desired. In other embodiments, vascularization is not desired.

In some embodiments, the bone cage is implanted in a subject selected from the group consisting of mammal, reptile, bird, amphibian, and fish. In some embodiments, the subject is selected from the group consisting of domesticated, wild, research, zoo, sports, pet, primate, marine, and farm animals. In some embodiments, the animal is a mammal. In some embodiments, the mammal is a human. In other embodiments, the primate is a human. Animals further include, but are not limited to, bovine, porcine, swine, ovine, murine, canine, avian, feline, equine, or rodent animals. Domesticated and/or farm animals include, but are not limited to, chickens, horses, cattle, pigs, sheep, donkeys, mules, rabbits, goats, ducks, geese, chickens, and turkeys. Wild animals include, but are not limited to, non-human primates, bear, deer, elk, raccoons, squirrels, wolves, coyotes, opossums, foxes, skunks, and cougars. Research animals include, but are not limited to, rats, mice, hamsters, guinea pigs, rabbits, pigs, dogs, cats and non-human primates. Pets include, but are not limited to, dogs, cats, gerbils, hamsters, guinea pigs and rabbits. Reptiles include, but are not limited to, snakes, lizards, alligators, crocodiles, iguanas, and turtles. Avian animals include, but are not limited to, chickens, ducks, geese, owls, sea gulls, eagles, hawks, and falcons. Fish include, but are not limited to, farm-raised, wild, pelagic, coastal, sport, commercial, fresh water, salt water, and tropical. Marine animals include, but are not limited to, whales, sharks, seals, sea lions, walruses, penguins, dolphins, and fish.

As used herein, the term "cage" or "structure" means a rigid, semi-rigid, or otherwise structurally supportive structure with at least one external wall, and at least one internal cavity within which, for example, a semi-permeable membrane and/or one or more living cells or tissues and/or one or more biologically active molecules can be placed. In some embodiments, the one or more living cells or tissues and/or one or more biologically active molecules do not include bone tissue. The external wall can be any shape, including but not limited to, spherical, oval, rectangular, square, trapezoidal or modified versions of these shapes. The internal cavity can also be any shape, including but not limited to, spherical, oval, rectangular, square, trapezoidal or modified versions of these shapes. Moreover, the internal cavity may include one or more portions that may be in fluid or similar communication or may be isolated.

In some embodiments, the external wall is approximately any dimension, preferably an integer μm from 1 to 1,000 including, but not limited to, 2 μm, 3 μm, 4 μm, 5 μm, 8 μm, 10 μm, 12 μm, 15 μm, 20 μm, 25 μm, 50 μm, 100 μm, 200 μm, 300 μm, 500 μm, 600 μm, 800 μm and 1,000 μm. In other embodiments, the external wall is approximately 1 μm to 1,000 μm, 2 μm to 500 μm, 3 μm to 250 μm, 4 μm to 100 μm, 5 μm to 50 μm, 5 μm to 10 μm, 2 μm to 20 μm, 1 μm to 50 μm, 5 μm to 25 μm, or 2 μm to 8 μm in width. In some embodiments, the width is not uniform throughout the structure.

In some embodiments, the diameter of the internal cavity is approximately any integer μm from 1 to 1,000 including, but not limited to, 2 μm, 3 μm, 4 μm, 5 μm, 8 μm, 10 μm, 12 μm, 15 μm, 20 μm, 25 μm, 50 μm, 100 μm, 200 μm, 300 μm, 500 μm, 600 μm, 800 μm or 1,000 μm. In other embodiments, the diameter is approximately 1 μm to 1,000 μm, 2 μm to 800 μm, 5 μm to 750 μm, 10 μm to 500 μm, 20 μm to 250 μm, 10 μm to 100 μm, 5 μm to 50 μm, 1 μm to 10 μm, 2 μm to 20 μm, 1 μm to 50 μm, 50 μm to 500 μm, or 250 μm to 1,000 μm in width. In some embodiments, the internal diameter is not uniform throughout the structure.

In some embodiments, the external wall is porous. As used herein, the term "porosity" is defined as the percentage of void space in a solid (Adv. Colloid Interface Sci. (1998) 76-77:341-72). It is a morphological property independent of the material. Porosity may be created by, for example, salt leaching, gas foaming, phase separation, freeze-drying, and sintering, depending on the material used to fabricate the bone scaffold.

In some embodiments, the porosity is approximately any integer percentage from 1% to 99% including, but not limited to, 2%, 3%, 4%, 7%, 10%, 12%, 15%, 20%, 35%, 50%, 60%, 75%, and/or 90%. In other embodiments, the porosity is approximately 1% to 99%, 1% to 15%, 3% to 12%, 5% to 10%, 40% to 95%, 50% to 90%, 60% to 75%, 3% to 90%, 10% to 75%, 15% to 90%, and 25% to 90%. In some embodiments, the porosity is not uniform throughout the bone. The porosity of trabecular bone is 50% to 90%, while that of cortical bone is 3% to 12% (Biomaterials (2005) 26:5474-5491). In some embodiments, the pore size is approximately any integer nm from 1 to 10,000 including, but not limited to, 2 nm, 3 nm, 4 nm, 5 nm, 8 nm, 10 nm, 12 nm, 15 nm, 20 nm, 25 nm, 50 nm, 100 nm, 200 nm, 300 nm, 500 nm, 600 nm, 800 nm, 1,000 nm, 2,000 nm, 5,000 nm, or 10,000 nm. In other embodiments, the pore size is approximately 1 nm to 10,000 nm, 10 nm to 5,000 nm, 25 nm to 1,000 nm, 50 nm to 750 nm, 100 nm to 500 nm, 10 nm to 100 nm, 5 nm to 50 m, 1 nm to 10 nm, 2 nm to 20 nm, 500 nm to 5,000 nm, 1,000 nm to 10,000 nm, or 250 nm to 1,000 nm in width. In some embodiments, the pore size is not uniform throughout the structure.

Figure 1B:
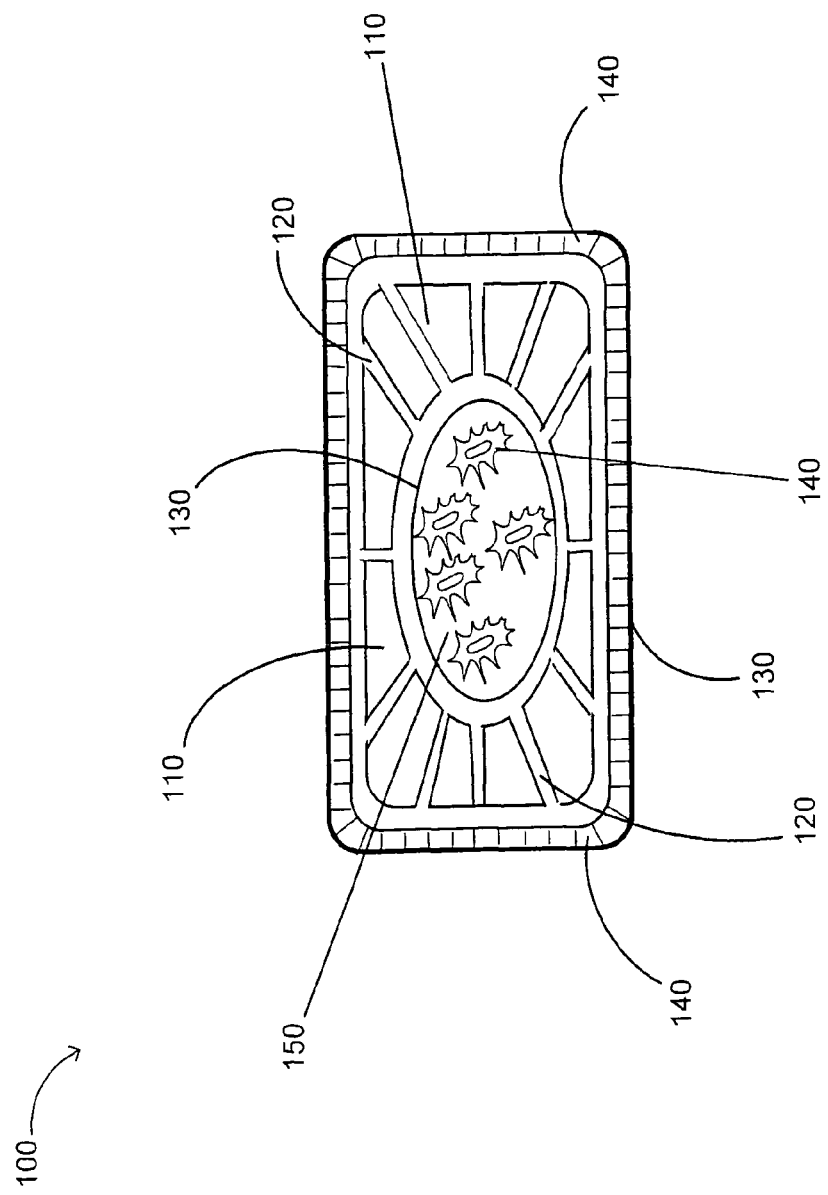

In some embodiments, the bone cage completely surrounds the one or more biologically active molecules and/or one or more living cells or tissues. Illustrative examples of bone cages that completely surround the one or more biologically active molecules and/or one or more living cells or tissues is shown in FIG. 1. In FIG. 1A, a rectangular cage 100 is depicted, showing a bone structure 110 with pores 120 partially surrounded by a semi-permeable component 130 optionally comprised of cells 140. FIG. 1B shows a cross-section of the rectangular cage 100, showing the optional exterior semi-permeable component 130 optionally comprised of cells 140, and the optional interior semi-permeable component 130, as well as the bone structure 110 with pores 120, and the internal cavity 150 with optional cells 140.

In other embodiments, the bone cage partially surrounds the one or more biologically active molecules and/or one or more living cells or tissues. As used herein, the term "partially surrounds" describes a material or other structure, such as an external wall of the bone cage that surrounds less than 100% of a material, structure, region, or other object or location. An example of a material that may be partially surrounded is the one or more biologically active molecules and/or one or more living cells or tissues in the internal cavity. The term "less than 100%" includes any integer percentage from 1% to 99%. Illustrative integers include, 10%, 25%, 50%, 75%, and 95%.

Examples of bone cages with external walls that partially surround the internal cavity include, but are not limited to, those where the external wall is a lattice, and/or where there are openings in the wall that are larger than the pore size of the bone. Examples of lattice work external walls include, but are not limited to, those patterned after buckeyballs.

Examples of external walls with openings include, but are not limited to, those with openings designed to facilitate the placement of the semi-permeable membrane, and/or the one or more biologically active molecules, and/or the one or more living cells or tissues, for example, within the internal cavity. In some embodiments, the width of the one or more openings in the external wall is approximately any integer μm from 1 to 1,000 including, but not limited to, 2 μm, 3 μm, 4 μm, 5 μm, 8 μm, 10 μm, 12 μm, 15 μm, 20 μm, 25 μm, 50 μm, 100 μm, 200 μm, 300 μm, 500 μm, 600 μm, 800 μm and 1,000 μm. In other embodiments, the width is approximately 1 μm to 1,000 μm, 2 μm to 800 μm, 5 μm to 750 μm, 10 μm to 500 μm, 20 μm to 250 μm, 10 μm to 100 μm, 5 μm to 50 μm, 1 μm to 10 μm, 2 μm to 20 μm, 1 μm to 50 μm, 50 μm to 500 μm, or 250 μm to 1,000 μm in width, and the length is the width of the external wall as described above.

Figure 2A:
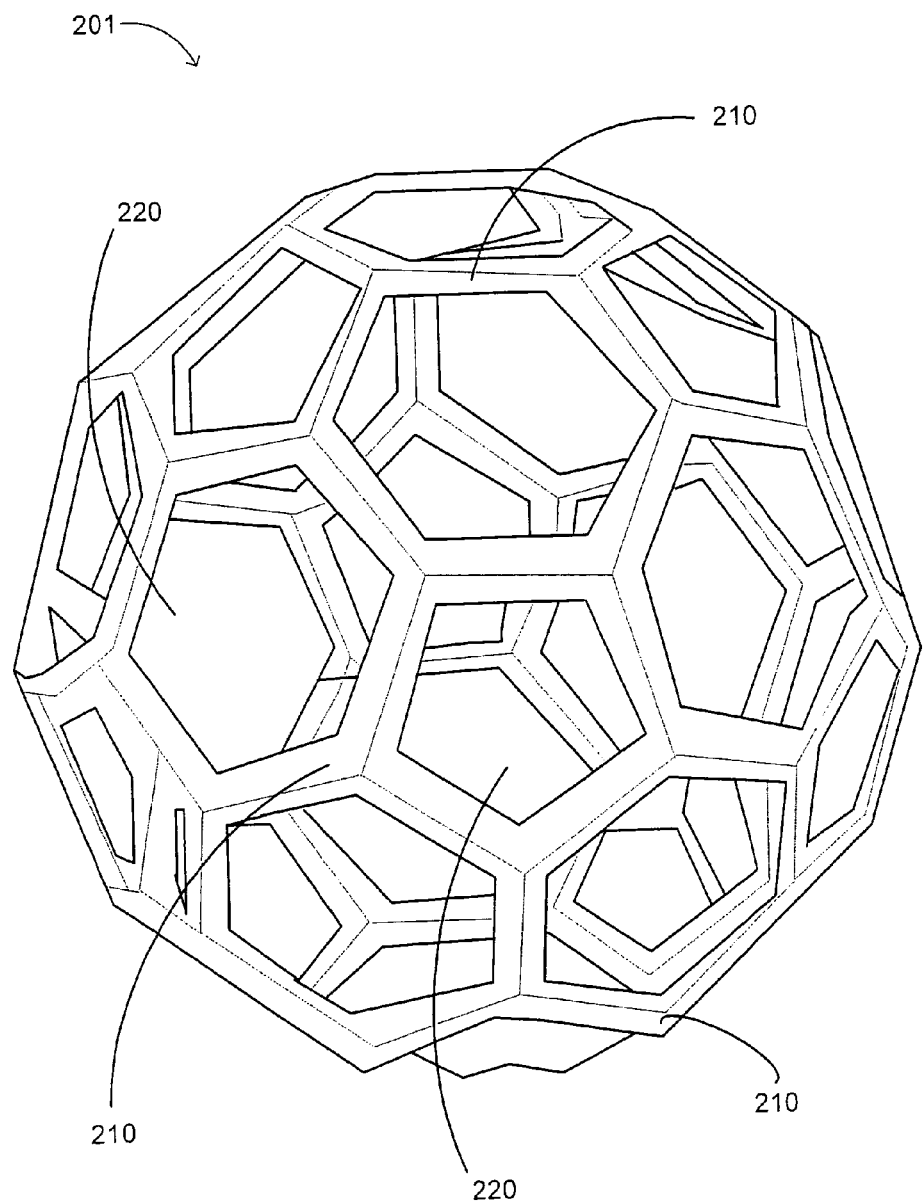
FIGS. 2A, 2B, and 2C are schematic representations of a bone cage that partially surrounds the internal cavity.
Figure 2B:
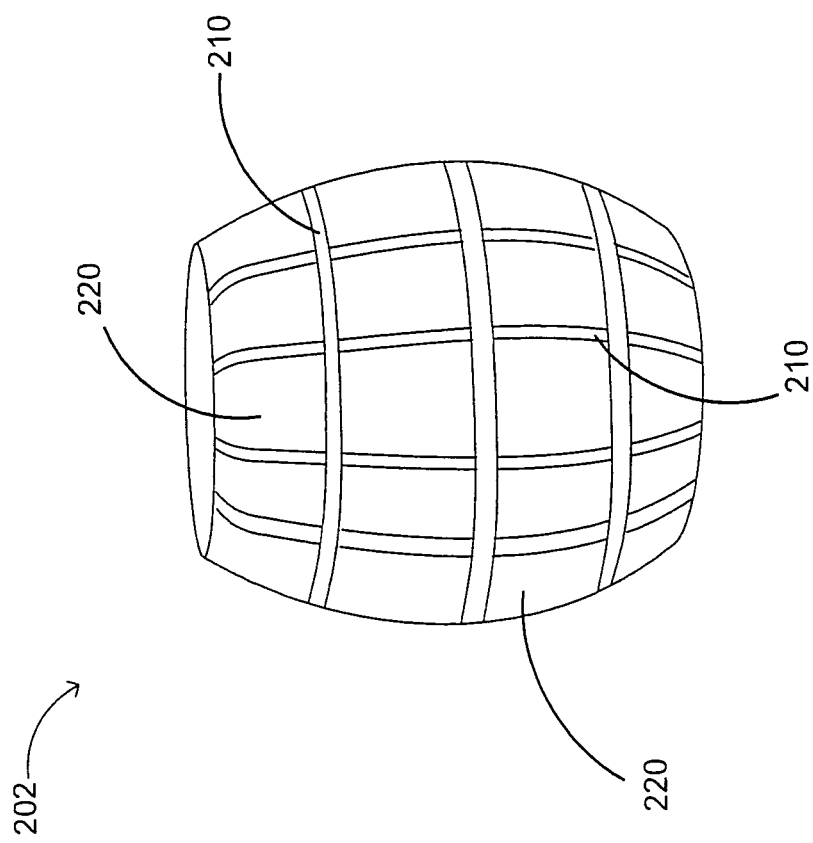
Figure 2C:
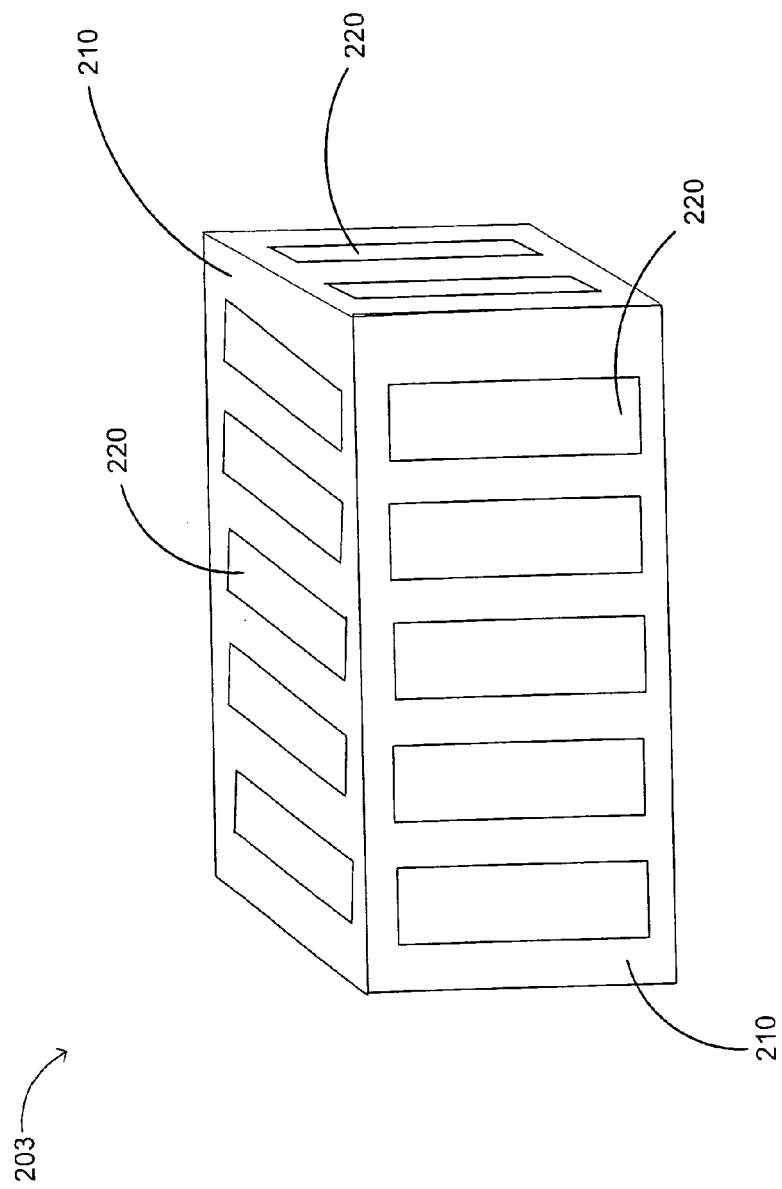

Illustrative examples of bone cages that partially surround the one or more biologically active molecules and/or one or more living cells or tissues is shown in FIG. 2. FIG. 2A shows a buckeyball shaped cage 201 in which the pentagonal and hexagonal shapes are comprised of bone 210. FIG. 2B shows a barrel-like shape 202, in which the vertical and horizontal members 210 are comprised of bone with pores in between 220. FIG. 2C shows a rectangular structure 203, comprised of a bone structure 210 containing large openings as pores 220.

In some embodiments where the external wall has one or more openings, the openings are closable. As used herein, the term "closable" means that an opening or other structural feature is configured to be completely or partially filled, such that the opening can be made no longer larger than the pore size of the bone. In some embodiments, the closure has a width sufficiently greater than the width of the opening to allow attachment to the external wall completely surrounding the opening, and can be secured by any method known in the art. In other embodiments, the closure spans the entire width of the opening, and/or the entire length. In some embodiments, the plug or closure is comprised of bone, including but not limited to, anorganic, artificial, demineralized, cultured in vitro, autologous, allogeneic or xenogeneic bone, or any combination thereof.

Figure 3A:
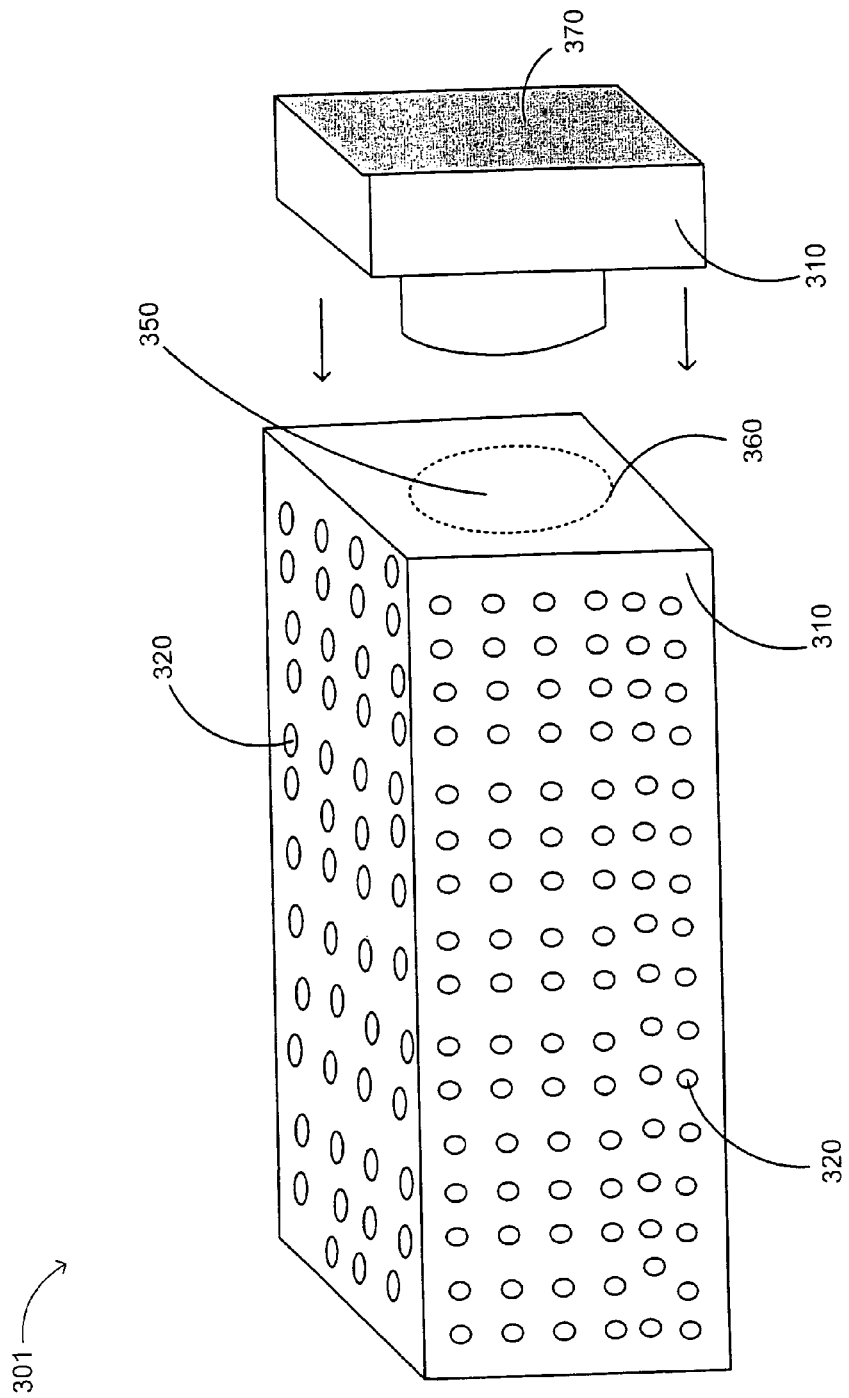

Illustrative embodiments of a bone cage with closable openings are shown in FIG. 3. FIG. 3A shows a rectangular cage 301 comprised of bone 310 containing pores 320 containing an opening 360 that connects with the internal cavity 350. The opening 360 is closable by the insertion of a plug 370 made of bone 310 of a size to approximately entirely fill the opening. FIG. 3B shows the two open halves 304 and 306 of a petri dish-shaped cage 302 made of bone 310 containing pores 320 in which one half 304 has a uniformly slightly smaller diameter than the other half 306 so that the sides of 306 overlap the sides of 304 on closure such that an internal cavity 350 remains. The two halves 304 and 306 are optionally secured by sliding a partial internally protruding edge 385 under a partial externally protruding edge 380. On closing, 304 and 306 are positioned such that 380 and 385 can slide past each other. Once the internally protruding edge 385 is past the externally protruding edge 380, the halves 304 and 306 are twisted such that externally and internally protruding edges 380 and 385 align. FIG. 3C shows the two open halves 305 and 307 of an egg shell-shaped structure 303 made of bone 310 comprising pores 320, where the edges 390 and 395 of the two halves 305 and 307, respectively, optionally mate to allow a screw-type seal, forming an internal cavity 350.

As used herein, the term "bone" encompasses all types of bone known in the art, including but not limited to, organic, anorganic, demineralized, freeze-dried, and artificial bone. The bone may be cultured in vitro, and/or genetically engineered. The bone may be living or dead. The bone may be autologous, allogeneic, or xenogeneic with respect to a subject within whom or which the bone is implanted. In some embodiments, the bone may be a combination of one or more of the types of bone described above.

As used herein, the term "organic bone" encompasses all kinds of bone obtained from donors including cortical, trabecular and cancellous. The bone may be autologous (autografts), allogeneic (allografts) or xenogeneic (xenografts) with respect to a subject within whom or which the bone is implanted. An autograft is a graft from one part of an individual to another part of the same individual. An allograft is a graft between genetically different individuals within one species. A xenograft is a graft between individuals of different species.

In illustrative embodiments, the bone cage is comprised of autologous bone excised from the iliac crest, skull, or fibula, for example. Autologous grafts do not typically have immune rejection issues.

In other illustrative embodiments, the bone cage is comprised of allogeneic bone harvested from a cadaver from any location, for example, and is typically frozen prior to re-implantation to decrease immunogenicity. Following an allograft, donor cells generally do not survive in the recipient (The Merck Manual, Sec. 12, Ch. 149, Transplantation). Examples include, but are not limited to, Allogro, Orthroblast, Opteform and Grafton.

In yet other illustrative embodiments, xenogeneic bone is obtained from animals and is used for xenografts in man. For example, Surgibone Unilab, which is prepared from bovine bone, has been used to augment autografts for hip revision surgery (Acta Orthop. (2005) 76:544-9). Studies of the immunological mechanisms underlying the rejection of pig organs injected into primates has resulted in the development of novel lines of genetically engineered pigs that are more immunologically compatible with man (J. Nephrol. (2003) 16(suppl 7):S16-21), and useful for bone xenografts.

In other embodiments, the bone cage is comprised of anorganic bone. Anorganic bone or anorganic bone matrix is well known in the art for use bone repair (Clin. Plast. Surg. (1994) 21:437-44; J. Long Term Eff. Med. Implants (1998) 8:69-78). As used herein, the term "anorganic bone or anorganic bone matrix" includes autologous, allogeneic, or xenogeneic bone with respect to a subject within whom or which the bone is implanted that has been deorganified. Illustrative examples include, but are not limited to, Bio-Oss® (Geistlich, Wolhusen, Switzerland), which is composed of anorganic bovine bone (Arch Oral. Biol. (2005) July 29 Epub ahead of print), and an anorganic bone matrix described in Biomaterials ((2005) 26:5648-57).

In yet other embodiments, the bone cage is comprised of demineralized bone. Demineralized bone allograft is known in the art for bone repair (Cell Tissue Bank (2005) 6:3-12). As used herein, the term "demineralized bone" includes autologous, allogeneic, or xenogeneic bone with respect to a subject within whom or which the bone is implanted that has been demineralized. An illustrative example of the use of demineralized, freeze-dried bone together with anorganic bovine bone for maxillary sinus grafting is presented in Int. J. Oral Maxillofac. Implants ((2003) 18:556-60).

Once the organic, anorganic, freeze-dried and/or demineralized bone is obtained, the cage can be created in a variety of ways known in the art. In illustrative embodiments, the bone is machined using, for example, microtomes such as the Leica SP 2600 (or 1600) Saw Microtome (Leica Microsystems Nussloch GmbH, Postfach 1120, Heidelberger Strasse 17-19, D-69226 Nussloch, Germany) that can slice bone to a finished thickness of approximately 20-30 µm. Lasers, such as the YAG laser rod, can be used to cut bone with a minimum width of approximately 10 µm for deeper beam penetrations and less than 1 µm for thin coatings (Laserod Inc. 1846-A West 169$^{th}$ Street, Gardena, Calif. 90247-5252). Micro tweezers, such as those from MEMS Precision Instruments (http://memspi.com), can be used to assemble the pieces as necessary. Methods for preparing 2-50 µm thick sections of undecalcified hard tissues are known in the art (Histochem Cell. Biol. (2000) 113:331-339).

An illustrative example of a bone cage that could be constructed using these techniques is shown in FIG. 2C. Since bone is a tubular structure, sections could be sliced perpendicular to the tubular Haversian systems that make up cortically dense bone to produce very thin bone rings. These rings could then be further sectioned into barrel staves to form a barrel-shaped construct, laid side by side to form a tube-shaped construct, or overlapped to make smaller portal structures. Further holes and smaller cutting could create joints to allow the various components to fit together and be assembled using micro tweezers.

An illustrative example of a method to make bone cages of FIG. 1 and/or FIG. 3A is described below. The bone cage is constructed by excising a portion of cortical bone approximately 3 mm by 1 mm from the iliac crest of a subject using a microsaw. This portion of bone is then micromachined to a desired size, for example 30 µm by 90 µm using a microsaw. The shape is rectangular, or smoothed to an oblong, although other shapes may be implemented. The interior cavity of the bone cage is hollowed using a micromachining laser, leaving an approximately 5 µm thick bone wall. The bone wall is perforated with 1 to 2 µm holes using a micromachining laser. A second piece of bone is micromachined and shaped to form a bone cap or plug.

In another embodiment, bone cages are constructed by excising a portion of bone, followed by micromachining to the desired size and/or shape. The orientation of the construct is selected to align the natural pores of the bone to form a natural internal cavity for the bone cage. The interior cavity of the bone cage can be further refined using focused beam machining to enlarge or re-shape the interior cavity of the bone cage. Additional pores can be added as described above, if the natural porosity of the bone is not sufficient to allow the desired amount and/or type of nutrients and/or other materials to reach and/or elute from the internal cavity.

The methods for making a bone cage described above are illustrative and are not intended to be limiting. In addition, it should be anticipated that these and other methods could be used in combination as well as separately.

In other embodiments, the bone cage is comprised of biocompatible and/or implantable artificial bone substitutes containing metals, ceramics and/or polymers. Artificial bone scaffolding is known in the art for use in bone repair (Int. J. Oral Maxillofac. Surg. (2004) 33:325-332; Int. J. Oral Maxillofac. Surg. (2004) 33:523-530). As used herein, the term "artificial bone" includes any bone substitute composites or scaffolds known in the art with a structural rigidity substantially equal to or greater than that of cartilage, and with pores that allow at least fluid passage. In some embodiments, the pores allow passage of macromolecules, but not cells. In other embodiments the pores allow passage of cells as well as macromolecules. As used herein, the term "passage" may include diffusion, release, extrusion, and/or migration.

The mechanical properties of naturally occurring bone, including stiffness and tensile strength, are provided by the bone tissue "scaffold" which contains significant amounts of non-living material, such as organic minerals as well various proteins of the extracellular matrix.

A variety of bone substitutes are used in tissue engineering to create scaffolds (Synthetic Biodegradable Polymer Scaffolds (1997) Boston, Mass.: Birkhauser; J. Biomed. Mater. Res. (2001) 54:162-171; Int. J. Oral Maxillofac. Surg. (2004) 33:523-530). These include, but are not limited to, synthetic organic materials such as clinically used nondegradable and biodegradable and bioresorbable polymers including polyglycolide, optically active and racemic polylactides, polydioxanone, and polycaprolactone, polymers under clinical investigation including polyorthoester, polyanhydrides, and polyhydroxyalkanoate, early stage polymeric biomaterials including ploy(lactic acid-co-lysine), as well as biodegradable polymer ceramic scaffolds (J. Mater. Sci. Mater. Med. (2005) 16:807-19; Biomaterials (1998) 19:1405-1412). Examples include, but are not limited to, Cortoss, OPLA, and Immix.

Synthetic inorganic molecules are also used in scaffolding, including hydroxyapatite, calcium/phosphate composites, calcium sulfate, and glass ceramics (Biotechnol. Bioeng. (2005); J. Artif. Organs (2005) 8:131-136; J. Biomed. Mater Res. A. (2005) 68:725-734; J. Long Term Eff. Med. Implants (1998) 8:69-78). Examples include, but are not limited to, Osteograf, Norian SRS, ProOsteon, and Osteoset.

Organic materials of natural origin including collagen, fibrin, and hyaluronic acid are also used, as are inorganic material of natural origin including, for example, coralline hydroxyapatite. A variety of metals have been used in artificial scaffolds for bone, including silicon, titanium and aluminum (J. Biomed. Mater. Res. A. (2004) 70:206-218; J. Biomed. Mater. Res. (2001) 56:494-503; J. Biomed. Mater. Res. A. (2005) 72:288-295).

In addition to the methods for making bone cages discussed above, design and prototyping of scaffolds can be performed digitally (Biomaterials (2002) 23:4437-4447; Int. J. Prothodont. (2002) 15:129-132), and the material can be processed as sponge-like sheets, gels, or highly complex structures with intricate pores and channels (Ann. NY Acad. Sci. (2002) 961:83-95). A biocompatible three-dimensional internal architectural structure with a desired material surface topography, pore size, channel direction and trabecular orientation can be fabricated (Biomaterials (2002) 23:4437-4447). Fabrication of scaffolding can be accomplished using conventional manual-based fabrication techniques (Frontiers in Tissue Engineering (1998) New York, Elsevier Science 107-120; J. Biomed. Mater. Res. (2000) 51:376-382; J. Biomater. Sci. Polymer. E. (1995) 7; 23-38), or computer-based solid free form fabrication technologies (Br. J. Plast. Surg. (2000) 53:200-204), for example.

In some embodiments, the bone cage is comprised of cells cultured in vitro including, but not limited to, stem cells, fibroblasts, endothelial cells, osteoblasts and/or osteoclasts. In some embodiments, the non-stem cells are isolated from a subject. Bone cell populations may be derived from all bone surfaces by a variety of techniques known in the art, including mechanical disruption, explantation, and enzyme digestion (Tissue Eng. (1995) 1:301-308). Methods to culture and/or propagate osteoprogenitor cells and/or osteoblast-like cells in vitro are also well known in the art (Int. J. Oral Maxillofac. Surg. (2004) 33:325-332). Culture conditions for manufacturing bone tissue including, but not limited to, temperature, culture medium, biochemical and mechanical stimuli, fluid flow and perfusion, are known in the art (Int. J. Oral Maxillofac. Surg. (2004) 33:523-530).

In other embodiments, the non-stem cells are differentiated from stem cell including, but not limited to, fetal, embryonic, cord blood, mesenchymal and/or hematopoeitic. In some embodiments, the numbers of stem cells are increased in number in culture in vitro prior to differentiation. Methods for isolation, culturing and transplantation of stem cells are known in the art (Fetal Diagn. Ther. (2004) 19:2-8; Best Pract. Res. Clin. Obstet. Gynaecol. (2004) 18:853-875).

In illustrative embodiments, the stem cells are mesenchymal stem cells. Mesenchymal stem cells are multipotent cells found in several, perhaps most, adult tissues (Blood (2005) 105:1815-1822). Mesenchymal stem cells can be reliably isolated and cultured in therapeutic quantities (Bone (1992) 13:81-88), and several methods to isolate mesenchymal stem cells from, for example, bone marrow, adipose tissue, and muscle, based on the physical and immunological characteristics are known in the art (Basic & Clinical Pharmacology & Toxicology (2004) 95:209-; Ann. Biomed. Eng. (2004) 32:136-147). Mesenchymal stem cells are able to differentiate into various lineages including osteoblasts in vitro (Science (1999) 284:143-147; J. Cell Sci. (2000) 113:1161-1166; Int. J. Oral Maxillofac. Surg. (2004) 33:325-332).

In some embodiments, the bone cage is comprised of cells cultured in vitro on bone scaffolding. In some embodiments, the bone scaffolding is degradable in vitro and/or in vitro. Porosity and pore size of the scaffold are known to play a role in bone formation, osteogenesis and osteoconduction in vitro and in vivo, and methods of measuring and controlling porosity and pore size in artificial scaffolds are known in the art (Biomaterials (2005) 26:5474-5491).

In illustrative embodiments, stem cells and/or osteoblast progenitor cells are propagated on scaffolds of a variety of shapes including, those shown in FIG. 2. The cells are grown until fusion, or partially grown to result in a lattice shape. The bone cells cultured in vitro include autologous, allogeneic, or xenogeneic cells, with respect to a subject within whom or which the bone cage is implanted. An illustrative method of making a bone cage, such as bone cages of FIG. 3B or 3C, using mesenchymal stem cells is described below. An artificial scaffold of, for example, degrable polymer, is laid down in the desired open lattice-work shape of the two halves of the bone structure. Expanded mesenchymal stem cells (autologous, allogeneic, or xenogeneic) are cultured in the lattice-work shapes, in vitro, and encouraged to differentiate into osteoblasts. Once the cells have populated the lattice structure, other optional components of the bone device are added and the device implanted.

In some embodiments, the bone cage comprises living tissue. As used herein, the term "living tissue" refers to the presence of living bone cells such as, but not limited to, osteoblasts, or osteoclasts within the bone scaffold. As used herein, the term "living tissue" includes living bone cells in artificial bone scaffolding. The living tissue can be autologous, allogeneic, or xenogeneic, with respect to a subject within whom or which the bone cage is implanted.

In some embodiments, the bone cage comprises dead tissue. As used herein, the term "dead tissue" refers to the absence of living bone cell, such as, but not limited to, osteoblasts, or osteoclasts within the bone scaffold. The dead tissue can be autologous, allogeneic, or xenogeneic, with respect to a subject within whom or which the bone cage is implanted.

In some embodiments, the bone cage is designed and/or treated to, at least partially or completely, prevent restructuring. As used herein, the term "restructuring or restructured" as it relates to the bone cage means a change in the physical structure of the bone cage, including but not limited to, bone size, shape, architecture and quality. Bone restructuring includes, but is not limited to, bone resorption and osteoconduction (or bone deposition). In the case of a bone cage with artificial scaffolding, autologous, or non-autologous bone, bone restructuring would include, but not be limited to, the influx and growth of the subject's bone cells in the artificial, autologous, or non-autologous bone scaffold. Mechanisms of restructuring, treatments to modify restructuring, and genes governing restructuring are known in the art (Nature (2005) 1:47-54).

Methods for detecting and measuring changes in bone are well-known in the art. The change can result, for example, from global or discrete increases or decreases in bone mass. Alternatively, the change can result, for example, from global or discrete increases or decreases in the relative ratios of cells, including but not limited to, the number of osteoblasts as compared with the number of osteoclasts. The change can also result, for example, from global or discrete increases or decreases in bone pore size and/or porosity. As used herein, the terms "increase" and/or "decrease" in bone mass, relative ratio of cells, or pore size and/or porosity, for example, are measured as any integer percent change from 1% to 99% as compared with the original bone mass, relative ratio of cells, or pore size and/or porosity, respectively, either globally or in a discrete location. Illustrative integers include 10%, 25%, 50%, 75%, and 95%.

Bone restructuring, a combination of bone resorption by osteoclasts and bone deposition by osteoblasts, can be modified by methods known in the art. As used herein, the term "resorption" as it relates to the bone cage means a decrease in bone mass from either global or discrete reductions in, for example, the extracellular matrix and/or cells. Bone resorption is mediated by osteoclasts, so treatments that inhibit the activity of osteoclasts decrease bone resorption. Methods for detecting and measuring these changes are well-known in the art (Biomaterials (2005) 26:5474-5491).

In some embodiments, restructuring of the bone cage is partially or completely reduced or prevented. In other embodiments, the bone is designed and/or treated to be at least partially, or completely, restructured. Modifications of bone restructuring can result, for example, from administration of compounds that influence bone resorption and/or deposition, by the selection of the pore size and/or porosity of the bone, by the selection of the type of bone, by the selection of the location of implantation, as a result of inherent, induced, or genetically modified immunogenicity, and as a result of other genetic modification. In some embodiments, the bone is partially or completely resorbable.

Compounds that influence bone restructuring through modifications in bone resorption and/or deposition can be applied before, during, or after implantation of the bone cage at the discretion of the health professional and depending on the timing and the extent of the modification of a subject's bone restructuring desired. Administration of the compounds may be systemic or localized. Systemic and local administration includes any method used in the art for pharmaceutical administration.

In illustrative embodiments, compounds can be administered locally by being applied to, or made part of, the bone either globally, or in localized areas, depending on whether complete or partial restructuring is desired. An illustrative example is the incorporation of the cell binding peptide P-15 on anorganic bovine bone matrix (Biomaterials (2004) 25:4831-4836; J. Biomed. Mater. Res. A. (2005) 74:712-721; Biomaterials (2005) 26:5648-4657). Other examples include, but are not limited to, addition of TGF-β, platelet-derived growth factor, fibroblast growth factor, and bone morphogenic proteins.

In other illustrative embodiments, compounds can be administered by incorporation in the bone cage as one of the one or more biologically active molecules and/or living cells and/or tissues, as discussed herein.

In illustrative embodiments, bis-phosphonates, used systemically to prevent bone resorption (Osteoporos Int. (2002) 13:97-104), are applied before, during, or after implantation of the bone cage to partially or completely modify bone restructuring (Curr. Osteoporos. Rep. (2003) 1:45-52). Such therapies can also be administered locally by treating the bone cage, or by placing them inside the cage as one of the one or more biologically active molecules and/or one or more living cells or tissues, to elute out over time. Alternatively, discrete portions of the bone cage could be coated to selectively prevent restructuring as discussed above.

In illustrative embodiments, one or more hormones including, but not limited to, estrogen, growth hormone, calcitonin, vitamin D, and/or calcium, which encourage bone growth, are administered before, during, or after implantation of the bone cage to partially or completely modify bone restructuring. In other embodiments, the bone cage is treated globally or discretely with a thin layer of one or more of these hormones to encourage bone growth throughout or in discrete locations.

In yet other illustrative embodiments, anabolic therapies including, but not limited to hormones such as parathyroid-hormone (PTH-(1-84)), teriparatide (PTH-(1-34)), and/or excess glucocorticoid, that are known to increase bone turnover and porosity are administered systemically (Osteoporosis Int. (2002) 13:97-104) to partially or completely modify restructuring. In other embodiments, these hormones are administered locally by treating the entire bone cage, or discrete portions of the bone cage, to allow selective restructuring. In yet other embodiments, these hormones are administered by placing them inside the cage as one of the one or more other biologically active molecules and/or one or more living cells or tissues.

In other illustrative embodiments, bone resorption is influenced by the administration of cytokines that increase osteoclast activity including, but not limited to, interleukin-1, M-CSF, tumor nevrosis factor, and/or interleukin-6. In other embodiments, bone resorption is influenced by the administration of cytokines that decrease osteoclast activity including, but not limited to, interlekin-4, gamma-interferon, and/or transforming growth factor-beta. In yet other embodiments, bone resorption is influenced by other humoral factors including, but not limited to, leukotrienes, arachidonic metabolites, and/or prostaglandins and their inhibitors and including 5-lipoxygenase enzyme inhibitors.

In yet other illustrative embodiments, bone formation is influenced by the administration of factors that promote osteoblast activity and proliferation including, but not limited to, insulin-like growth factors I and II, transforming growth factor-beta, acidic and basic fibroblast growth factor, platelet-derived growth factor, and/or bone morphogenic proteins.

Bone pore size and porosity influence bone restructuring through modifications in bone resorption and/or deposition. Since the size of the pores in the bone impacts new bone growth, decreasing the pore size and/or the percent of porosity of the bone in the cage reduces or prevents restructuring. In contrast, increasing the pore size and/or the percent porosity of the bone in the cage enhances restructuring. The bone cage can be constructed such that the pore size and porosity is approximately uniform through out the cage, or that the pore size and porosity varies depending on the location. Varying the pore size and/or porosity in discrete locations leads to partial restructuring (either partial enhancement or partial prevention).

In illustrative embodiments, the pore size is approximately 1 nm to 10 nm, 1 nm to 20 nm, 1 nm to 25 nm, 1 n to 50 nm, 1 nm to 100 nm, 1 nm to 150 nm, 15 nm to 50 nm, 50 nm to 100 nm, 25 nm to 100 nm, 50 nm to 150 nm, or 25 nm to 150 nm. In other illustrative embodiments, the pore size may be larger, for example approximately 150 nm to 500 nm, 250 nm to 750 nm, or 500 nm to 1,500 nm, in one or more locations. This may, for example, allow partial restructuring in these one or more locations.

In other illustrative embodiments, the pore size may be approximately 150 nm to 500 nm, 250 nm to 750 nm, or 500 nm to 1,500 nm. In other illustrative embodiments, the pore size may be smaller, for example approximately 1 nm to 20 nm, 1 nm to 25 nm, 1 nm to 50 nm, 1 nm to 100 nm, 1 nm to 150 nm, 15 nm to 50 nm, 50 nm to 100 nm, 25 nm to 100 nm, 50 nm to 150 nm, or 25 nm to 150 nm. This may, for example, prevent or reduce restructuring in these one or more locations.

In illustrative embodiments, the porosity is approximately 1% to 15%, 3% to 12%, 5% to 10%, 1% to 3%, 1% to 5%, or 1% to 10% in one or more locations. In other embodiments, the porosity may be a greater percentage in one or more locations, for example approximately 40% to 95%, 50% to 90%, 60% to 75%, 15% to 90%, and 25% to 90%. This may, for example, allow partial restructuring in these one or more locations.

The type of bone used in the fabrication of the cage influences bone restructuring through modifications in bone resorption and/or deposition. Measurements of the influence on bone restructuring of each type of bone are performed in vitro, as well as in pre-clinical and clinical studies. Different bone types and/or sources have a differential ability to support restructuring. As a result, bone restructuring can be partially or completely reduced, or alternatively, partially or completely enhanced depending on the bone chosen. In addition, different bone types/sources can be used in discrete locations in the bone cage to enhance or prevent/decrease bone restructuring.

In illustrative embodiments, studies assessing the ability of new bone or bone cells to restructure a variety of artificial and/or anorganic bone in bone transplant patients or in vitro culture have shown, for example, that implantation of Bio-Oss lead to limited, reduced or absent restructuring compared with other artificial or natural organic bone options such as Algipore (Clin. Oral Implants Res. (2004) 15:96-100; J. Mater. Sci. Mater. Med. (2005) 16:57-66). Since these studies have also identified artificial bone that encourages restructuring, as does natural bone, the bone cage could be designed with portions that are resistant to restructuring as well as portions that encourage restructuring as desired.

In other illustrative embodiments, bone restructuring is modified by making the bone cage from cortical bone, or trabecular or cancellous bone. The choice of bone will impact the extent of restructuring since cortical bone is generally less porous than trabecular or cancellous bone. In addition, discrete parts of the bone cage could be formed from one type of bone or another to influence the restructuring of discrete locations.

In yet other embodiments, bone restructuring is modified by the location of implantation. Bone restructuring is greater when the bone is implanted in bone rather than other locations. The type of bone the bone cage is implanted in will also influence the extent of restructuring. In illustrative embodiments, the bone cage is implanted in bone, for example cortical, or cancellous or trabecular bone. In other embodiments, the bone cage is implanted in non-bone tissues including, for example, liver, muscle, lung, or fat.

Immunogenicity of the bone cage influences bone restructuring through modifications in bone resorption and/or deposition by osteoblasts and osteoclasts, as well as through immune mechanisms. Methods of influencing the immunogenicity of cells are known in the art. Illustrative examples include, but are not limited to, the immuno-compatibility of donor and recipient, the inherent immunogenicity of the bone material or cells, the presence of immune modulatory compounds, and genetic modifications.

In some embodiments, the bone cage is partially or completely non-immunogenic with respect to a subject within whom the device is implanted, or alternatively, is partially or completely recognized as self. In other embodiments, the bone cage is partially or completely immunogenic with respect to a subject within whom the device is implanted, or alternatively, is partially or completely recognized as non-self. As used herein, the term "non-immunogenic" means that the immune response, if any, is not such that immune suppressive drugs would be required following implantation of the bone cage.

In some embodiments, bone cage restructuring and immunogenicity is modified by the immuno-compatibility of donor and recipient. In illustrative embodiments, bone cages completely or partially made from bone derived from a donor autologous to the recipient of the bone cage, are non-immunogenic and recognized as self. In some embodiments, previously frozen allogeneic bone, as well as xenogeneic or allogeneic anorganic bone, is considered non-immunogenic.

In illustrative embodiments, bone cages are completely or partially made from bone derived from a donor allogeneic to the recipient of the bone cage. In some embodiments, in which the bone is from cadavers, and frozen, de-mineralized, and/or deorganified, immuno-suppressive therapy is not generally required although some recipients may develop anti-HLA antibodies (The Merck Manual of Diagnosis and Therapy. Sec. 12, Ch. 149). In other embodiments, in which the allogeneic bone is not frozen, deorganified or demineralized, for example, an immune response may result unless modified by other means, such as immuno-suppressive therapy.

In other illustrative embodiments, bone cages are completely or partially made from bone derived from a donor xenogeneic to the recipient of the bone cage. In some embodiments, in which the bone is anorganic bovine bone, for example, immuno-suppressive therapy is not required, although some recipients may experience a transient macrophage infiltrate, but no systemic or local immune response (J. Periodontol. (1994) 65:1008-15). In other embodiments, in which the bone cage is made from xenogeneic bone that is not anorganic or pre-frozen, for example, the bone cage is immunogenic and not recognized as self.

In yet other embodiments, the bone cage is partially made from non-immunogenic bone, such as but not limited to, autologous bone and/or pre-frozen, de-organified, and/or demineralized allogeneic bone, and/or anorganic xenogeneic bone and partially made from immunogeneic bone, such as but not limited to, allogeneic bone that is not pre-frozen, de-organified, and/or de-mineralized and/or xenogeneic bone that is not anorganic. In some embodiments, the immunogenic bone is placed in discrete locations to encourage restructuring. In other embodiments, the non-immunogenic bone is place in discrete locations to prevent or reduce restructuring.

In some embodiments, bone cage restructuring and immunogenicity is modified by the inherent immunogenicity of the bone material or cells. In some embodiments, bone cages are completely or partially made from stem cells including, but not limited to mesenchymal, fetal, cord blood, and/or hematopoietic stem cells. In other embodiments, bone cages are completely or partially made from differentiated stem cells such as bone cells, including but not limited to, osteoblasts and/or osteoclasts, fibroblasts, or endothelial cells. In some embodiments, the cells are autologous, allogeneic, or xenogeneic as relates to a subject in whom or which they are implanted.

In illustrative embodiments, the bone cage is composed of autologous, allogeneic, xenogeneic and/or artificial bone in which autologous, allogeneic, and/or xenogeneic stem cells have been cultured. In some embodiments, the stem cells have been induced to differentiate into, for example, bone cells including but not limited to osteoblasts and/or osteoclasts. In yet other embodiments, stem cells are cultured in discrete areas of the bone cage. In some embodiments, the autologous, allogeneic and/or xenogeneic mesenchymal stem cells partially or completely decrease the immunogenicity of part, or all, of the bone cage.

Stem cells generally have decreased immunogenicity and can induce transplant tolerance. For example, hematopoietic stem cells are known to induce tolerance as can embryonic stem cells (Expert Opin. Biol. Ther. (2003) 3:5-13). In addition, transplanted allogeneic mesenchymal stem cells demonstrate a lack of immune recognition and clearance (Blood (2005) 105:1815-1822; Bone Marrow Transplant (2002) 30:215-222; Proc. Natl. Acad. Sci. USA (2002) 99:8932-8937) as well as being useful in graft-versus-host disease (Lancet (2004) 363:1439-1441). Mesenchymal stem cells do not activate alloreactive T cells even when differentiated into various mesenchymal lineages (Exp. Hematol. (2000) 28:875-884; Exp. Hematol. (2003) 31:890-896), and suppress proliferation of allogeneic T cells in an MHC-independent manner (Transplantation (2003) 75:389-397; Blood (2005) 105:1815-1822).

In some illustrative embodiments, the bone cage is composed of autologous, allogeneic, xenogeneic and/or artificial bone in which autologous, allogeneic, and/or xenogeneic bone cells have been cultured. The bone cells may include, but are not limited to osteoblasts and osteoclasts. In some embodiments, the bone cells are cultured in discrete areas of the bone cage. In illustrative embodiments, bone cages created from autologous, allogeneic, xenogeneic and/or artificial bone, in which allogeneic or xenogeneic (to a subject in which it is to be implanted) bone cells are propagated, increases the immunogenicity of the bone cage when implanted in the subject.

In some embodiments, bone cage restructuring and/or immunogenicity is modified by the presence of immuno-modulator compounds. These include immuno-suppressive as well as immuno-stimulatory compounds, both of which are known in the art. Immuno-suppressive compounds decrease immunogenicity and hence decrease restructuring, while immuno-stimulatory compounds increase immunogenicity and hence increase restructuring. The immuno-modulatory compounds may be administered systemically to a subject before, during and/or after implantation of the bone cage using methods known in the art. The compounds can be adsorbed onto the surface of the bone cage, placed inside it as one of the one or more biologically active molecules, or secreted from the one or more living cells or tissues. In an embodiment in which the one or more immuno-modulatory compounds are adsorbed onto the bone cage, they could be adsorbed to one or more discrete locations on the bone cage.

In illustrative embodiments, the immuno-suppressive compounds include, but are not limited to, corticosteroids, such as prednisolone or methylprednisolone. In other illustrative embodiments the immune stimulatory and/or inflammatory molecules include, but not limited to, tumor necrosis factor α, interferon γ, interleukin 2, and/or one or more selecting. Other appropriate compounds are known in the art by health professionals and can be found, for example, in the Physician's Desk Reference.

In illustrative embodiments, immune stimulatory and/or inflammatory molecules may be applied to discrete locations on the bone cage. In some embodiments, this results in partial or complete restructuring of the discrete area. In other illustrative embodiments, immuno-suppressive compounds may be applied to discrete locations on the bone cage. In some embodiments, this prevents or reduces restructuring of the bone cage in at least those locations.

In some embodiments, the bone cage comprises cells that have been genetically modified. In some embodiments, the genetically modified cells include, but are not limited to, stem cells, bone cells, cells comprising the semi-permeable component, and/or one or more living cells or tissues.

In illustrative embodiments, genetic modification of cells influences bone restructuring and/or immunogenicity. In some embodiments, genetic modification of cells influences bone resorption and/or deposition. In other illustrative embodiments, genetic modification of cells stimulates or inhibits immune reactions. In yet other embodiments, genetic modification of cells influences the permeability and/or the immuno-isolatory aspects of the semi-permeable component. In other embodiments, genetic modification of cells results in the release, secretion, diffusion and/or deposition of one or more biologically active molecules. In yet other embodiments, genetic modification of cells influences the binding of one or more biologically active molecules to the bone cage including, but not limited to, the bone wall and/or the semi-permeable component.

In some embodiments, the bone cage comprises genetically modified stem cells including, but not limited to, embryonic, fetal, mesenchymal, and/or hematopoietic stem cells. In some embodiments, the stem cells are non-differentiated. In other embodiments, the stem cells are stimulated to differentiate. In illustrative embodiments, the stem cells are non-differentiated mesenchymal stem cells. In other embodiments, the mesenchymal stem cells have been differentiated into cells selected from the group consisting of osteoblast, osteoclast and endothelial cells.

In some embodiments, cells are genetically modified to increase or decrease bone restructuring. In other embodiments, stem cells, such as mesenchymal stem cells, are genetically modified to be more or less osteoconductive when differentiated into osteoblasts or other components of bone. Methods for genetic modification of mesenchymal stem cells are known in the art (Ann. Biomed. Eng. (2004) 32:136-47; Biochem. Biophysica Acta (2005) September 15 Epub; Cloning Stem Cells (2005) &:154-166).

Methods for modifying the osteoconduction of cells are known in the art. For example, bone morphogenetic protein-2 (BMP-2) an osteoinductive agent, up-regulates the expression of osteogenic phenotypes, and induces bone nodule formation in a dose-dependent manner (Spine (2004) 29:960-5). Ciz, an inhibitor of osteoblast differentiation, interferes with bone morphogenic protein signaling, which leads to increased bone mass. In illustrative embodiments, a BMP and/or Ciz gene is transduced into cells and/or its expression up-regulated. Alternatively, a BMP and/or Ciz gene is deleted from the cells by genetic knock out or iRNA, and/or its expression down-regulated by methods known in the art.

In other embodiments, cells are genetically modified to increase or decrease immunogenicity and/or an immune response. In illustrative embodiments, cells including, but not limited to stem cells, bone cells, cells of the semi-permeable component, and/or the one or more living cells or tissues, are genetically modified to express immune recognition markers of the host, to secrete and/or express anti-inflammatory molecules, and/or to express or secrete immune-stimulatory molecules.

In some embodiments, the bone cage partially or completely surrounds and/or is surrounded by a semi-permeable component. In other embodiments, the bone cage partially or completely encloses and/or is enclosed by a semi-permeable component. In some embodiments, the semi-permeable component is partially or completely comprised of the bone wall of the bone cage. In other embodiments, the semi-permeable component is partially or completely external to the bone wall of the bone cage. In other embodiments, the semi-permeable component is partially or completely internal to the bone wall or the bone cage. In some embodiments, the semi-permeable component partially or completely encloses one or more living cells or tissues and/or one or more biologically active molecules.

As used herein, the term "semi-permeable component" means a selective impediment to the passage of fluids and/or substances in the fluids. In some embodiments, the semi-permeable component prevents the passage of macromolecules and cells, but allows the passage of oxygen and/or nutrients. In some embodiments, the passage of one or more biologically active molecules from the cage and/or products released by the one or more living cells or tissues in the cage is allowed. In other embodiments, the passage of macromolecules, or macromolecules and cells is allowed.

In some embodiments, the semi-permeable component includes, but is not limited to, the bone wall, one or more semi-permeable membranes, cells with tight junctions, one or more plasma membranes, one or more intracellular membranes, one or more red blood cell ghosts, and one or more aggregated platelets or other cells. In some embodiments, the semi-permeable component is comprised of cells that are autologous, allogeneic, or xenogeneic with respect to a subject within whom or which they may be implanted.

In some embodiments, part, or all, of the semi-permeable component is partially or completely non-immunogenic and/or is recognized as self by a subject within whom or which it is implanted. In other embodiments, part, or all, of the semi-permeable component is partially or completely immunogenic and/or is recognized as non-self by a subject within whom or which it is implanted.

In other embodiments, the semi-permeable component is comprised of cells that are cultured in vitro. In some embodiments, the semi-permeable component is comprised of cells that are genetically engineered. In some embodiments, some or all of the cells are genetically engineered to release, secrete, deliver, diffuse, and/or provide one or more biologically active molecules. In some embodiments, some or all of the cells are genetically engineered to be less immunogenic or to be more immunogenic. In yet other embodiments, some or all of the cells are genetically engineered to increase or decrease bone restructuring including, but not limited to, bone deposition and bone resorption. In some embodiments, the semi-permeable component is designed to at least partially or completely enhance restructuring.

In some embodiments, the semi-permeable component is a semi-permeable membrane. In illustrative embodiments, the semi-permeable membrane includes, but is not limited to, artificial membranes, biological membranes, and/or a combination of artificial and biologically-derived components. The manufacture and use of artificial semi-permeable membranes is known in the art (Cell Transplant (2001) 10:3-24). Known artificial semi-permeable membranes include, but are not limited to, hydrogel membranes (Biochim. Biophys. Acta (1984) 804:133-136; Science (1991) 254:1782-4; J. Biomed. Mater. Res. (1992) 26:967-977) and ultrafiltration membranes (Diabetes (1996) 45:342-347; J. Clin. Invest. (1996) 98:1417-1422; Transplantation (1995) 59:1485-1487; J. Biomech. Eng. (1991) 113:152-170), both which have been employed in the immuno-isolation of xenografts, for example (Ann. NY Acad. Sci. (1999) 875:7-23). The membranes can be made, for example, from polymer films and thermoplastic hollow fibers. In addition, biological semi-permeable membranes are used to encapsulate islet cells followed by implantation (World J. Gastroenterol. (2005) 11:5714-5717).

In other embodiments, the semi-permeable component is partially or completely composed of cells with tight junctions. As used herein, the term "tight junction" or zonula occludens is the intercellular junction that regulates diffusion between cells and allows the formation of barriers that can separate compartments of different composition. The intercellular gate formed by tight junctions is size and ion selective, among other things.

In some embodiments, the cells with tight junctions include, but are not limited to, epithelial and/or endothelial cells, or a combination. Both epithelial cells and endothelial cells are known to form tight junctions between cells (Methods (2003) 30:228-234).

In yet other embodiments, the semi-permeable component is comprised of cells with tight junctions where the cells are stem cells, or are differentiated from stem cells. In illustrative embodiments, stem cells are cultured in vitro to confluency on the interior and/or exterior of a bone scaffold of the desired shape and composition. In some embodiments, the stem cells include, but are not limited to, one or more of mesenchymal, embryonic, fetal, or hematopoietic stem cells. In some embodiments, the stem cells are stimulated to differentiate. In some embodiments, the stem cells differentiate into one or more of endothelial cells and epithelial cells. In some embodiments, the stem cells differentiate into bone cells, including but not limited to, osteoblasts or osteoclasts. In other embodiments the stem cells do not differentiate into bone cells.

Methods for differentiating mesenchymal stem cells into endothelial cells (Basic & Clin. Pharmacol. & Toxicol. (2004) 95:209-214) and hematopoietic stem cells into epithelial stem cells are known in the art. Stem cells are known to be relatively non-immunostimulatory, and to retain this characteristic following differentiation.

In yet other embodiments, the semi-permeable component is a plasma membrane. In some embodiments, the plasma membrane is made from red cell ghosts. Red cell ghosts are created by removal of the erythrocyte cytoplasm by lysis followed by size-exclusion chromatography. In some embodiments, one or more red cell ghosts encapsulate the one or more biologically active molecules and/or the one or more living cells and/or tissues. Methods of using red cell ghosts for drug delivery are known in the art (Expert Opinion on Drug Delivery (2005) 2:311-322; Drug Delivery (2003) Taylor & Francis eds. 10(4):277-282; BioDrugs (2004) 18:189-198).

In other embodiments, the one or more red cells ghosts are fused to form an internal or external continuous or semi-continuous membrane. In some embodiments, the fused red blood cell ghosts encapsulate the one or more biologically active molecules and/or the one or more living cells and/or tissues.

In other embodiments, the semi-permeable component is an aggregate of platelets. In an illustrative embodiment, the bone cage is coated internally and/or externally with a platelet aggregating compound on which platelets aggregate in vitro and/or in vivo. In some embodiments the platelet aggregating compound includes, but is not limited to, fibrin, fibrinogen and/or thrombin. For example, fibrinogen is known to play a role in platelet aggregation (Coll. Anthropol. (2005) 29:341-9).

In yet other embodiments, the semi-permeable component is comprised of endothelial cells having one or more characteristics of a blood brain barrier. In the body, the blood brain barrier is a specialized system of capillary endothelial cells that protect the brain from harmful substances in the blood stream, while supplying the brain with the required nutrients for proper function. The blood brain barrier strictly limits transport into the brain through both physical (tight junctions) and metabolic (enzymes) barriers (Ann. Rev. Pharmacol. Toxicol. (2003) 43:629-56).

In some embodiments, the semi-permeable component is comprised of endothelial cells having one or more characteristics of cerebral capillary endothelial cells. In some embodiments, the semi-permeable component includes one or more characteristics of cerebral capillary endothelium that is different from the characteristics of peripheral capillary endothelium or non-cerebral capillary epithelium. In other embodiments, the semi-permeable membrane includes one or more characteristics of cerebral capillary endothelium that is not a characteristic of peripheral capillary endothelium or non-cerebral capillary epithelium.

The microvasculature of the central nervous system differs from peripheral tissue endothelium in several ways, including in tight junctions, cytoplasm, mitochondria, enzymatic barriers, wall thickness, and polarity.

In some embodiments, the semi-permeable component comprises endothelial cells with interendothelial tight junctions. Cerebral capillary endothelial cells contain tight junctions, which seal cell-to-cell contacts between adjacent endothelial cells forming a continuous blood vessel. The tight junctions between blood brain barrier endothelial cells lead to high endothelial electrical resistance, in the range of 1500 to 2000 $\Omega$-cm$^2$ (pial vessels) and as high as 8000 $\Omega$cm$^2$ (non-pial vessels), as compared with 3-33 $\Omega$cm$^2$ in other tissues (J. Gen. Physiol. (1981) 77:349-71; J. Neurochem. (1986) 46:1732-1742; J. Physiol. (1990) 429:47-6%). The elevated resistance in brain endothelium leads to low paracellular (between cell) permeability.

In some embodiments, the interendothelial tight junctions have an endothelial resistance greater than 33 $\Omega$cm$^2$, greater than 50 $\Omega$cm$^2$, greater than 100 $\Omega$cm$^2$, greater than 200 $\Omega$cm$^2$ greater than 500 $\Omega$cm$^2$, greater than 750 $\Omega$cm$^2$, or greater than 1000 $\Omega$cm$^2$. In other embodiments, the interendothelial tight junctions have an endothelial resistance between 33 $\Omega$cm$^2$ and 8000 $\Omega$cm$^2$, 50 $\Omega$cm$^2$ and 8000 $\Omega$cm$^2$, 100 $\Omega$cm$^2$ and 8000 $\Omega$cm$^2$, 200 $\Omega$cm$^2$ and 8000 $\Omega$cm$^2$, 500 $\Omega$cm$^2$ and 8000 $\Omega$cm$^2$, 750 $\Omega$cm$^2$ and 8000 $\Omega$cm$^2$, or 1000 $\Omega$cm$^2$ and 8000 $\Omega$cm$^2$. In yet other embodiments, the interendothelial tight junctions have an endothelial resistance between 1500 to 2000 $\Omega$-cm$^2$, 1000 to 2500 $\Omega$-cm$^2$, 500 to 2500 $\Omega$-cm$^2$, 100 to 2000 $\Omega$-cm$^2$, 1500 to 5000 $\Omega$-cm$^2$, or 1500 to 8000 $\Omega$-cm$^2$.

In some embodiments, the interendothelial tight junctions include one or more integral membrane proteins different from or not present in peripheral capillary endothelium or non-cerebral capillary endothelium. The intracellular clefts of cerebral capillary endothelium are around 200 angstroms wide, and are constricted by macula and zonula adhaerens and zonula occludens (Circ. Res. (1976) 38:404-411). The adhaerens junction is around 200 angstroms, while the occludens junction (tight junction) is essentially completely occluded. Tight junction membrane components include, but are not limited to, occludin, claudins (multi-gene family of at least 20 isomers, including claudin-1 and claudin-5), zonula occludens (at least ZO-1/2/3), junctional adhesion molecules (JAM), and microdomains on the cell membrane rich in cholesterol, which contain caveolin (J. Cell Biol. (1999) 147: 891-903; Trends Cell Biol. (1999) 9:268-273; J. Cell Biol. (1998) 141:199-208; J. Cell Sci. (2000) 113:1771-1781).

In some embodiments, the semi-permeable component includes endothelial cells with cytoplasm that is different from the cytoplasm of peripheral capillary endothelium Or non-cerebral capillary endothelium. In some embodiments, the cytoplasm is of uniform thickness. In other embodiments, the cytoplasm contains very few pinocytic vesicles. In yet other embodiments, the cytoplasm lacks fenestrations. The cytoplasm of the endothelial cells of the blood brain barrier is of uniform thickness with very few pinocytic vesicles (hollowed out portion of cells membrane filled with fluid, forming a vacuole which facilitates nutrient transport), and lacks fenestrations (openings). The cytoplasm may have one seventh of the amount of pinocytic vesicles compared with muscle capillary endothelial cells. Therefore transport across the blood brain barrier involves translocation through capillary endothelium, the internal cytoplasmic domain, and then through the ablumenal membrane.

In some embodiments, where the cytoplasm has fewer pinocytic vesicles than cytoplasm of peripheral endothelium, there are 10%, 20%, 30%, 50%, 75%, 90% or 95% fewer pinocytic vesicles. In other embodiments, the cytoplasm has 10% to 50%, 25% to 50%, 25% to 75%, 50% to 75%, or 75% to 95% fewer pinocytic vesicles. In yet other embodiments, the cytoplasm has one half, one third, one quarter, one fifth, one sixth, one seventh, one eighth, one ninth, or one tenth the number of pinocytic vesicles found in muscle capillary endothelium.

In some embodiments, where the cytoplasm has fewer fenestrations than the cytoplasm of peripheral endothelium, there are 10%, 20%, 30%, 50%, 75%, 80%, 85% 90%, 95%, or 99% fewer fenestrations. In other embodiments, the cytoplasm has 10% to 50%, 25% to 50%, 25% to 75%, 50% to 75%, 75% to 90%, 85% to 95%, or 95% to 99% fewer fenestrations. In embodiments where the cytoplasm lacks fenestrations, the presence of fenestrations is undetectable by methods known in the art, or there is a decrease in fenestrations that is 95% to 99% or greater compared with peripheral endothelium.

In some embodiments, the semi-permeable component has endothelial cells containing a greater number and/or volume of mitochondria as compared with peripheral endothelium or non-cerebral capillary endothelium. The increase in mitochondria and therefore energy potential, may be required to allow active transport of nutrients to the brain from the blood (Proc. Soc. Exp. Biol. Med. (1975) 149:736-738; Ann. Neurol. (1977) 1:409-417). In some embodiments, there are 5 to 6 times more mitochondria per capillary cross section than in peripheral capillary endothelium. In other embodiments, there are approximately 2, 3, 4, 5, 6, 7, 8, 9, or 10 times more mitochondria per capillary cross section than in peripheral capillary endothelium. In yet other embodiments, there are 2 to 4, 3 to 5, 4 to 7, 8 to 10, 3 to 8, or 2 to 6 times more mitochondria per capillary cross section than in peripheral capillary endothelium.

In some embodiments, the semi-permeable component includes endothelial cells with elevated metabolizing enzymes. The cerebral endothelia contain an enzymatic barrier capable of metabolizing drug and nutrients, including but not limited to, neuroactive solutes (Brain Res. Brain Res. Rev. (1991) 16:65-82; J. Neurochem. (1993) 60:793-803; J. Pharmacol. Exp. Ther. (1994) 270:675-680). Enzymes in elevated concentrations compared with non-neuronal capillary endothelium include, but are not limited to, $\gamma$-glutamyl transpeptidase ($\gamma$-GTP), alkaline phosphatase, and aromatic acid decarboxylase. Other specific enzymes expressed by brain endothelial cells include, but are not limited to, monoamine oxidases, epoxy hydrolase, and endopeptidases. One or more of the enzymes may be absent or at lower levels in non-neuronal capillary endothelium. In some embodiments, the metabolizing enzymes are present at levels at least 10%, 20%, 30%, 50%, 75%, 90%, 100%, 200%, or 500% higher. In other embodiments, the metabolizing enzymes are present at levels 10% to 50%, 25% to 50%, 25% to 75%, 50% to 75%, 75% to 100%, 100% to 200%, or 200% to 500% higher.

In some embodiments, the semi-permeable component has endothelium with a decreased capillary wall thickness. Cerebral capillary endothelial cells may have an approximately 39% decrease in the wall thickness compared with muscle capillary endothelial cells (Microvasc. Res. (1985) 30:99-115). In some embodiments, the wall thickness is decreased by 10%, 20%, 30%, 40%, 50%, 60%, or 75% compared with muscle capillary endothelial cells. In other embodiments, the wall thickness is decreased by 10% to 50%, 25% to 50%, 25% to 75%, 50% to 75%, or 30% to 50%.

In some embodiments, the semi-permeable component has endothelium with a defined polarity reflecting the polarity of the lumenal and ablumenal surfaces of the blood brain barrier. As used herein, the term "lumenal" refers to the internal surface of the capillary endothelium. The lumenal surface of the endothelium forms a hollow tube through which blood flows in vivo. As used herein, the term "ablumenal" refers to the exterior surface of the capillary endothelium. The abluminal surface of the endothelium is in contact with structures of the brain in vivo, including astrocytes, pericytes, and neurons.

In some embodiments, polarity of the cerebral capillary endothelium and the semi-permeable membrane is defined through differences in one or more enzymes, receptors, or transporters present on one surface as compared with the other surface. In other embodiments, polarity is defined through presence or absence of one or more enzymes, receptors, or transporters on one surface as compared with the other surface. For example, γ-glutamyl transpeptidase and alkaline phosphatase are usually found associated with the lumenal portion of the blood brain barrier, while $Na^+$—$K^+$-ATPase and the sodium dependent neutral amino acid transporter are usually associated with the ablumenal membrane (Brain Res. (1980) 192:17-28). The glucose receptor (GLUT-1) typically has a 3:1 ratio of distribution, ablumenal to lumenal surface (Proc. Natl. Acad. Sci. USA (1991) 88:5779-5783). The P-glycoprotein (P-gp) drug efflux transporter exists primarily at the lumenal membrane surface.

In some embodiments, the lumenal surface is oriented toward the internal cavity of the semi-permeable membrane of the device. In other embodiments the ablumenal surface is oriented toward the internal cavity of the semi-permeable membrane of the device.

In some embodiments, the semi-permeable component has endothelium with one or more transport systems that are different from those in non-neural capillary endothelium. In some embodiments, one or more of the transport systems are not present in non-neural capillary endothelium. In the blood brain barrier, and in contrast to peripheral endothelium, the rate of pinocytosis is minimal, and free membrane diffusion applies mainly to small lipophilic molecules, including but not limited to, ethanol and nicotine. Active or catalyzed transport systems include carrier-mediated bidirectional transport, typically unidirectional efflux transport, and receptor-mediated transport by endocytosis and transcytosis (Cellular and Molecular Neurobiology (2005) 25:59-127). Carrier-mediated bidirectional transport (responsible for nutrient uptake in the brain) includes, but is not limited to, glucose transporter (GLUT1), monocarboxylic acid transporter (MCT1), large neutral amino acid transporter (LAT1), and sodium-coupled nucleoside transporter (CNT2). Efflux transport typically removes metabolites and xenobiotics from the brain, and/or prevents metabolites and xenobiotics from crossing the endothelium to reach the brain, and includes, but is not limited to, P-glycoprotein and MRP-1 multidrug resistance proteins, brain multidrug resistance protein (ABCG2/BCRP), and organic anion-transporting polypeptide (OATP2). Receptor-mediated transport by endocytosis and transcytosis supplies the brain with peptides and proteins including, but not limited to, low-density lipoproteins, transferrin, leptin, and insulin.

Illustrative embodiments showing blood brain barrier devices are shown in FIG. 5. FIG. 5A shows a cross-section of one orientation of an ovoid blood brain barrier endothelium device 501 comprised of endothelial cells 510 optionally containing interendothelial tight junctions 520, P glycoprotein efflux pump 530 at interior plasma membrane surfaces 590, ion transporters 540 and glucose receptor 550 at exterior plasma membrane surfaces 595, pinocytic vesicles 560, mitochondria 570, and nuclei 580. FIG. 5B shows a cross-section of another orientation of an ovoid blood brain barrier endothelium device 502 comprised of endothelial cells 510 optionally containing interendothelial tight junctions 520, the P glycoprotein efflux pump 530 at exterior plasma membrane surfaces 595, ion transporters 540 and glucose receptor 550 at interior plasma membrane surfaces 590, pinocytic vesicles 560, mitochondria 570, and nuclei 580.

In some embodiments, the endothelium that makes part or all of the semi-permeable component is autologous, allogeneic, or xenogeneic with respect to a subject. The endothelium may be cultured in vitro. The endothelial cells may be from primary brain endothelium, from peripheral endothelium, from an endothelial cell line, or from stem cells. The endothelium may be genetically engineered, designed to partially or completely prevent restructuring, designed to partially or completely enhance restructuring, be immunogenic, be non-immunogenic, and/or be recognized as self.

In some embodiments, the blood brain barrier device may be implantable and biocompatible, and may also include a structural component. The endothelium may at least partially or completely form an internal cavity. The structural component may at least partially or completely form an internal cavity. The combination of the endothelium and the structural component may partially or completely form an internal cavity. In some embodiments, the structural component may surround the endothelium. In other embodiments, the endothelium may surround the structural component. The structural component may be at least partially composed of bone or of cartilage.

In some aspects, a method of making a blood brain barrier device includes, but is not limited to, forming a semi-permeable component from endothelial cells, configuring the semi-permeable component to at least partially form an internal cavity, and engineering the endothelial cells to have one or more characteristics of a blood brain barrier membrane. In some embodiments, at least one of the one or more characteristics of the blood brain barrier membrane is not a characteristic of peripheral endothelium or non-cerebral capillary endothelium. In some embodiments, a method of making a device includes culturing cells in vitro. In some embodiments, the cells include, but are not limited to, endothelial cells, stem cells, and brain endothelial cells. In yet other embodiments, a method of making a device includes differentiating endothelial cells from stem cells, and/or culturing stem cells in vitro. In some embodiments, the blood brain barrier device includes cells that are isolated from autologous, allogeneic, or xenogeneic donors.

In yet other embodiments, a method of making a device includes configuring the semi-permeable component to at least partially form an internal cavity by culturing endothelial cells on a scaffold to at least partially form the internal cavity. In some embodiments, a method of making a device includes configuring the scaffold to at least partially form the internal cavity.

In yet other embodiments, a method of making a device includes selecting a structural component, and combining the structural component and the semi-permeable component. In some embodiments, a method of making a device includes selecting a structural component, and placing the semi-permeable component in the structural component. In some embodiments, a method of making a device includes selecting a structural component, and placing the structural component in the semi-permeable component. In yet other embodiments, a method of making a device includes selecting a structural component, and at least partially surrounding the structural component with the semi-permeable component. In yet other embodiments, a method of making a device includes selecting a structural component, and at least partially surrounding the semi-permeable component with the structural component.

In yet other embodiments, a method of making a device includes identifying one or more biologically active molecules, and providing the one or more biologically active molecules to the internal cavity of the device. In yet other embodiments, a method of making a device includes identifying one or more living cells or tissues, and providing the one or more living cells or tissues to the internal cavity. In some embodiments, the one or more living cells and tissues produce the one or more biologically active molecules.

In other aspects, a method for delivering one or more biologically active molecules to a subject includes, but is not limited to, identifying one or more biologically active molecules useful to a subject, and implanting in the subject one or more of the blood brain barrier devices described in this disclosure. In some embodiments, a method of making a device includes adding the one or more biologically active molecules to the one or more devices before or after implantation of the device in a subject in need of the biologically active molecules. In some embodiments, a method of making a device includes identifying one or more living cells or tissues, and providing the one or more living cells or tissues to the one or more devices. In some embodiments, the one or more living cells and tissues produce the one or more biologically active molecules.

In yet other aspects, a method of assembling a device for delivering one or more biologically active molecules to a subject, includes identifying the one or more biologically active molecules, selecting one or more of the blood brain barrier devices described herein, and providing the one or more biologically active molecules to the device. In some embodiments, a method of making a device includes identifying one or more one or more living cells or tissues, and providing the one or more living cells or tissues to the one or more devices. In some embodiments, the one or more living cells and tissues produce the one or more biologically active molecules.

Models for the blood-brain barrier have been developed in vitro (ATLA (2004) 32:37-50; NeuroAIDS (1998) 1(4):1-6; Proc. Natl. Acad. Sci. USA (1998) 95:1840-1845; Cellular and Molecular Neurobiology (2005) 25:59-127; Brain Research Reviews (2005) 50:258-265; Journal of Pharmacology and Experimental Therapeutics (2006) 316:79-86; Cellular and Molecular Neurobiology (2005) 25:201-210; Biol. Pharm. Bull. (2001) 24:111-118). The characteristics studied include, but are not restricted to, restrictive paracellular permeability, physiologically realistic architecture, expression of the functional transporter mechanisms present in vivo, transendothelial electrical resistance (TEER), endothelial permeability coefficient ($P_e$), and ease of culture. The in vitro blood brain barrier models can derive from isolated brain cells, primary (subpassaged) culture cells, immortalized brain endothelial cells, cell lines of non-cerebral origin, co/multi cultures, and cells free systems, including partition coefficients and artificial membranes.

In yet other embodiments, the semi-permeable component comprises epithelial cells having one or more characteristics of the blood cerebrospinal fluid barrier. In the body, the blood cerebrospinal fluid barrier is a specialized system including modified choroidal epithelial cells. The choroid plexus forms the cerebrospinal fluid and actively regulates the concentration of molecules in the cerebrospinal fluid. The cells of the choroid plexus are modified and have epithelial characteristics. The cells have microvilli on the cerebrospinal fluid side, basolateral interdigitations, and abundant mitochondria. The choroidal epithelial cells form tight junctions preventing most macromolecules from effectively passing into the cerebrospinal fluid from the blood.

In some embodiments, the semi-permeable component comprises epithelial cells having one or more characteristics of choroid plexus epithelium. In some embodiments, the semi-permeable component includes one or more characteristics of choroid plexus epithelium that is different from the characteristics of peripheral epithelium or non-choroid plexus epithelium. In other embodiments, the semi-permeable component includes one or more characteristics of the choroid plexus epithelium that is not a characteristic of peripheral epithelium, and/or non-neural epithelium, and/or non-choroidal plexus epithelium. In some embodiments, the semi-permeable membrane at least partially, or completely, forms an internal cavity.

Characteristics of the choroid plexus epithelium that may be different from the peripheral epithelium include one or more of interepithelial tight junctions, interepithelial electrical resistance, apical microvilli, basolateral interdigitations, mitochondria, active or catalyzed transport systems, and polarity between apical and basal surfaces.

In some embodiments, the semi-permeable component comprises epithelial cells having interepithelial tight junctions. The choroidal plexus epithelium contains tight junctions (spot welds) at the apical zone of neighboring epithelial cells (Pharmaceutical Research (2005) 22:1011-1037). The tight junctions at least partially occlude or block the passage of water soluble agents (depending on molecular size) from one side of the barrier to the other. There is paracellular diffusion of small hydrophilic solutes through choroidal plexus tight junctions. In some embodiments, the interepithelial tight junctions include one or more integral membrane proteins not present in peripheral epithelium or non-choroidal plexus epithelium. The one or more integral membrane proteins may include, but are not limited to, one or more of occludin, claudin-1, and zona occludens-1 (ZO-1).

In some embodiments, the interendothelial tight junctions lead to an increased epithelial electrical resistance compared with peripheral epithelium, or non-choroidal plexus epithelium. In some embodiments, the interepithelial tight junctions have an epithelial resistance greater than 33 $\Omega cm^2$, greater than 50 $\Omega cm^2$, greater than 100 $\Omega cm^2$, greater than 200 $\Omega cm^2$, greater than 500 $\Omega cm^2$, greater than 700 $\Omega cm^2$, greater than 800 $\Omega cm^2$, or greater than 1000 $\Omega cm^2$. In other embodiments, the interepithelial tight junctions have an endothelial resistance between 33 $\Omega cm^2$ and 3000 $\Omega cm^2$, 50 $\Omega cm^2$ and 2500 $\Omega cm^2$, 100 $\Omega cm^2$ and 2000 $\Omega cm^2$, 200 $\Omega cm^2$ and 2000 $\Omega cm^2$, 50 $\Omega cm^2$ and 250 $\Omega cm^2$, 150 $\Omega cm^2$ and 250 $\Omega cm^2$, 700 $\Omega cm^2$ and 800 $\Omega cm^2$, or 1000 $\Omega cm^2$ and 2000 $\Omega cm^2$. In yet other embodiments, the interepithelial tight junctions have an epithelial resistance between 1500 to 2000 $\Omega cm^2$, 1000 to 2500 $\Omega cm^2$, 500 to 2500 $\Omega cm^2$, 50 to 2000 $\Omega cm^2$, 100 to 2000 $\Omega cm^2$, 800 to 2000 $\Omega cm^2$ or 1500 to 5000 $\Omega cm^2$.

In some embodiments, the semi-permeable component comprises epithelial cells with active or catalyzed transport systems. The epithelial cells of the choroid plexus secrete cerebrospinal fluid by a process that involves the transport of $Na^+$, $Cl^-$ and $HCO_3^-$ from the blood to the ventricles of the brain (Neuroscience (2004) 129:957-970). The unidirectional transport of ions is achieved due to the polarity of the epithelium. The ion transport proteins in the blood-facing (basolateral) membrane are different from those in the ventricular (apical) membrane. The apical membrane of the choroid plexus has ion transporters including, but not limited to, $Na^+$—$K^+$ ATPase, $K^+$ channels, and $Na^+$-$2Cl^-$—$K^+$ cotransporters, and aquaporin 1 to mediate water transport. The basolateral membrane of the choroid plexus has ion transporters including, but not limited to, Cl⁻—HCO₃ exchangers, a variety of Na⁺ coupled $HCO_3^-$-transporters, and K⁺—Cl cotransporters.

In some embodiments, the semi-permeable membrane is composed of epithelial cells with one or more characteristics of the choroidal epithelium, including differential localization of ion transport proteins between interior and exterior membranes. In some embodiments, the ion channels of the apical membrane of the choroidal plexus are partially or completely oriented toward the internal cavity of the device. In other embodiments, the ion channels of the apical membrane of the choroidal plexus are partially or completely oriented toward the exterior of the device. In some embodiments, the ion channels of the basolateral membrane of the choroidal plexus are partially or completely oriented toward the internal cavity of the device. In other embodiments, the ion channels of the basolateral membrane of the choroidal plexus are partially or completely oriented toward the exterior of the device. In some embodiments, the localization and/or action of ion transport proteins may result in partially or completely unidirectional transport of ions. The unidirectional transport may occur in either orientation, partially or completely toward the internal cavity, or partially or completely toward the exterior of the device.

In yet other embodiments, the semi-permeable component is composed of epithelial cells with one or more characteristics of the choroidal epithelium, including nutrient transporters. In the brain, the choroid plexus epithelium facilitates nutrient transport from the blood (basolateral surface) to the ventricle (cerebrospinal fluid surface) with transporters that include, but are not limited to, ascorbic acid specific transporter (SVCT2) and the myo-inosital-Na⁺-cotransporter (SMIT; Advanced Drug Delivery Reviews (2004) 56:1859-1873). In some embodiments, the nutrient transporters include, but not limited to, the ascorbic acid specific transporter and the myo-inosital-Na⁺-cotransporter. In some embodiments, the nutrient transporters of the apical membrane of the choroidal plexus are partially or completely oriented toward the internal cavity of the device. In other embodiments, the nutrient transporters of the apical membrane of the choroidal plexus are partially or completely oriented toward the exterior of the device. In some embodiments, the nutrient transporters of the basolateral membrane of the choroidal plexus are partially or completely oriented toward the internal cavity of the device. In other embodiments, the nutrient transporters of the basolateral membrane of the choroidal plexus are partially or completely oriented toward the exterior of the device. In some embodiments, the localization and/or action of nutrient transporters may result in partially or completely unidirectional transport of nutrients. The unidirectional transport may occur in either orientation, partially or completely toward the internal cavity, or partially or completely toward the exterior of the device.

In some embodiments, the semi-permeable component is composed of epithelial cells with one or more characteristics of the choroidal epithelium, including organic transport proteins. In the brain, the growing families of organic anion transporting polypeptides (Oatp/OATP) and multidrug resistance-associated proteins (Mrp/MRP) mediate the flux of amphiphilic, anionic and in some cases even cationic molecules across the blood cerebrospinal fluid barrier (Advanced Drug Delivery Reviews (2004) 56:1859-1873). These transport proteins also include, but are not limited to, the MDR1 (multidrug resistance) P glycoprotein (Pgp), and the multidrug resistance-associated protein (MRP), a homologous ATP-binding cassette transporter (Proc. Natl. Acad. Sci. (1999) 96:3900-3905). The transporters are involved in the clearance of potentially toxic compounds, as well as many drugs (including, but not limited to, β-lactam antibiotics, cephalosporins, cytostatic drugs, and antiviral agents), from the cerebrospinal fluid. In some embodiments, the organic transport proteins include, but are not limited to, organic anion transporting polypeptides, multidrug resistance-associated proteins, ATP-binding cassette transporters, and multidrug resistance proteins. In some embodiments, the organic transport proteins of the apical membrane of the choroidal plexus are partially or completely oriented toward the internal cavity of the device. In other embodiments, the organic transport proteins of the apical membrane of the choroidal plexus are partially or completely oriented toward the exterior of the device. In some embodiments, the organic transport proteins of the basolateral membrane of the choroidal plexus are partially or completely oriented toward the internal cavity of the device. In other embodiments, the organic transport proteins of the basolateral membrane of the choroidal plexus are partially or completely oriented toward the exterior of the device. In some embodiments, the localization and/or action of organic transport proteins may result in partially or completely unidirectional transport of toxic compounds. The unidirectional transport may occur in either orientation, partially or completely toward the internal cavity, or partially or completely toward the exterior of the device.

In yet other embodiments, the semi-permeable membrane is composed of epithelial cells with one or more characteristics of the choroidal epithelium, including differential localization of organic transport proteins between interior and exterior membranes of the device. The differential localization of transport proteins in the choroid plexus epithelium has a different polarity than that observed in the epithelium of the kidneys or liver (Microscopy Research and Technique (2001) 52:60-64). The Na⁺/K⁺-ATPase is localized at the apical plasma membrane domain, and the first step in organic anion removal from the cerebrospinal fluid requires substrate uptake across the apical plasma membrane domain of choroid plexus epithelial cells. Therefore, unlike in the kidneys, the "kidney-like" excretory system for organic anions is located at the apical side of the choroid plexus epithelium.

In some embodiments, the semi-permeable membrane has epithelial cells containing members of the organic anion transporter (OAT) family that are oriented toward the internal cavity. In other embodiments, the semi-permeable membrane has epithelial cells containing members of the organic anion transporter (OAT) family that are oriented away from the internal cavity. In other embodiments, the semi-permeable membrane has epithelial cells containing members of the organic cation transporter (OCT) family that are oriented toward the internal cavity. In yet other embodiments, the semi-permeable membrane has epithelial cells containing members of the organic cation transporter (OCT) family that are oriented away from the internal cavity.

In some embodiments, the choroid plexus epithelial cells that form the semi-permeable component may contain liver-like transport properties. In another embodiment, one or more liver-like organic anion transporters are expressed in the choroidal epithelium forming the semi-permeable membrane of the device. These transporters may include, but are not limited to, the family of organic anion transporting proteins (Oatps; OATPs). The organic anion transporting proteins may be differentially expressed (have a polar distribution) between the apical and basolateral surfaces of the choroid plexus epithelium. For example, organic anion transporting protein 1 may be expressed at the apical, and organic anion transporting protein 2 at the basolateral surface.

In some embodiments, the semi-permeable membrane has epithelial cells containing members of the organic anion transporting protein family that are oriented toward or away from the internal cavity. In other embodiments, the semi-permeable membrane has epithelial cells containing members of the organic anion transporting protein family that have a polar orientation, with one or more family members oriented toward the internal cavity, and a different one or more family members oriented away from the internal cavity. In some embodiments, the localization and/or action of organic anion transporting protein family may result in partially or completely unidirectional transport of toxic compounds. The unidirectional transport may occur in either orientation, partially or completely toward the internal cavity, or partially or completely toward the exterior of the device.

In yet other embodiments, the choroid plexus epithelial cells that form the semi-permeable component may contain one or more members of the ATP-binding cassette transporter family. In some embodiments, the one or more members of the ATP-binding cassette transporter family may include one or more members of the multidrug resistance protein (Mrp/MRP) subfamily. At least one member of the multidrug resistance protein subfamily (MRP1) has been localized to the basolateral membrane of the choroid plexus epithelium. MRP1 is a versatile multispecific organic substrate pump that can mediate ATP-dependent efflux of a large variety of organic compounds, and in the presence of normal intracellular glutathione, many neutral and basic organic compounds. In some embodiments, the semi-permeable membrane has epithelial cells containing members of the ATP-binding cassette transporter family and/or one or more members of the multidrug resistance protein (Mrp/MRP) subfamily that are oriented toward or away from the internal cavity.

In yet other embodiments, the choroid plexus epithelial cells that form the semi-permeable component may contain one or more members of the multidrug resistance (MDR) P glycoprotein family. In brain choroid plexus epithelium, the MDR1 P glycoprotein has been localized to the apical plasma membrane and a subapical vesicular compartment (Proc. Natl. Acad. Sci. (1999) 96:3900-3905). This localization would confer an apical to basal transepithelial permeation barrier for MDR1 substrates. In some embodiments, the semi-permeable membrane has epithelial cells containing members of the multidrug resistance P glycoprotein family that are oriented toward or away from the internal cavity.

In some embodiments, the active or catalyzed transport systems of the epithelial cells that form the semi-permeable component of the device include one or more of organic anion and cation transporters, ABC transporters, ATA2, PepT2, transthyretin, transferrin receptor, and Na+, K+-ATPase.

In some embodiments, the semi-permeable component has epithelial cells that produce and secrete cerebrospinal fluid proteins including, but not limited to, transthyretin (pre-albumin), ascorbic acid, and myo-inositol.

In some embodiments, the semi-permeable component has infoldings or interdigitations. In some embodiments, the infoldings or interdigitations are oriented toward the internal cavity. In other embodiments, the infoldings or interdigitations are oriented toward the exterior of the device, or away from the internal cavity. In some embodiments, the infoldings or interdigitations form the internal cavity. In other embodiments, the infoldings or interdigitations form the exterior of the device. In vivo, the choroid epithelium contains extensive basolateral infoldings that provide a substantial surface for transport (Pharmaceutical Research (2005) 22:1011-1037). In some embodiments, there are at least approximately 2, 5, 10, 25, 50 or 100 times more interdigitations per epithelial cross section than in non-choroidal epithelium. In yet other embodiments, there are 2 to 5, 5 to 10, 100 to 50, 50 to 100, or 100 to 1000 times more interdigitations per epithelial cross section than in non-choroidal epithelium.

In other embodiments, the semi-permeable component includes epithelial cells with microvilli and/or with greater numbers and/or volume of microvilli as compared with non-choroidal epithelium. In the brain, the choroid epithelium contains lush apical membrane microvilli that provide a massive surface area for molecular fluxes (Pharmaceutical Research (2005) 22:1011-1037). In some embodiments, the microvilli are partially or completely oriented toward the internal cavity. In other embodiments, the microvilli are partially or completely oriented toward the exterior of the device, or away from the internal cavity. In some embodiments, the microvilli partially or completely form the internal cavity. In other embodiments, the microvilli partially or completely form the exterior of the device. In some embodiments, there are at least approximately 2, 5, 10, 25, 50 or 100 times more microvilli per epithelial cross section than in non-choroidal epithelium. In yet other embodiments, there are 2 to 5, 5 to 10, 10 to 50, 50 to 100, or 100 to 1000 times more microvilli per epithelial cross section than in non-choroidal epithelium.

In yet other embodiments, the semi-permeable component has epithelial cells containing a greater number and/or volume of mitochondria as compared with peripheral epithelium. The increase in mitochondria, and therefore energy potential, provide the energy for substantial secretion and reabsorption (Pharmaceutical Research (2005) 22:1011-1037). In some embodiments, there are approximately 2, 3, 4, 5, 6, 7, 8, 9, or 10 times more mitochondria per epithelial cross section than in non-choroidal epithelium. In yet other embodiments, there are 2 to 4, 3 to 5, 4 to 7, 8 to 10, 3 to 8, or 2 to 6 times more mitochondria per epithelial cross section than in non-choroidal epithelium.

In some embodiments, the semi-permeable component has epithelium with a defined polarity reflecting the polarity of the apical and basolateral surfaces of the choroid plexus epithelium. As used herein, the term "basolateral" refers to the internal surface of the choroid plexus epithelium that faces the capillary endothelium. The basolateral surface of the epithelium surrounds the fenestrated capillary through which blood flows in vivo. As used herein, the term "apical" refers to the exterior surface of the choroid plexus epithelium. The apical surface of the epithelium is in contact with the cerebrospinal fluid that bathes the brain, including the ventricles.

In some embodiments, polarity of the choroid plexus epithelium and the semi-permeable component is defined through differences in membrane structure and/or location of tight junctions on or near one surface as compared with another surface. In other embodiments, polarity is defined through presence or absence of membrane structures and/or location of tight junctions on one surface as compared with the other surface. For example, microvilli are usually associated with the apical surface of the choroid plexus epithelium, and basolateral interdigitations are associated with the basal surface of the choroid plexus epithelium. Tight junctions are typically formed between cells on adjacent surfaces toward the apical surface of the choroid plexus epithelium.

In some embodiments, polarity of the choroid plexus epithelium and the semi-permeable component is defined through differences in one or more transporter systems, which may include but are not limited to, ion transport proteins, nutrient transporters, organic transport proteins and ATP-binding cassette members, present on one surface as compared with the other surface. In other embodiments, polarity is defined through presence or absence of one or more transporter systems which may include but are not limited to, ion transport proteins, nutrient transporters, organic transport proteins and ATP-binding cassette members, on one surface as compared with the other surface. For example, ion transporters including, but not limited to, $Na^+$—$K^+$ ATPase, $K^+$ channels, and $Na^+$-$2Cl^-$—$K^+$ cotransporters, and aquaporin 1 are typically located on the apical membrane of the choroid plexus epithelium. Ion transporters including, but not limited to, $Cl^-$—$HCO_3$ exchangers, a variety of $Na^+$ coupled $HCO_3^-$ transporters, and $K^+$—Cl cotransporters are typically located on the basolateral membrane of the choroid plexus epithelium. Organic transport proteins including, but not limited to, the organic anion transporter are typically located on the apical membrane of the choroid plexus epithelium. Organic anion transporters including, but not limited to, organic anion transporting proteins have members of the family preferentially localized to either the apical or basal membranes. ATP-binding cassette members including, but not limited to, multidrug resistance protein 1 are typically located on the basolateral surface of the choroid epithelium, while P glycoprotein is typically located on the apical surface of the choroid plexus epithelium.

In yet other embodiments, polarity of the choroid plexus epithelium and the semi-permeable component is defined through differences in secretion and/or presence or absence of secretion of proteins from one surface as compared with the other. For example, cerebrospinal fluid, transthyretin, ascorbic acid, and myo-inositol are typically secreted from the apical surface.

In some embodiments, the basolateral surface is oriented toward the internal cavity of the semi-permeable component of the device. In other embodiments the apical surface is oriented toward the internal cavity of the semi-permeable component of the device.

Figure 6B:
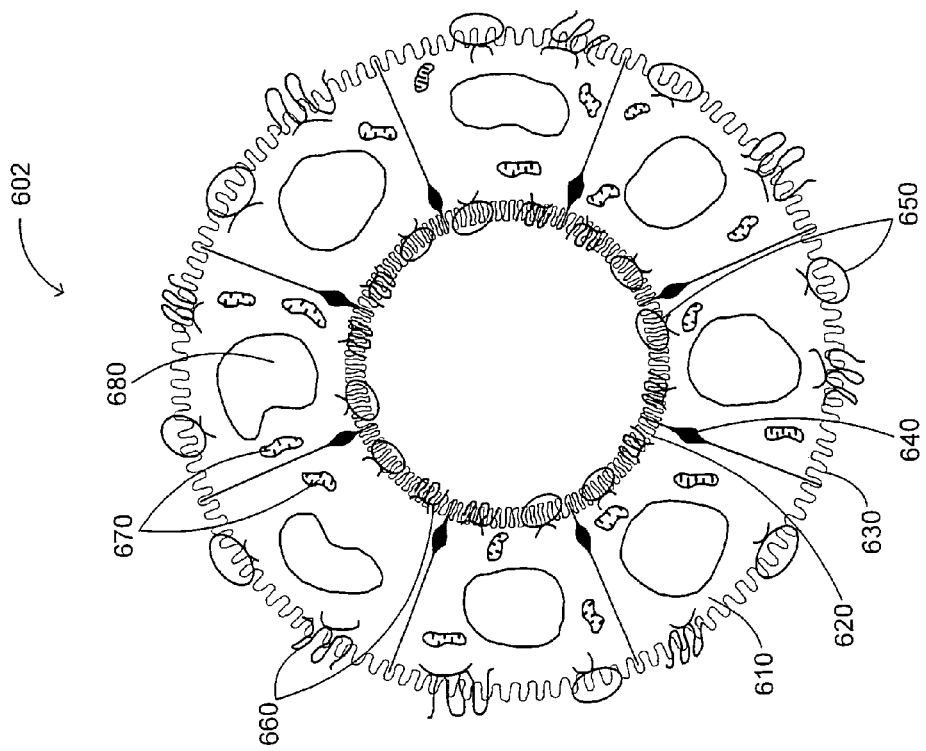
FIGS. 6A and 6B are schematic representations of an illustrative blood cerebrospinal fluid device.
Figure 6A:
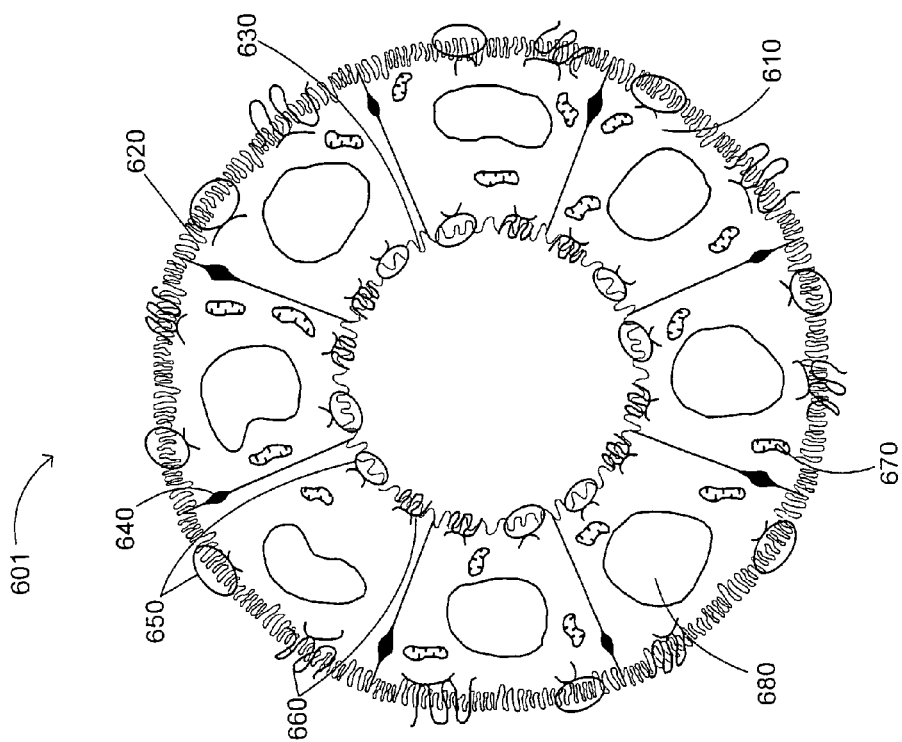

Illustrative embodiments showing blood cerebrospinal fluid barrier devices are shown in FIG. 6. FIG. 6A shows a cross-section of one orientation of an ovoid choroid plexus epithelium device 601 comprised of epithelial cells 610 optionally containing exterior plasma membrane microvilli 620, interior plasma membrane interdigitations 630, interepithelial tight junctions 640 near the external surface, ion transport systems 650 on interior and exterior plasma membranes, organic transport systems on interior and exterior plasma membranes 660, mitochondria 670 and nuclei 680. FIG. 6B shows a cross-section of another orientation of an ovoid choroid plexus epithelium device 602 comprised of epithelial cells 610 optionally containing interior plasma membrane microvilli 620, exterior plasma membrane interdigitations 630, interepithelial tight junctions 640 near the internal surface, ion transport systems 650 on interior and exterior plasma membranes, organic transport systems 660 on interior and exterior plasma membranes, mitochondria 670 and nuclei 680.

In some embodiments, the epithelium that makes part or all of the semi-permeable component is autologous, allogeneic, or xenogeneic with respect to a subject. The epithelium ma) be cultured in vitro. The epithelial cells may be from primary brain epithelium, from peripheral epithelium, from an epithelial cell line, or from stem cells. The epithelium may be genetically engineered, designed to partially or completely prevent restructuring, designed to partially or completely enhance restructuring, be immunogenic, be non-immunogenic, and/or be recognized as self.

In some embodiments, the blood cerebrospinal fluid barrier device may be implantable and biocompatible, and may also include a structural component. The epithelium may at least partially or completely form an internal cavity. The structural component may at least partially or completely form an internal cavity. The combination of the epithelium and the structural component may partially or completely form an internal cavity. In some embodiments, the structural component may surround the epithelium. In other embodiments, the epithelium may surround the structural component. The structural component may be at least partially composed of bone or of cartilage.

In some aspects, a method of making a blood cerebrospinal fluid barrier device includes, but is not limited to, forming a semi-permeable membrane from epithelial cells, configuring the semi-permeable membrane to at least partially form an internal cavity, and engineering the epithelial cells to have one or more characteristics of a blood cerebrospinal fluid barrier membrane. In some embodiments, at least one of the one or more characteristics of the blood cerebrospinal fluid barrier membrane is not a characteristic of peripheral epithelium. In some embodiments, a method of making a device includes culturing cells in vitro. In some embodiments, the cells include, but are not limited to, epithelial cells, stem cells, and brain epithelial cells. In yet other embodiments, a method of making a device includes differentiating epithelial cells from stem cells, and/or culturing stem cells in vitro. In some embodiments, the blood cerebrospinal fluid barrier device includes cells that are isolated from autologous, allogeneic, or xenogeneic donors.

In yet other embodiments, a method of making a device includes configuring the semi-permeable membrane to at least partially form an internal cavity by culturing epithelial cells on a scaffold to at least partially form the internal cavity. In some embodiments, a method of making a device includes configuring the scaffold to at least partially form the internal cavity.

In yet other embodiments, a method of making a device includes selecting a structural component, and combining the structural component and the semi-permeable membrane. In some embodiments, a method of making a device includes selecting a structural component, and placing the semi-permeable membrane in the structural component. In some embodiments, a method of making a device includes selecting a structural component, and placing the structural component in the semi-permeable membrane. In yet other embodiments, a method of making a device includes selecting a structural component, and at least partially surrounding the structural component with the semi-permeable membrane. In yet other embodiments, a method of making a device includes selecting a structural component, and at least partially surrounding the semi-permeable membrane with the structural component.

In yet other embodiments, a method of making a device includes identifying one or more biologically active molecules, and providing the one or more biologically active molecules to the internal cavity of the device. In yet other embodiments, a method of making a device includes identifying one or more living cells or tissues, and providing the one or more living cells or tissues to the internal cavity. In some embodiments, the one or more living cells and tissues produce the one or more biologically active molecules.

In other aspects, a method for delivering one or more biologically active molecules to a subject includes, but is not limited to, identifying one or more biologically active molecules useful to a subject, and implanting in the subject one or more of the blood cerebrospinal fluid barrier devices described in this disclosure. In some embodiments, a method of making a device includes adding the one or more biologically active molecules to the one or more devices before or after implantation of the devices in a subject in need of the biologically active molecules. In some embodiments, a method of making a device includes identifying one or more living cells or tissues, and providing the one or more living cells or tissues to the one or more devices. In some embodiments, the one or more living cells and tissues produce the one or more biologically active molecules.

In yet other aspects, a method of assembling a device for delivering one or more biologically active molecules to a subject, includes identifying the one or more biologically active molecules, selecting one or more of the blood cerebrospinal fluid barrier devices described herein, and providing the one or more biologically active molecules to the device. In some embodiments, a method of making a device includes identifying one or more one or more living cells or tissues, and providing the one or more living cells or tissues to the one or more devices. In some embodiments, the one or more living cells and tissues produce the one or more biologically active molecules.

Models for the blood cerebrospinal fluid barrier using, among others, isolated choroid plexus, cultured epithelial cells from the choroid plexus, and immortalized choroid plexus epithelial cell lines, have been developed (Advanced Drug Delivery Reviews (2004) 56:1875-1885; Advanced Drug Delivery Reviews (2004) 56:1859-1873; Proc. Natl. Acad. Sci. (1999) 96:3900-3905).

In other embodiments, the bone cage comprises one or more biologically active molecules. In some embodiments, the one or more biologically active molecules are surrounded by the semi-permeable component. In other embodiments, the one or more biologically active molecules are bound to the bone cage. In other embodiments, the bone binds one or more biologically active molecules. In some embodiments, the bone binds these molecules following their release from the bone cage and/or living cells and/or tissues. In some embodiments, the one or more biologically active molecules comprise part of the bone wall. In other embodiments, the one or more biologically active molecules are bound to the semi-permeable component and/or one or more living cells or tissues. In yet other embodiments, the one or more biologically active molecules are released from, provided by, secreted from, and/or diffuse from cells of the bone wall, the semi-permeable component, and/or one or more living cells or tissues.

As used herein, the term "biologically active molecules" includes any molecule that has a measurable biological action in a subject. For example, biologically active molecules would include, but not be limited to, any molecules described in this disclosure including, but not limited to, molecules that enhance or reduce bone restructuring including bone resorption and deposition, and/or that enhance or reduce an immune response. In illustrative embodiments, these biologically active molecules would include, but not be limited to, pharmaceutically acceptable compounds including parenteral drugs, nutrients, and vitamins including, but not limited to those described in this disclosure for the treatment of particular diseases or disorders.

In illustrative embodiments, the one or more biologically active molecules include, but are not limited to, hormones such as adrenalin, adrenocorticotropic hormone (ACTH), aldosterone, antidiuretic hormone (Vasopressin), calcitonin, cholecystokinin, cortisol, insulin, gastrin, glucagon, glucocorticoids, gonadotropin-releasing hormone, luteinizing and follicle stimulating hormones, growth hormone, estrogen, testosterone and thyroid hormone. In other embodiments, the one or more biologically active molecules include, but are not limited to, hormones of the gut, such as gastrin, secretin, cholecystokinin, somatostatin and neuropeptide Y. In other embodiments, the one or more biologically active molecules include, but are not limited to hormones of the hypothalamus such as thyrotropin-releasing hormone (TRH), gonadotropin-releasing hormone (GnRH), growth hormone-releasing hormone (GHRH), ghrelin, corticotropin-releasing hormone (CRH), somatostatin, dopamine, antidiuretic hormone (ADH), obestatin and oxytocin. In other embodiments, the one or more biologically active molecules include, but are not limited to hormones of the kidney such as renin, erythropoietin (EPO) and calcitriol. In other embodiments, the one or more biologically active molecules include, but are not limited to hormones of the liver such as insulin-like growth factor-1 (IGF-1), angiotensinogen, and thrombopoietin. In other embodiments, the one or more biologically active molecules include, but are not limited to hormones of the pituitary including those from the anterior lobe such as thyroid stimulating hormone (TSH), follicle-stimulating hormone (FSH), luteinizing hormone (LH), prolactin (PRL), growth hormone (GH), and adrenocorticotropic hormone (ACTH), as well as the posterior lobe such as antidiuretic hormone (ADH) and oxytocin. In other embodiments, the one or more biologically active molecules include, but are not limited to, hormones of the reproductive system such as estrogens, progesterone, testosterone, and anabolic steroids. In other embodiments, the one or more biologically active molecules include, but are not limited to, leptin, ghrelin, obestatin, resistin, melanocyte-stimulating hormone (MSH), parathyroid hormone, melatonin and prolactin.

In other embodiments, the bone cage comprises one or more living cells or tissues. In some embodiments, a semi-permeable component surrounds the one or more living cells or tissues. In some embodiments, the cells are autologous, allogeneic, or xenogeneic with respect to a subject within whom or which they may be implanted. In some embodiments, the cells are cultured in vitro. In some embodiments the cells are non-immunogenic and/or are recognized as self by a subject within whom or which they is implanted. In some embodiments, the one or more living cells or tissues have been genetically engineered. In some embodiments, the one or more living cells or tissues have been genetically engineered to release, provide, diffuse and/or extrude the one or more biologically active molecules.

In some embodiments, the one or more living cells and/or tissues include, but are not limited to, cells and/or tissues that produce, express and/or secrete immune/inflammation-related, biochemical function-related, metabolism-related, and/or hormone-related biologically active molecules. In illustrative embodiments, the one or more living cells and/or tissues include, but are not limited to, bacteria, yeast, islet cells, liver cells, thyroid cells, bone cells, and/or neural cells.

Other aspects include methods for delivering one or more biologically active molecules to a subject. The one or more biologically active molecules to be delivered to the subject are identified and/or selected by methods well-known in the art, for example by health care workers including, but not limited to, physicians responsible for the health of the subject. One or more of the bone cages described above are selected for delivery of the one or more biologically active molecules. The one or more biologically active molecules may be provided with or added to the bone cages, and/or released from one or more living cells or tissues provided with or added to the bone cages, and/or released from the cells comprising the semi-permeable component provided with or added to the bone cages. The one or more bone cages containing the one or more biologically active molecules and/or living cells or tissues and/or semi-permeable component are implanted in the subject to allow delivery of the one or more biologically active molecules.

Yet other aspects include methods for assembling a device for delivering one or more biologically active molecules to a subject. The one or more biologically active molecules to be delivered to the subject are identified and/or selected by methods well-known in the art, for example by health care workers including, but not limited to, physicians responsible for the health of the subject. One or more of the bone cages described above are selected for delivery of the one or more biologically active molecules. The one or more biologically active molecules may be provided with or added to the bone cages, and/or released from one or more living cells or tissues provided with or added to the bone cages, and/or released from the cells comprising the semi-permeable component provided with or added to the bone cages. The one or more bone cages containing the one or more biologically active molecules and/or living cells or tissues and/or semi-permeable component are implanted in the subject to allow delivery of the one or more biologically active molecules.

Other aspects include methods of using one or more bone cages to treat, ameliorate, and/or prevent one or more diseases and/or disorders. In some embodiments, the one or more diseases and/or disorders include, but are not limited to, immune-related, biochemical function-related, metabolism-related, hormone-related, wound healing, burns, surgical incisions, joint ailments, bone-related, obesity, addiction, and/or neurological-related.

In illustrative embodiments, use of bone cages in the treatment, amelioration and/or prevention of immune and/or inflammation-related diseases and/or disorders includes, but is not limited to, enhancing the immune response to treat for example malignancies and/or infections, and creation of tolerance to treat, for example, allergies, asthma, and autoimmune disorders.

In illustrative embodiments, use of bone cages in the treatment, amelioration and/or prevention of biochemical function-related and/or metabolism-related diseases and disorders includes, but is not limited to aspects of liver and/or pancreas dysfunction. In illustrative embodiments for liver dysfunction, allogeneic or xenogeneic liver cells, optionally including stem cells, are placed within one or more bone cages to perform toxin processing, metabolize protein, metabolize carbohydrates, and/or treat lysosomal storage disorders and fatty acid oxidation defects. In illustrative embodiments for pancreas dysfunction, allogeneic or xenogeneic Islet cells are placed within one or more bone cages to produce insulin.

In illustrative embodiments, use of bone cages in the treatment, amelioration and/or prevention of hormone-related diseases and disorders includes, but is not limited to, hypothyroidism, panhypopituitarism, osteoporosis, adrenal insufficiency, and/or sex hormone deficiency. In some embodiments, allogeneic and/or xenogeneic donor cells replace the deficient hormones. In other embodiments, genetically engineered cells, for example stem cells, bacteria and/or yeast, replace the deficient hormones.

FIGS. 4A, 4B, 4C, 4D, 4E, 4F, 4G, and 4H show tables 401, 402, 403, 404, 405, 406, and 407, respectively, that describe diseases and disorders in a column entitled Disease 410 that can be treated, ameliorated and/or prevented using one or more of the bone cages described in this disclosure. For example, cells or tissues containing non-defective versions of the system or enzyme described in the column entitled Defective Enzyme or System 420 can be administered to a subject in need of such treatment by implantation of one or more bone cages. Subjects in need of treatment are identified according to their symptoms, for example, as described in the column entitled Symptoms 430. In addition, a current treatment, shown in the column entitled Treatment 440, can be administered to a subject in need of such treatment by use of one or more bone cages.

All references are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device comprising:
   a bone cage at least partially forming an internal cavity,
   a semi-permeable component including a tissue coating comprising choroid plexus epithelial cells cultured on and supported by a scaffold, the semi-permeable component at least partially enclosing the bone cage, the semi-permeable component having one or more characteristics of a choroid plexus epithelium, and
   wherein at least one characteristic of the one or more characteristics of the choroid plexus epithelium is different from the characteristic in peripheral epithelium.

2. The device of claim 1, wherein the at least one characteristic of the one or more characteristics of the choroid plexus epithelium that is different from the characteristic in the peripheral epithelium includes one or more of interepithelial tight junctions, interepithelial electrical resistance, apical microvilli, basolateral interdigitations, mitochondria, transport systems, or polarity between apical and basal surfaces.

3. The device of claim 2, wherein the interepithelial electrical resistance in the semi-permeable component is increased in value compared with the interepithelial electrical resistance in the peripheral epithelium.

4. The device of claim 2, wherein the apical microvilli of epithelial cells in the semi-permeable component are increased compared with microvilli in the peripheral epithelium.

5. The device of claim 2, wherein the basolateral interdigitations of the epithelial cells in the semi-permeable component are increased compared with interdigitations in the peripheral epithelium.

6. The device of claim 2, wherein the mitochondria in cytoplasm of the semi-permeable component are increased compared with the mitochondria in the peripheral epithelium.

7. The device of claim 2, wherein one or more of the transport systems of epithelial cells of the semi-permeable component are at elevated concentrations compared with the transport systems in the peripheral epithelium.

8. The device of claim 2, wherein one or more of the transport systems of epithelial cells of the semi-permeable component are differentially localized compared with the transport systems in the peripheral epithelium.

9. The device of claim 2, wherein the one or more characteristics of the choroid plexus epithelium is polarity between the apical and basal surfaces of the choroid plexus epithelium.

10. The device of claim 9, wherein the basal surface of the choroid plexus epithelium is oriented toward the internal cavity.

11. The device of claim 9, wherein the apical surface of the choroid plexus epithelium is oriented toward the internal cavity.

12. The device of claim 1, for implantation in a subject, wherein the semi-permeable component is autologous, allogeneic or xenogeneic with respect to the subject.

13. The device of claim 12, wherein the subject is selected from the group consisting of a domesticated animal, a farm animal, a marine animal, a sport animal, a wild animal, a research animal, a zoo animal, a bird, an amphibian, a reptile, a fish and a mammal.

14. The device of claim 1, wherein the semi-permeable component is genetically engineered.

15. The device of claim 1, wherein the semi-permeable component is designed to at least partially prevent bone restructuring.

16. The device of claim 1, wherein the semi-permeable component is designed to at least partially enhance restructuring.

17. The device of claim 1, for implantation in a subject, wherein the semi-permeable component is non-immunogenic with respect to the subject.

18. The device of claim 1, for implantation in a subject, wherein the semi-permeable component is recognized as self by the subject.

19. The device of claim 1, wherein the device is implantable.

20. The device of claim 1, further comprising one or more living cells or tissues.

21. The device of claim 20, wherein the one or more living cells or tissues are at least partially located in the internal cavity.

22. The device of claim 20, for implantation in a subject, wherein the one or more living cells or tissues are autologous, allogeneic or xenogeneic with respect to the subject.

23. The device of claim 20, for implantation in a subject, wherein the one or more living cells or tissues deliver one or more biologically active molecules to the subject.

24. The device of claim 1, further comprising one or more biologically active molecules.

25. The device of claim 24, wherein the one or more biologically active molecules are at least partially located in the internal cavity.

* * * * *